US010858358B2

(12) United States Patent
McMaster et al.

(10) Patent No.: US 10,858,358 B2
(45) Date of Patent: *Dec. 8, 2020

(54) S1PR2 ANTAGONISTS AND USES THEREFOR

(71) Applicant: DALHOUSIE UNIVERSITY, Halifax (CA)

(72) Inventors: Christopher McMaster, Halifax (CA); Gordon Simms, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/586,498

(22) Filed: Sep. 27, 2019

(65) Prior Publication Data

US 2020/0017494 A1 Jan. 16, 2020

Related U.S. Application Data

(63) Continuation-in-part of application No. 16/269,339, filed on Feb. 6, 2019, now Pat. No. 10,487,082, which is a continuation-in-part of application No. 16/234,014, filed on Dec. 27, 2018, which is a continuation of application No. 15/578,998, filed as application No. PCT/CA2016/050620 on Jun. 1, 2016, now abandoned.

(60) Provisional application No. 62/169,375, filed on Jun. 1, 2015.

(51) Int. Cl.

| C07D 471/04 | (2006.01) |
| C07C 317/48 | (2006.01) |
| C07C 229/24 | (2006.01) |
| C07F 9/38 | (2006.01) |
| C07J 31/00 | (2006.01) |
| A61P 27/02 | (2006.01) |
| A61P 9/10 | (2006.01) |
| A61P 25/28 | (2006.01) |
| A61P 9/00 | (2006.01) |
| A61P 3/10 | (2006.01) |
| A61P 9/12 | (2006.01) |
| A61P 11/00 | (2006.01) |
| A61P 15/00 | (2006.01) |
| A61P 25/00 | (2006.01) |
| A61P 19/10 | (2006.01) |
| A61K 31/444 | (2006.01) |
| C07F 9/09 | (2006.01) |
| C07F 9/6558 | (2006.01) |

(52) U.S. Cl.
CPC .......... *C07D 471/04* (2013.01); *A61K 31/444* (2013.01); *A61P 3/10* (2018.01); *A61P 9/00* (2018.01); *A61P 9/10* (2018.01); *A61P 9/12* (2018.01); *A61P 11/00* (2018.01); *A61P 15/00* (2018.01); *A61P 19/10* (2018.01); *A61P 25/00* (2018.01); *A61P 25/28* (2018.01); *A61P 27/02* (2018.01); *C07C 229/24* (2013.01); *C07C 317/48* (2013.01); *C07F 9/3808* (2013.01); *C07J 31/006* (2013.01); *C07F 9/091* (2013.01); *C07F 9/65583* (2013.01)

(58) Field of Classification Search
None
See application file for complete search history.

(56) References Cited

U.S. PATENT DOCUMENTS

| 10,487,082 B2* | 11/2019 | McMaster ................. A61P 9/00 |
| 2004/0235794 A1 | 11/2004 | Nakade et al. |
| 2006/0148844 A1 | 7/2006 | Nakade et al. |
| 2009/0004207 A1 | 1/2009 | Hla et al. |

FOREIGN PATENT DOCUMENTS

| CA | 2775587 A1 | 4/2011 |
| CA | 2868277 A1 | 10/2013 |
| WO | 01/98301 A1 | 12/2001 |
| WO | 03/051876 A1 | 6/2003 |
| WO | 2008/154470 A1 | 12/2008 |
| WO | 2009/074969 A2 | 6/2009 |
| WO | 2010/030976 A2 | 3/2010 |
| WO | 2011/041287 A1 | 4/2011 |
| WO | 2011/058993 A1 | 5/2011 |
| WO | 2011/084486 A1 | 7/2011 |
| WO | 2011/087051 A1 | 7/2011 |
| WO | 2011/159864 A1 | 12/2011 |
| WO | 2012/164103 A2 | 12/2012 |

OTHER PUBLICATIONS

PCT Search Report and Written Opinion dated Aug. 11, 2016 in PCT Application No. PCT/CA2016/050620, filed on Jun. 1, 2016 to Applicant Dalhousie University, 19 pages.

Sumida, G., et al., "S1P2 receptor Regulation of Sphingosine-1-Phosphate Effects on Conventional Outflow Physiology". American Journal of Physiology—Cell Physiology, Feb. 2, 2011 (Feb. 2, 2011), vol. 300, pp. C1164-C1171, abstract.

Xu, Q. et al., "Vascular Development in the Retina and Inner Ear: Control by Norrin and Frizzled-4, a High-Affinity Ligand-Receptor Pair". Cell, Mar. 19, 2004 (Mar. 19, 2004), vol. 116, pp. 883-895, p. 883, cols. 1 and 2.

Junge, H. et al., "TSPAN12 Regulates Retinal Vascular Development by Promoting Norrin-but not Wnt-Induced FZD4/beta-Catenin Signaling". Cell, Oct. 16, 2009 (Oct. 16, 2009), vol. 139, pp. 299-311, p. 299, cols. 1 and 2.

(Continued)

*Primary Examiner* — Zinna Northington Davis
(74) *Attorney, Agent, or Firm* — Polsinelli PC; Ron Galant

(57) ABSTRACT

Methods and compositions are provided for the treatment of familial exudative vitreoretinopathy (FEVR) through the administration of a therapeutically effective amount of a sphingosine-1-phosphate receptor type 2 (S1PR2) antagonist. Also provided herein are (Z)-2-cyano-1-(2,6-dichloropyridin-4-yl)-3-((4-isopropyl-1,3-dimethyl-1H-pyrazolo[3,4-b]pyridin-6-yl)methyl)guanidine and analogs thereof, and their use in treating retinopathies and diseases characterized by insufficient angiogenesis.

20 Claims, 14 Drawing Sheets

(56) References Cited

OTHER PUBLICATIONS

Okamoto, Y. et al., "Sphingosine-1-Phosphate-Specific G Protein-Coupled Receptors as Novel Therapeutic Targets for Atherosclerosis". Pharmaceuticals, Jan. 4, 2011 (Apr. 1, 2011), vol. 4, pp. 117-137.

PCT Search Report and Written Opinion dated Sep. 3, 2015 for PCT/CA2015/050503, filed Jun. 1, 2015, titled Treatment of Familial Exudative Vitreoretinopathy Through S1PR2 Inhibition, Applicant Dalhousie University, 12 pages.

Park et al, "Inhibition of Sphingosine 1-Phosphate Receptor 2 Protects against Renal Ischemia-Reperfusion Injury", J. Am. Soc. Nephrol, Feb. 2012, 23(2), 266-280.

Extended European Search Report dated Nov. 21, 2017 in EP Application No. 15802481.0, filed Dec. 1, 2016 to Dalhousie University, 7 pages.

* cited by examiner

Fzd4-/- mice

Fzd4-/- S1pr2-/- mice

Wild type mice

Fzd4-/- mice treated with JTE-013

Fzd4-/- vehicle control mice

PubChem 3382778    PubChem 44317142

PubChem 54736865    PubChem 3866342

PubChem 46891770    PubChem 51624406

PubChem 9578291

PubChem 9864156

PubChem 365015

PubChem 28094480

PubChem 40592676

PubChem 10883396

PubChem 342302

PubChem 59623845

PubChem 54734912

PubChem 18390590

PubChem 56923928

PubChem 51508548

PubChem 28960354

PubChem 51624683

PubChem 27993

S1PR2 ANTAGONISTS AND USES THEREFOR

FIELD OF THE INVENTION

The present invention generally relates to methods for treating the inherited blinding disorder familial exudative vitreoretinopathy (FEVR) through S1PR2 inhibition. The invention also relates to (Z)-2-cyano-1-(2,6-dichloropyridin-4-yl)-3-((4-isopropyl-1,3-dimethyl-1H-pyrazolo[3,4-b]pyridin-6-yl)methyl)guanidine and analogs thereof, and their use in treating retinopathies and diseases characterized by insufficient angiogenesis.

BACKGROUND OF THE INVENTION

The retina is a thin layer of neural tissue lining the back of the eye responsible for sensing visual stimuli. During development, the retinal vasculature is initiated by endothelial sprouts that lay down the primary arteries and veins that project outward radially from the optic disc to the retinal periphery, with a pair of capillary beds located on either side of the central layer of neurons further penetrating the retina. Once in place, the primary vasculature undergoes maturation to specify arteries and veins, the nascent network is pruned, and the blood-retina barrier is formed. Recruitment of vascular smooth muscle cells and pericytes (also known as mural cells, contractile cells that wrap around endothelial cells of capillaries) aid in stabilization of the newly formed vessels. The molecular mechanisms controlling vessel migration and patterning in the eye are not well understood.

In humans, retinal vascular development is usually accomplished around term birth but is delayed or arrested in FEVR. FEVR is characterized by hypovascularization of the retina due to the failure of peripheral retinal vascularization, followed by secondary aberrant neovascularization. Severe forms of FEVR present with bilateral congenital retinal folds or retinal detachment (FIG. 1). Currently, management of FEVR is by laser and surgery. While interventions improve the chance of retaining vision, more than 75% of eyes remain legally blind despite current best efforts. Despite current laser and surgery treatment, loss of vision occurs in the majority of FEVR patients. The ideal treatment for this condition would entail early detection with early intervention with a therapy that will prevent the complications from progressing altogether.

SUMMARY OF THE INVENTION

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

The discovery of genes that, when mutated, cause FEVR has increased the understanding of the molecular pathways that regulate retinal vascular development. To date, five genes have been identified that cause FEVR: FZD4, LRP5, TSPAN12, NDP and ZNF408. Four of the five known FEVR causing genes form a frizzled receptor signaling complex (FIG. 2). FZD4 is part of the frizzled family of seven transmembrane receptors that are normally activated by the Wnt family of ligands. FZD4 is unique among the frizzled receptor family in that it is specifically activated by the non-Wnt ligand norrin, the product of the NDP gene. Norrin is secreted from Muller glial cells and binds to FZD4 receptors located on vascular endothelial cells. LRP5 is a co-receptor for FZD4 and is required for FZD4 to function. Mutations in FZD4, NDP, and LRP5 have been shown to cause FEVR. (Mutant frizzled-4 disrupts retinal angiogenesis in familial exudative vitreoretinopathy. Robitaille J, MacDonald M L, Kaykas A, Sheldahl L C, Zeisler J, Dubé M P, Zhang L H, Singaraja R R, Guernsey D L, Zheng B, Siebert L F, Hoskin-Mott A, Trese M T, Pimstone S N, Shastry B S, Moon R T, Hayden M R, Goldberg Y P, Samuels M E. Nature Genetics, 32, 326-30 (2002)) (Autosomal recessive familial exudative vitreoretinopathy is associated with mutations in LRP5. Xiaodong Jiao, Valerio Ventruto, Michael T. Trese, Barkur S. Shastry, J. Fielding Hejtmancik. Am J Hum Genet 75, p878-884 (2004)) (A mutation in the Norrie disease gene (NDP) associated with X—linked familial exudative vitreoretinopathy. Z.-Y. Chen, E. M. Battinelli, A. Fielder, S. Bundey, K. Sims, X. O. Breakefield & I. W. Craig. Nature Genetics 5, 180-183 (1993)).

TSPAN12 is expressed in endothelial cells, directly binds to FZD4, and enhances the interaction between norrin, FZD4, and LRP5. It is unclear whether FZD4 signals through the canonical Wnt pathway (FIG. 2), or signals via a non-canonical Wnt pathway. Mutations in TSPAN12 have also been shown to cause FEVR. (Recessive Mutations in ISPAN12 Cause Retinal Dysplasia and Severe Familial Exudative Vitreoretinopathy (FEVR). James A. Poulter; Alice E. Davidson; Manir Ali; David F. Gilmour; David A. Parry; Helen A. Mintz-Hittner; Ian M. Carr; Helen M. Bottomley; Vernon W. Long; Louise M. Downey; Panagiotis I. Sergouniotis; Genevieve A. Wright; Robert E. MacLaren; Anthony T. Moore; Andrew R. Webster; Chris F. Inglehearn; Carmel Toomes. IOVS 53, 2873-2879 (2012).) (Mutations in TSPAN12 cause autosomal-dominant familial exudative vitreoretinopathy. Poulter JA1, Ali M, Gilmour D F, Rice A, Kondo H, Hayashi K, Mackey D A, Kearns L S, Ruddle J B, Craig J E, Pierce E A, Downey L M, Mohamed M D, Markham A F, Inglehearn C F, Toomes C. Am J Hum Genet 86, 248-53 (2010)).

Mouse knockout models for Fzd4, Tspan12, Lrp5, and Ndp serve as accurate mimics of the ocular phenotypes observed in FEVR patients. These models have allowed for a detailed analysis of the FEVR phenotype. An important observation from the mouse studies was that, although retinal vasculature is impaired in mouse models of FEVR, the retina itself appeared morphologically normal, offering a window of opportunity for intervention that could prevent vision loss.

Sphingosine-1-phosphate (S1P) is a blood borne lipid second messenger generated from the metabolism of sphingomyelin through the action of sphingomyelinase, ceramidase, and sphingosine kinase (FIG. 3). The main sites of S1P generation are endothelial cells and erythrocytes. S1P activates the endothelial differentiation family of G protein coupled receptors, named S1PR1-5 (formerly Edg1-5). S1PRs are expressed in different cell types, and regulate numerous biological processes. S1PR1, -2, and -3 function are of particular interest as they are expressed on vascular endothelial cells and regulate vascular development and stability. (Sphingosine 1-phosphate receptor signaling. Rosen H, Gonzalez-Cabrera P J, Sanna M G, Brown S. Annu Rev Biochem. 78, 743-68 (2009).) (Sphingosine 1-phosphate and cancer. Pyne, N J, Pyne, S. Nat Rev Cancer 10, 489-503 (2010)).

S1PR1 is essential for vascular stabilization and increases vascular migration. S1PR1 couples to $G_i$ and activates the phosphatidylinositol 3-kinase pathway, which through Rac affects actin assembly and cell migration. A similar overlapping function has been reported for S1PR3 coupling to $G_q$. In contrast, S1PR2 antagonizes S1PR1 and -3 signaling. S1PR2 primarily activates $G_{12/13}$ and activates the Rho-Rho kinase pathway and inhibits Rac function (FIG. 4). The balance between these antagonizing S1PR pathways determines the endothelial cell response to S1P. (Sphingosine 1-phosphate receptor signaling. Rosen H1, Gonzalez-Cabrera P J, Sanna M G, Brown S. Annu Rev Biochem. 78, 743-68 (2009).) (Sphingosine 1-phosphate receptor signaling. Rosen H1, Gonzalez-Cabrera P J, Sanna M G, Brown S. Annu Rev Biochem. 78, 743-68 (2009).)

The present technology provides for a composition and method that safely and effectively treats individuals suffering from FEVR through the administration of therapeutically effective amounts of S1PR2 inhibitors.

In a further aspect, the technology provides a kit comprising a pharmaceutical composition comprising S1PR2 inhibitors, which may include small molecules or biologics, and instructions for administering to a subject the composition for treating a subject who is suffering from FEVR.

As used herein, the term "inhibition" refers to the reduction of biological activity of a protein, preferably the reduction of activity of the human protein S1PR2.

As used herein, the term "gene" is meant a nucleic acid molecule that codes for a particular protein, or in certain cases, a functional or structural RNA molecule.

As used herein, "protein" and "polypeptide" are used synonymously to mean any peptide-linked chain of amino acids, regardless of length or post-translational modification, e.g., glycosylation or phosphorylation.

When referring to a nucleic acid molecule or polypeptide, the term "wild type" refers to a naturally-occurring (e.g., native, WT) nucleic acid or polypeptide.

As used herein, the terms "treatment" and "therapy" are defined as the application or administration of a therapeutic agent to a patient or subject, or application or administration of the therapeutic agent to an isolated tissue or cell line from a patient or subject, who has a disorder or disease, a symptom of disorder or disease or a predisposition toward a disorder or disease, with the purpose to cure, heal, alleviate, relieve, alter, remedy, ameliorate, improve or affect the disorder or disease, the symptoms of disorder or disease, or the predisposition toward disorder or disease.

The term "therapeutically effective amount", as used herein, means the amount of the S1PR2 inhibitor that will elicit the desired therapeutic effect or response.

The terms "patient," "subject" and "individual" are used interchangeably herein, and mean a mammalian (e.g., human, rodent, non-human primates, canine, bovine, ovine, equine, feline, etc.) subject to be treated, diagnosed, and/or to obtain a biological sample from.

The term "kit" as used herein refers to a packaged product comprising components with which to administer the therapeutically effective amount of the S1PR2 inhibitor for treatment of FEVR. The kit preferably comprises a box or container that holds the components of the kit. The box or container is affixed with a label or a Food and Drug Administration approved protocol. The box or container holds components of the technology that are preferably contained within plastic, polyethylene, polypropylene, ethylene, or propylene vessels. The vessels can be capped-tubes or bottles. The kit can also include instructions for administering the S1PR2 inhibitor.

The present invention derives in part from the finding that inhibition of S1PR2 activity (for example, through the administration of a S1PR2 antagonist) is capable of ameliorating vascularization of the retina in subjects that would otherwise exhibit hypovascularization or avascularization during retinal development followed by aberrant ocular neovascularization that may compromise retinal integrity and function, for example in subjects with FEVR. In particular, as shown herein, administration of a S1PR2 antagonist can ameliorate the developmental hypovascularization or avascularization that occurs in this developmental disease and allow for the establishment of a vascular bed during retinal development, thereby avoiding the harmful aberrant neovascularization that would normally follow in such disease afflicted subjects, the overall effect of the S1PR2 antagonist being amelioration of retinal vascularization.

In addition, the present invention relates to S1PR2 antagonists of general formula (IX) in which Z is not —(C=O)— and of general formula (X), described below, which in particular can be used for treating a retinopathy or a disease characterized by insufficient angiogenesis. The S1PR2 antagonist may be administered to a subject in need thereof, and may be contained in a pharmaceutical composition described herein. The retinopathy may be diabetic retinopathy, macular degeneration, hypertensive retinopathy, radiation retinopathy, solar retinopathy, retinopathy of prematurity (ROP), Norrie disease (ND), familial exudative vitreoretinopathy (FEVR), Coats' disease, sickle cell retinopathy, retinitis pigmentosa, or the like. The disease characterized by insufficient angiogenesis may be atherosclerosis, hypertension, diabetes, restenosis, pre-eclampsia, menorrhagia, neonatal respiratory distress, pulmonary fibrosis, nephropathy, osteoporosis, amyotrophic lateral sclerosis, stroke, Alzheimer's disease, or the like.

In one aspect for the S1PR2 antagonists described herein, the invention provides a method for inducing the establishment of a normal retinal vascular bed in a subject at risk of hypovascularization or avascularization of the retina, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for normalizing vascularization of the retina in a subject having reduced Fzd4 activity in the retinal vasculature, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for inducing the establishment of a normal retinal vascular bed in a subject having reduced Fzd4 activity in the retinal vasculature, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for normalizing vascularization of the retina in a subject having reduced NDP activity in the retinal vasculature, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for inducing the establishment of a normal retinal vascular bed in a subject having reduced NDP activity in the retinal vasculature, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for normalizing vascularization of the retina in a subject having reduced TSPAN12 activity in the retinal vasculature, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for inducing the establishment of a normal retinal vascular bed in a subject having reduced TSPAN12 activity in the retinal vasculature, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for normalizing vascularization of the retina in a subject having reduced LRP5 activity in the retinal vasculature, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for inducing the establishment of a normal retinal vascular bed in a subject having reduced LRP5 activity in the retinal vasculature, comprising administering to the subject a therapeutically effective amount of a S1PR2 antagonist. In one embodiment, the subject is at risk of consequent aberrant neovascularization. In one embodiment, the subject is at risk of consequent loss of retinal integrity or retinal detachment. In one embodiment, the subject has or is at risk of FEVR.

In one aspect, the invention provides a method for inducing normal vascularization of a retina in a subject having or at risk of FEVR, comprising administering to the subject a therapeutically effective amount of a S1PR2 antagonist.

In one aspect, the invention provides a method for increasing vascularization of a retina in a subject having or at risk of FEVR, comprising administering to the subject a therapeutically effective amount of a S1PR2 antagonist.

In one aspect, the invention provides a method for reducing hypovascularization or avascularization of the retina in a subject having or at risk of FEVR, comprising administering to the subject a therapeutically effective amount of a S1PR2 antagonist.

In one aspect, the invention provides a method for inducing the establishment of a normal retinal vascular bed in a subject having or at risk of FEVR, comprising administering to the subject a therapeutically effective amount of a S1PR2 antagonist.

In one aspect, the invention provides a method for reducing hypovascularization or avascularization of the peripheral retina in a subject having or at risk of FEVR, comprising administering to the subject a therapeutically effective amount of a S1PR2 antagonist.

In some embodiments described herein, administration of a therapeutically effective amount of a S1PR2 antagonist can be prior to the establishment/appearance of an abnormal hypovascular or avascular retinal region.

In one aspect, the invention provides a method for inducing normal vascularization of the peripheral retina in a subject having or at risk of FEVR, comprising administering to the subject a therapeutically effective amount of a S1PR2 antagonist.

In one aspect, the invention provides a method for increasing vascularization of the peripheral retina in a subject having or at risk of FEVR, comprising administering to the subject a therapeutically effective amount of a S1PR2 antagonist.

In one aspect, the invention provides a method for the inhibition of aberrant neovascularization of the retina in a subject having or at risk of FEVR, comprising administering to the subject a therapeutically effective amount of a S1PR2 antagonist.

In one aspect, the invention provides a method for reducing the loss of retinal integrity in a subject having or at risk of FEVR, comprising administering to the subject a therapeutically effective amount of a S1PR2 antagonist.

In one aspect, the invention provides a method for reducing the loss of vision in a subject having or at risk of FEVR, comprising administering to the subject a therapeutically effective amount of a S1PR2 antagonist.

In one aspect, the invention provides a method for reducing retinal detachment in a subject having or at risk of FEVR, comprising administering to the subject a therapeutically effective amount of a S1PR2 antagonist.

Additionally, in one aspect, the invention provides a composition useful for normalizing vascularization of the retina in a subject at risk of hypovascularization or avascularization of the retina. In one embodiment, the subject is at risk of consequent aberrant neovascularization. In one embodiment, the subject is at risk of consequent loss of retinal integrity or retinal detachment. In one embodiment, the subject has or is at risk of FEVR In one embodiment, the composition is a pharmaceutical composition comprising an S1PR2 antagonist, which pharmaceutical composition is useful for intravitreal administration of the S1PR2 antagonist.

In one aspect, the invention provides a composition useful for inducing the establishment of a normal retinal vascular bed in a subject at risk of hypovascularization or avascularization of the retina. In one embodiment, the subject is at risk of consequent aberrant neovascularization. In one embodiment, the subject is at risk of consequent loss of retinal integrity or retinal detachment. In one embodiment, the subject has or is at risk of FEVR In one embodiment, the composition is a pharmaceutical composition comprising an S1PR2 antagonist, which pharmaceutical composition is useful for intravitreal administration of the S1PR2 antagonist.

In one aspect, the invention provides a composition useful for normalizing vascularization of the retina in a subject having reduced Fzd4 activity in the retinal vasculature. In one embodiment, the subject is at risk of consequent aberrant neovascularization. In one embodiment, the subject is at risk of consequent loss of retinal integrity or retinal detachment. In one embodiment, the subject has or is at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for inducing the establishment of a normal retinal vascular bed in a subject having reduced Fzd4 activity in the retinal vasculature. In one embodiment, the subject is at risk of consequent aberrant neovascularization. In one embodiment, the subject is at risk of consequent loss of retinal integrity or retinal detachment. In one embodiment, the subject has or is at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for normalizing vascularization of the retina in a subject having reduced NDP activity in the retinal vasculature. In one embodiment, the subject is at risk of consequent aberrant neovascularization. In one embodiment, the subject is at risk of consequent loss of retinal integrity or retinal detachment. In one embodiment, the subject has or is at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for inducing the establishment of a normal retinal vascular bed in a subject having reduced NDP activity in the retinal vasculature. In one embodiment, the subject is at risk of consequent aberrant neovascularization. In one embodiment, the subject is at risk of consequent loss of retinal integrity or retinal detachment. In one embodiment, the subject has or is at risk of FEVR In one embodiment, the composition is a pharmaceutical composition comprising an S1PR2 antagonist, which pharmaceutical composition is useful for intravitreal administration of the S1PR2 antagonist.

In one aspect, the invention provides a composition useful for normalizing vascularization of the retina in a subject having reduced LRP5 activity in the retinal vasculature. In one embodiment, the subject is at risk of consequent aberrant neovascularization. In one embodiment, the subject is at risk of consequent loss of retinal integrity or retinal detachment. In one embodiment, the subject has or is at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for inducing the establishment of a normal retinal vascular bed in a subject having reduced LRP5 activity in the retinal vasculature. In one embodiment, the subject is at risk of consequent aberrant neovascularization. In one embodiment, the subject is at risk of consequent loss of retinal integrity or retinal detachment. In one embodiment, the subject has or is at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for normalizing vascularization of the retina in a subject having reduced TSPAN12 activity in the retinal vasculature. In one embodiment, the subject is at risk of consequent aberrant neovascularization. In one embodiment, the subject is at risk of consequent loss of retinal integrity or retinal detachment. In one embodiment, the subject has or is at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for inducing the establishment of a normal retinal vascular bed in a subject having reduced TSPAN12 activity in the retinal vasculature. In one embodiment, the subject is at risk of consequent aberrant neovascularization. In one embodiment, the subject is at risk of consequent loss of retinal integrity or retinal detachment. In one embodiment, the subject has or is at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for inducing normal vascularization of a retina in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for increasing vascularization of a retina in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for reducing hypovascularization or avascularization of the retina in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for the establishment of a normal retinal vascular bed in the retina of a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for reducing hypovascularization of the peripheral retina in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for inducing normal vascularization of the peripheral retina in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for increasing vascularization of the peripheral retina in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for the inhibition of aberrant neovascularization of the retina in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for reducing the loss of retinal integrity in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for reducing the loss of vision in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a composition useful for reducing retinal detachment in a subject having or at risk of FEVR.

In one embodiment, the composition is a pharmaceutical composition comprising an S1PR2 antagonist, which pharmaceutical composition is useful for intravitreal administration of the S1PR2 antagonist.

In one aspect, the invention provides a method for treating a subject having or at risk of FEVR, comprising administering to the subject a therapeutically effective amount of a S1PR2 antagonist.

In one aspect, the invention provides a pharmaceutical composition useful for the treatment of FEVR, comprising a therapeutically effective amount of a S1PR2 antagonist.

In one embodiment, the pharmaceutical composition is useful for intravitreal delivery of the S1PR2 antagonist.

In a further aspect, the invention provides a kit comprising a pharmaceutical composition of the invention, which may include instructions for administering the pharmaceutical composition to a subject in need thereof. In one embodiment, the kit is useful for the treatment of FEVR. In one embodiment, the kit is useful for the treatment of inducing the establishment of a normal retinal vascular bed in a subject at risk of hypovascularization or avascularization of the retina, comprising administering to the subject a therapeutically effective amount of a S1PR2 antagonist. In one embodiment, the kit is useful for the treatment of consequent aberrant neovascularization. In one embodiment, the kit is useful for the treatment of consequent loss of retinal integrity or retinal detachment.

Provided herein is a S1PR2 antagonist compound of formula (XII):

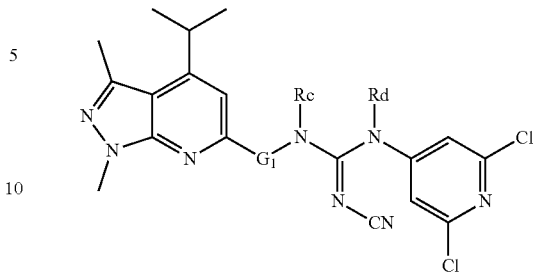

(XII)

or a pharmaceutically-acceptable salt thereof. In formula (XII), $G_1$ may be $CR_{12}$ or $NR_{13}$; $R_{12}$ and $R_{13}$ may each be independently selected from the group consisting of H, $C_1$-$C_4$ alkyl, and benzyl; $R_c$ and $R_d$ may be independently selected from the group consisting of H, $C_1$-$C_4$ alkyl, and benzyl; or $R_c$ and $R_d$ may be joined to form a 5- or 6-membered heterocycloalkyl ring; and, the cyano group may be in the (Z) or (E) configuration.

In one embodiment, $G_1$ is $CR_{12}$ and $R_{12}$ is H; and, $R_d$ is H. In particular, the compound may be: (E)-2-cyano-3-(2,6-dichloropyridin-4-yl)-1-((4-isopropyl-1,3-dimethyl-1H-pyrazolo[3,4-b]pyridin-6-yl)methyl)-1-methylguanidine; (E)-2-cyano-3-(2,6-dichloropyridin-4-yl)-1-ethyl-1-((4-isopropyl-1,3-dimethyl-1H-pyrazolo[3,4-b]pyridin-6-yl) methyl)guanidine; (E)-2-cyano-3-(2,6-dichloropyridin-4-yl)-1-((4-isopropyl-1,3-dimethyl-1H-pyrazolo[3,4-b]pyridin-6-yl) methyl)-1-propylguanidine; (E)-1-butyl-2-cyano-3-(2,6-dichloropyridin-4-yl)-1-((4-isopropyl-1,3-dimethyl-1H-pyrazolo[3,4-b]pyridin-6-yl)methyl) guanidine; (E)-2-cyano-3-(2,6-dichloropyridin-4-yl)-1-isopropyl-1-((4-isopropyl-1,3-dimethyl-1H-pyrazolo [3,4-b]pyridin-6-yl) methyl)guanidine; (E)-1-benzyl-2-cyano-3-(2,6-dichloropyridin-4-yl)-1-((4-isopropyl-1,3-dimethyl-1H-pyrazolo[3,4-b]pyridin-6-yl)methyl)guanidine; or, a diastereomer of the foregoing, wherein the cyano group is in the (Z) form.

In one embodiment, in the compound of formula (XII), $G_1$ is $CR_{12}$ and $R_{12}$ is H; and, $R_c$ is H. In particular, the compound may be: (Z)-2-cyano-1-(2,6-dichloropyridin-4-yl)-3-((4-isopropyl-1,3-dimethyl-1H-pyrazolo[3,4-b]pyridin-6-yl)methyl)-1-methylguanidine; (Z)-2-cyano-1-(2,6-dichloropyridin-4-yl)-1-ethyl-3-((4-isopropyl-1,3-dimethyl-1H-pyrazolo [3,4-b ]pyridin-6-yl)methyl)guanidine; (Z)-2-cyano-1-(2,6-dichloropyridin-4-yl)-3-((4-isopropyl-1,3-dimethyl-1H-pyrazolo[3,4-b]pyridin-6-yl)methyl)-1-propylguanidine; (Z)-1-butyl-2-cyano-1-(2,6-dichloropyridin-4-yl)-3-((4-isopropyl-1,3-dimethyl-1H-pyrazolo[3,4-b]pyridin-6-yl) methyl)guanidine; (Z)-2-cyano-1-(2,6-dichloropyridin-4-yl)-1-isopropyl-3-((4-isopropyl-1,3-dimethyl-1H-pyrazolo[3,4-b]pyridin-6-yl) methyl)guanidine; (Z)-1-benzyl-2-cyano-1-(2,6-dichloropyridin-4-yl)-3-((4-isopropyl-1,3-dimethyl-1H-pyrazolo[3,4-b]pyridin-6-yl) methyl)guanidine; or, a diastereomer of the foregoing, wherein the cyano group is in the (E) form.

In one embodiment, in the compound of formula (XII), $G_1$ is $CR_{12}$; and, $R_c$ and $R_d$ are each H. In particular, the compound may be: (Z)-2-cyano-1-(2,6-dichloropyridin-4-yl)-3-(1-(4-isopropyl-1,3-dimethyl-1H-pyrazolo[3,4-b]pyridin-6-yl)ethyl)guanidine; (Z)-2-cyano-1-(2,6-dichloropyridin-4-yl)-3-(1-(4-isopropyl-1,3-dimethyl-1H-pyrazolo[3,4-b]pyridin-6-yl) propyl)guanidine; (Z)-2-cyano-1-(2,6- dichloropyridin-4-yl)-3-(1-(4-isopropyl-1,3-dimethyl-1H-pyrazolo[3,4-b]pyridin-6-yl)-2-methylpropyl)guanidine; (Z)-2-cyano-1-(2,6-dichloropyridin-4-yl)-3-(1-(4-isopropyl-1,3-dimethyl-1H-pyrazolo[3,4-b]pyridin-6-yl)-2-phenylethyl)guanidine; or, a diastereomer of the foregoing, wherein the cyano group is in the (E) form.

In one embodiment, in the compound of formula (XII), $G_1$ is $NR_{13}$; and, $12_c$ and $R_d$ are each H. In particular, the compound may be: (E)-N'-cyano-N-(2,6-dichloropyridin-4-yl)-2-(4-isopropyl-1,3-dimethyl-1H-pyrazolo[3,4-b]pyridin-6-yl)hydrazinecarboximidamide; (E)-N'-cyano-N-(2,6-dichloropyridin-4-yl)-2-(4-isopropyl-1,3-dimethyl-1H-pyrazolo[3,4-b]pyridin-6-yl)-2-methylhydrazinecarboximidamide; (E)-N'-cyano-N-(2,6-dichloropyridin-4-yl)-2-ethyl-2-(4-isopropyl-1,3-dimethyl-1H-pyrazolo[3,4-b]pyridin-6-yl)hydrazinecarboximidamide; (E)-N'-cyano-N-(2,6-dichloropyridin-4-yl)-2-(4-isopropyl-1,3-dimethyl-1H-pyrazolo[3,4-b]pyridin-6-yl)-2-propylhydrazinecarboximidamide; (E)-2-butyl-N'-cyano-N-(2,6-dichloropyridin-4-yl)-2-(4-isopropyl-1,3-dimethyl-1H-pyrazolo[3,4-b]pyridin-6-yl)hydrazinecarboximidamide; (E)-N'-cyano-N-(2,6-dichloropyridin-4-yl)-2-isopropyl-2-(4-isopropyl-1,3-dimethyl-1H-pyrazolo[3,4-b]pyridin-6-yl)hydrazinecarboximidamide; (E)-2-benzyl-N'-cyano-N-(2,6-dichloropyridin-4-yl)-2-(4-isopropyl-1,3-dimethyl-1H-pyrazolo[3,4-b]pyridin-6-yl)hydrazinecarboximidamide; or, a diastereomer of the foregoing, wherein the cyano group is in the (Z) form.

In one embodiment, in the compound of formula (XII), $G_1$ is $CR_{12}$ and $R_{12}$ is H. In particular, the compound may be: (Z)-2-cyano-1-(2,6-dichloropyridin-4-yl)-3-((4-isopropyl-1,3-dimethyl-1H-pyrazolo[3,4-b]pyridin-6-yl)methyl)-1,3-dimethylguanidine; (Z)-2-cyano-1-(2,6-dichloropyridin-4-yl)-3-isopropyl-3-((4-isopropyl-1,3-dimethyl-1H-pyrazolo[3,4-b]pyridin-6-yl) methyl)-1-methylguanidine; (Z)-2-cyano-1-(2,6-dichloropyridin-4-yl)-1-isopropyl-3-((4-isopropyl-1,3-dimethyl-1H-pyrazolo[3,4-b]pyridin-6-yl)methyl)-3-methylguanidine; (Z)-1-benzyl-2-cyano-3-(2,6-dichloropyridin-4-yl)-1-((4-isopropyl-1,3-dimethyl-1H-pyrazolo[3,4-b ]pyridin-6-yl)methyl)-3-methylguanidine; (Z)-1-benzyl-2-cyano-1-(2,6-dichloropyridin-4-yl)-3-((4-isopropyl-1,3-dimethyl-1H-pyrazolo[3,4-b]pyridin-6-yl)methyl)-3-methylguanidine; or, a diastereomer of the foregoing, wherein the cyano group is in the (E) form In one embodiment, in the compound of formula (XII), $G_1$ is $CR_{12}$ and $CR_{12}$ is H; and, $R_c$ and $R_d$ are joined to form a 5- or 6-membered heterocycloalkyl ring. In particular, the compound may be: (Z)—N-(1-(2,6-dichloropyridin-4-yl)-3-((4-isopropyl-1,3-dimethyl-1H-pyrazolo[3,4-b ]pyridin-6-yl)methyl)tetrahydropyrimidin-2(1H)-ylidene)cyanamide; (Z)—N-(1-(2,6-dichloropyridin-4-yl)-3-((4-isopropyl-1,3-dimethyl-1H-pyrazolo[3,4-b]pyridin-6-yl) methyl)imidazolidin-2-ylidene)cyanamide; or, a diastereomer of the foregoing, wherein the cyano group is in the (E) form.

Also provided herein is a method of treating an eye condition in a subject in need thereof. The method may comprise administering to the subject a pharmaceutically effective amount of a compound of formula (XII), or a pharmaceutically-acceptable salt thereof. The eye condition may be caused by a primary defect in retinal vascularization followed by secondary aberrant neovascularization that can result in retina detachment. The eye condition may also be a retinopathy, which may be diabetic retinopathy, macular degeneration, hypertensive retinopathy, radiation retinopathy, solar retinopathy, retinopathy of prematurity (ROP), Norrie disease (ND), familial exudative vitreoretinopathy (FEVR), Coats' disease, sickle cell retinopathy, or retinitis pigmentosa. The retinopathy may be FEVR.

Also provided herein is a method of treating a disease characterized by insufficient angiogenesis in a subject in need thereof. The method may comprise administering to the subject a pharmaceutically effective amount of the compound of formula (XII), or a pharmaceutically-acceptable salt thereof. The disease may be atherosclerosis, hypertension, diabetes, restenosis, pre-eclampsia, menorrhagia, neonatal respiratory distress, pulmonary fibrosis, nephropathy, osteoporosis, amyotrophic lateral sclerosis, stroke, or Alzheimer's disease.

Additional features and advantages of the disclosure will be set forth in the description which follows and the appended claims.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

1. Compounds

Figure 1:
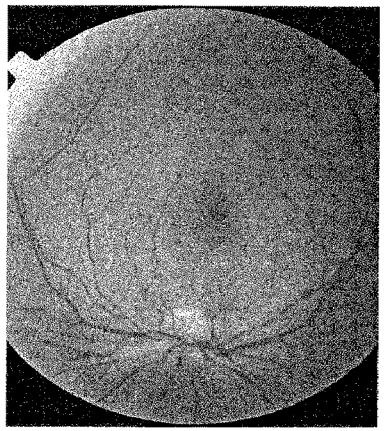
FIG. 1 illustrates vascularization of the human eye. (A) Normally, the retinal vasculature projects outward from the optic disc to the retinal periphery. Familial exudative vitreoretinopathy (FEVR) is an inherited disorder that results in hypovascularization of the retina (B) and subsequent aberrant neovascularization can result in retinal detachment (C).
Figure 1:
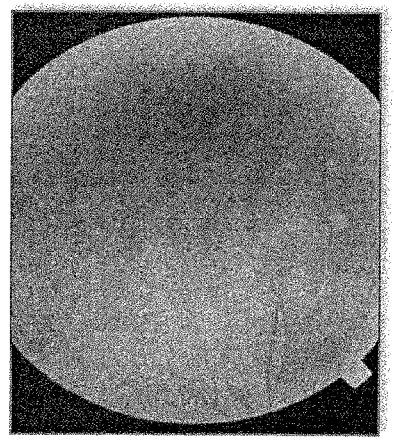
Figure 1:
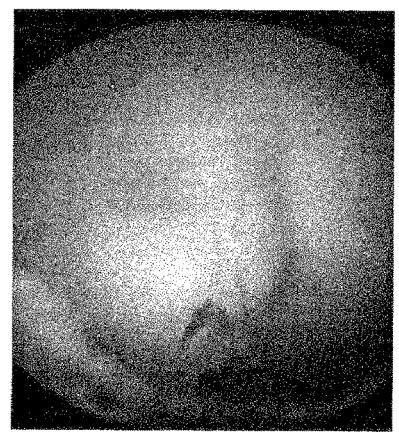
Figure 2:
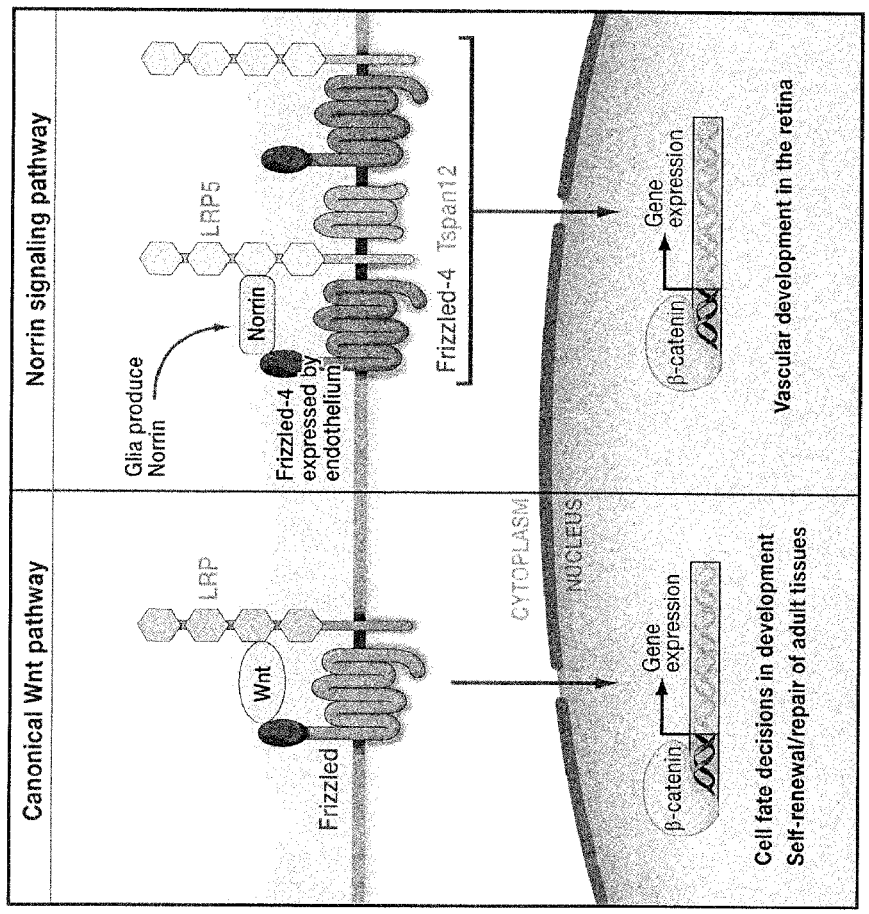
FIG. 2 illustrates the canonical Wnt pathway compared to the Norrin pathway. Norrin signaling through the Frizzled-4 receptor regulates vascular development in the retina, which is hypothesized to signal through beta-catenin. Mutations in the genes encoding for Norrin, Frizzled-4, LRP5, and TSPAN12 cause familial exudative vitreoretinopathy (FEVR). See Cell 139, 227-29 (2009).
Figure 3:
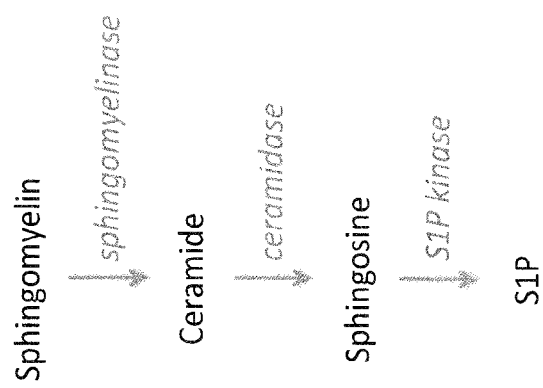
FIG. 3 illustrates a pathway for generation of Sphingosine-1-phosphate (S1P).
Figure 4:
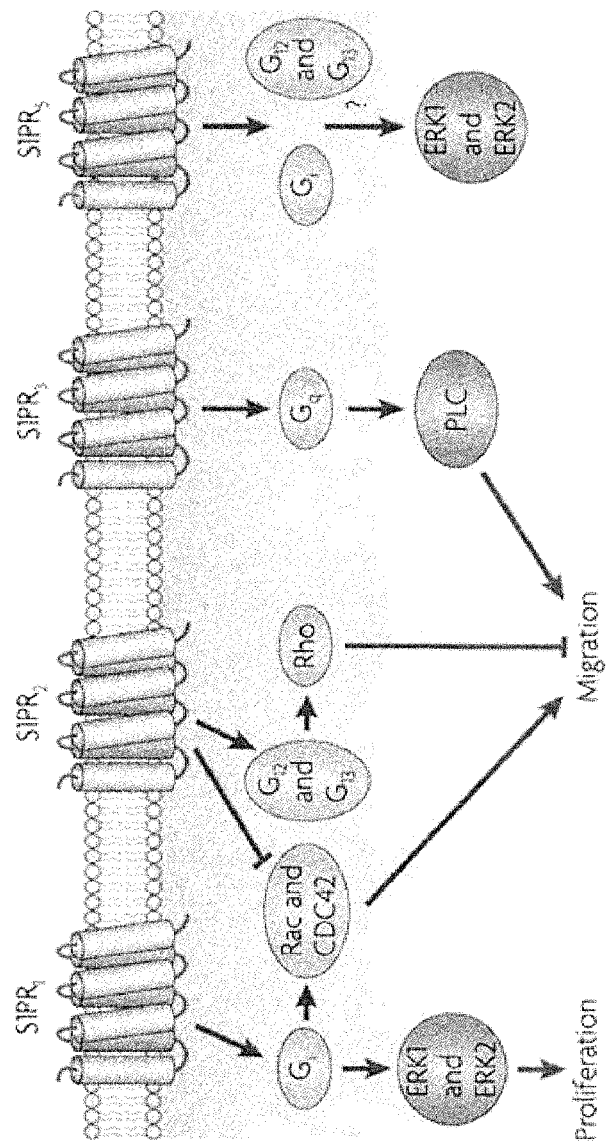
FIG. 4 illustrates sphingosine-1-P receptor (S1PR) signaling pathways. S1PR1, 2, and 3 are found on vascular endothelial cells. S1PR1 and S1PR3 drive vascular migration while S1PR2 counteracts their action. To this extent, inhibition of S1PR2 (inhibiting an inhibitor of vascular migration) will result in restoration of normal retinal vascularization for the retinal vascular developmental disorder familial exudative vitreoretinopathy (FEVR). (Fig from Nat. Rev. Cancer 10, 489-503 (2010)).

Various embodiments of the disclosure are discussed in detail below. While specific implementations are discussed, it should be understood that this is done for illustration purposes only. All references cited within this disclosure are incorporated herein. A person skilled in the relevant art will recognize that other components and configurations may be used without parting from the spirit and scope of the disclosure.

Described are compositions and methods for treating retinal vascular disorders through the administration of therapeutically effective amounts of S1PR2 antagonists. The treatment regime, in a preferred embodiment, is geared towards the treatment of FEVR.

The S1PR2 antagonist may be a compound characterized by the following general formula (IX):

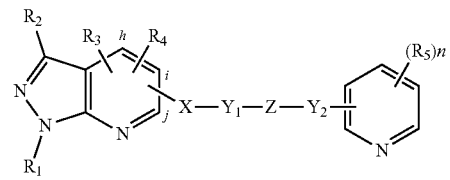

(IX)

wherein $R_1$ is $C_1$-$C_{12}$ alkyl;

$R_2$, $R_3$, and $R_4$ are each independently hydrogen, halogen, $C_1$-$C_6$ alkyl, $C_1$-$C_4$ alkoxy, $C_1$-$C_6$ perhaloalkyl, $C_1$-$C_4$ perhaloalkoxy, amino, mono- or di-$C_1$-$C_4$ alkylamino, $C_3$-$C_7$ cycloalkyl or $C_3$-$C_7$ cycloalkyloxy;

$R_3$ and $R_4$ can be positioned at h, i or j, but not simultaneously at the same position;

each instance of $R_5$ is independently selected from hydrogen, halogen, $C_1$-$C_6$ alkyl, $C_1$-$C_4$ alkoxy, $C_1$-$C_6$ perhaloalkyl, $C_1$-$C_4$ perhaloalkoxy, amino, mono- or di-$C_1$-$C_4$ alkylamino, $C_3$-$C_7$ cycloalkyl, and $C_3$-$C_7$ cycloalkyloxy;

n is 0, 1, 2, 3 or 4;

X is $NR_a$, $CH_2$, or —C(=O)—, wherein each instance of $R_a$ is independently selected from hydrogen and $C_1$-$C_3$ alkyl;

$Y_1$ and $Y_2$ are each independently selected from $NR_a$, $CH_2$, and O; and

Z is any geometric isomer of a group selected from one of the following:

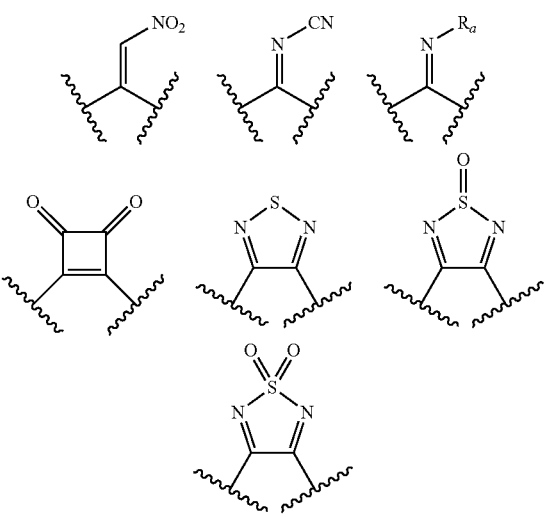

and —C(=O)—.

In one embodiment, X is not —NH— and/or $R_3$ and $R_4$ are not isopropyl. In a further embodiment, if Z is —C(=O)— and $R_3$ or $R_4$ is isopropyl, then X is not —NH—, and if Z is —C(=O)— and X is —NH—, then $R_3$ or $R_4$ are not isopropyl. In another embodiment, the S1PR2 antagonist may be one of Compounds 1-7. Compounds 1-7, shown below, are analogues of JTE-013 that inhibit S1PR2 and have improved stability compared to JTE-013, which are described in International Patent Application No. PCT/US2011/040637 (WO 2011/159864).

In certain embodiments, therefore, the S1PR2 antagonist for use in the disclosed compositions, methods and kits is selected from:

compound 1

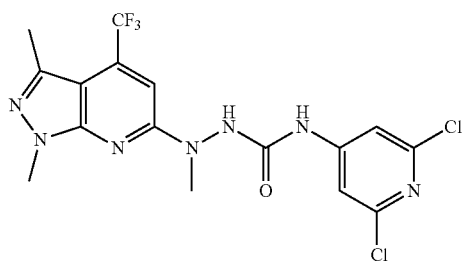

compound 2

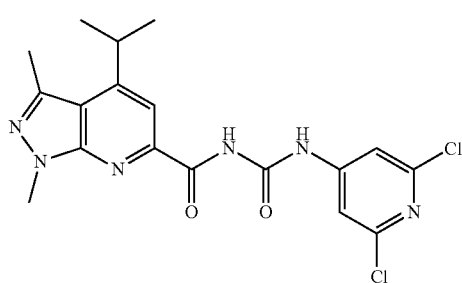

compound 3

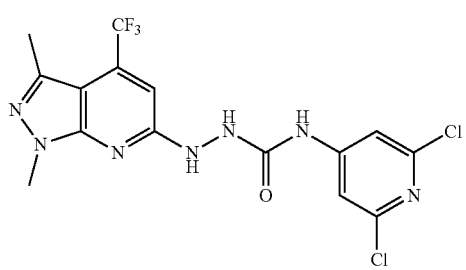

compound 4

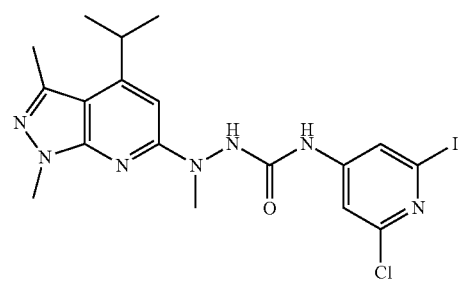

compound 5

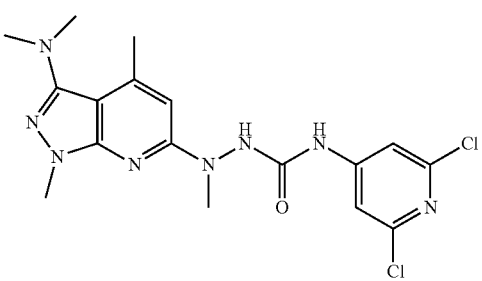

compound 6

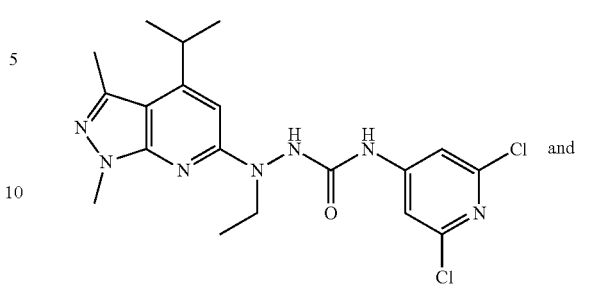

and compound 7

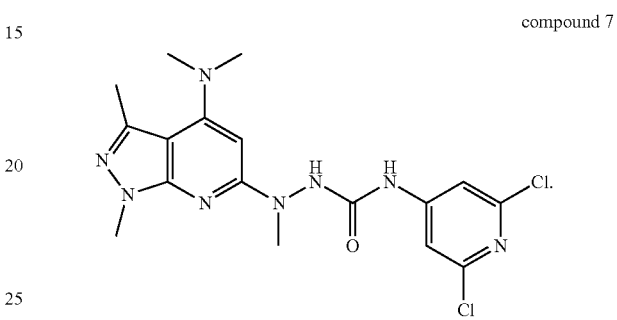

In another embodiment, the S1PR2 antagonist may be a compound of general formula IX, wherein Z is not —(C=O)—, and in particular, the S1PR2 antagonist may comprise a bioisosteric replacement of the urea linkage in JTE-013 or an analog thereof.

The S1PR2 antagonist may also be a compound characterized by the following general formula (X):

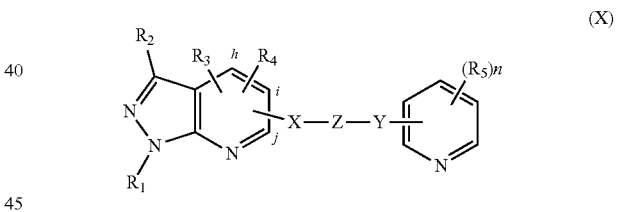

(X)

wherein, $R_1$ is $C_1$-$C_{12}$ alkyl;

$R_2$, $R_3$, and $R_4$ are each independently hydrogen, halogen, $C_1$-$C_6$ alkyl, $C_1$-$C_4$ alkoxy, $C_1$-$C_6$ perhaloalkyl, $C_1$-$C_4$ perhaloalkoxy, amino, mono- or di-$C_1$-$C_4$ alkylamino, $C_3$-$C_7$ cycloalkyl or $C_3$-$C_7$ cycloalkyloxy;

$R_3$ and $R_4$ can be positioned at h, i, or j, but not simultaneously at the same position;

each instance of $R_5$ is independently selected from hydrogen, halogen, $C_1$-$C_6$ alkyl, $C_1$-$C_4$ alkoxy, $C_1$-$C_6$ perhaloalkyl, $C_1$-$C_4$ perhaloalkoxy, amino, mono- or di-$C_1$-$C_4$ alkylamino, $C_3$-$C_7$ cycloalkyl, and $C_3$-$C_7$ cycloalkyloxy;

n is 0, 1, 2, 3 or 4;

X and Y are each independently selected from $NR_a$, O, and $CH_2$, wherein each instance of $R_a$ is independently selected from hydrogen and $C_1$-$C_3$ alkyl;

and Z is any geometric isomer of a group selected from one of the following:

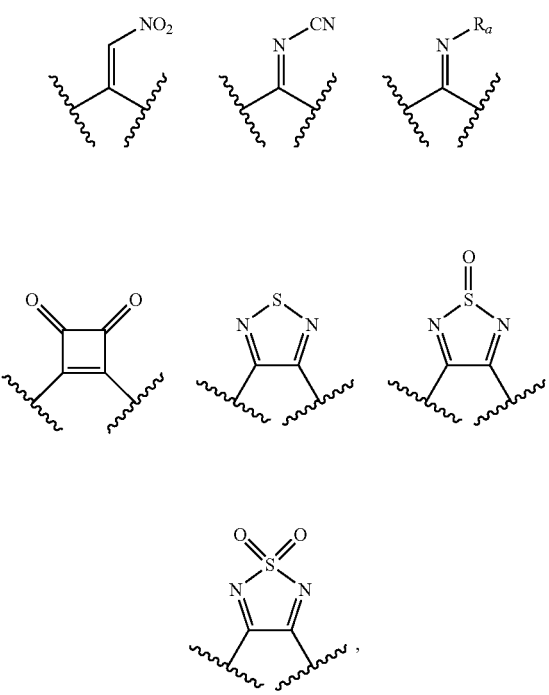

and —C(=O)—.

In one embodiment, Z is not —C(=O)—. In particular, the S1PR2 antagonist for use in the disclosed compositions, methods and kits may be selected from one of Compounds 8 and 9, shown below.

compound 8

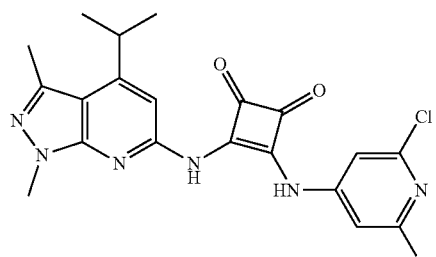

compound 9

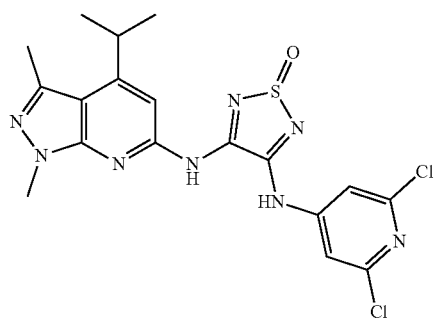

According to some embodiments, the therapeutically effective amount of the S1PR2 antagonist has a formula selected from the following compounds: 2-[3-[(4-amino-2-methylpyrimidin-5-yl)methyl]-4-methyl-1,3-thiazol-3-ium-5-yl]ethyl hydrogen phosphate (PubChem ID No. 3382778), [(2S,3R)-2-azaniumyl-3-hydroxyoctadecyl] hydrogen phosphate (PubChem No. 44317142), (also as 520 and 644260); (5aR,6R,9S,9aS)-2-carboxy-6-hydroxy-6-methyl-3-pentyl-9-prop-1-en-2-yl-7,8,9,9a-tetrahydro-5aH-dibenzofuran-1-olate (PubChem ID No. 54736865), 2-(1-amino-2-hydroxypropyl)-N-decyl-1,3-oxazole-4-carboxamide (PubChem ID No. 3866342), [(2S,3R)-2-azaniumyl-3-hydroxyheptadecyl] hydrogen phosphate (PubChem ID. No. 46891770 (also as 3247041), [(1S,2S,3S,4R,5R)-3-hydroxy-4-(4-methylpiperazin-4-ium-1-yl)-6,8-dioxabicyclo[3.2.1]octan-2-yl]-(quinolin-3-ylmethyl)azanium (PubChem ID No. 51624406), 5-[(2E)-2-(3-carboxy-4-oxocyclohexa-2,5-dien-1-ylidene)hydrazinyl]-2-sulfooxybenzoic acid (PubChem ID. No. 9578291); 5,7-dihydroxy-3-[3-hydroxy-4-methoxy-5-(3-methylbut-2-enyl)phenyl]-2,3-dihydrochromen-4-one (Pubchem ID No. 9864156), 5-hydroxy-2-(1-hydroxy-11-phenylundecylidene)cyclohexane-1,3-dione (PubChem ID No. 365015); 3-[(3S)-3-azaniumyl-3-(2-hydroxynaphthalen-1-yl)propanoyl]-1-methyl-4-oxoquinolin-2-olate (PubChem ID No. 28094480), 2-[(E)-2-anthracen-9-yl-1-cyanoethenyl]-6-methylquinazolin-4-olate (PubChem ID No. 40592676), [(E,2S,3R)-2-azaniumyl-3-hydroxyoctadec-4-enyl] hydrogen phosphate (PubChem ID No. 10883396), 2-chloro-3,6-dihydroxy-5-undecylcyclohexa-2,5-diene-1,4-dione (PubChem ID No. 342302), (2S)-2-amino-2-(9H-fluoren-9-ylmethoxycarbonyl)-3-hydroxy-4-methylpentanoic acid (PubChem ID No. 56923845), (5aR,6S,9S,9aS)-2-carboxy-6-hydroxy-6-methyl-3-pentyl-9-prop-1-en-2-yl-7,8,9,9a-tetrahydro-5aH-dibenzofuran-1-olate (PubChem ID. No. 54734912); [(1S,2S,3S,4R,5R)-3-hydroxy-4-(4-methylphenyl)sulfonyloxy-6,8-dioxabicyclo[3.2.1]octan-2-yl]-propan-2-ylazanium (PubChem ID. No. 18390590), 2-amino-2-(9H-fluoren-9-yl methoxycarbonyl)-3-hydroxy-3-methylbutanoic acid (PubChem ID No. 56923928), [(1S,2S,3R,4R,5R)-3-hydroxy-4-(2-methoxyethylamino)-6,8-dioxabicyclo[3.2.1]octan-2-yl]-[(4-phenylphenyl) methyl]azaniumn (PubChem ID No. 51508548), (2-hydroxyphenyl)methyl-[(1S,2S,3S,4R,5R)-3-hydroxy-4-phenylsulfanyl-6,8-dioxabicyclo[3.2.1]octan-2-yl]azanium (PubChem ID. No. 28960354), [(1S,2S,3S,4R,5R)-3-hydroxy-4-(4-methylpiperazin-4-ium-1-yl)-6,8-dioxabicyclo[3.2.1]octan-2-yl]-[(2-hydroxyphenyl)methyl]azanium (PubChem ID. No. 51624683), (13-methyl-17-oxo-9,11,12,14,15,16-hexahydro-6H-cyclopenta[a]phenanthren-3-yl) hydrogen sulfate (PubChem ID No. 27993).

Suitable compounds for use in the compositions, methods and kits disclosed herein are compounds that antagonize S1PR2. Non-limiting examples of S1PR2 antagonists include those known and described in the art (see, for example, International Patent Applications Nos. PCT/US2013/033289 (WO 2013/148460) and PCT/US2014/011033 (WO 2014/158302); U.S. Pat. No. 8,703,797; WO 2011/159864; WO 2008/154470; and WO 2001/098301), as well as those compounds identified herein that interact with the S1PR2 binding pocket (see, for example, FIGS. 8, 9 and 11). Analogues of these compounds that antagonize S1PR2 are also contemplated for use in the disclosed compositions, methods and kits in certain embodiments. Antagonism of S1PR2 can be readily tested using methods such as those described herein and known in the art.

According to some embodiments, the S1PR2 antagonist can be 1-(2,6-dichloro-4-pyridyl)-3-[(4-isopropyl-1,3-dimethyl-pyrazolo[3,4-b]pyridin-6-yl)amino]urea, with the following chemical structure:

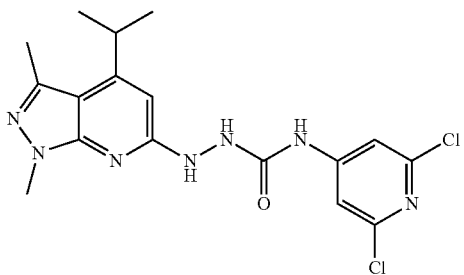 [SMILES: Cc1nn(C)c2nc(NNC(=O)Nc3cc(Cl)nc(Cl)c3)cc(C(C)C)c12]

According to some embodiments, the S1PR2 antagonist can be a compound characterized by the following general formula (I):

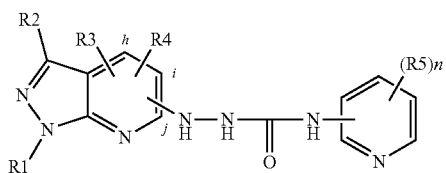

(I)

wherein:

R$_1$ is a C$_1$-C$_{12}$ alkyl, and R$_2$, R$_3$ and R$_4$ are each independently hydrogen, halogen, C1-C$_6$ alkyl, C$_1$-C$_6$ perhaloalkyi, C1-C4 perhaloalkoxy, amino, mono- or di C$_1$-C4 alkylamino, C$_3$-C$_7$ cycloalkyl or C3-C7 cycloalkoxy, and R$_3$ and R$_4$ are optionally positioned at h, i, or j, but not simultaneously at the same position, and R$_5$ is , halogen, C$_1$-C$_6$ alkyl, C$_1$-C$_6$ perhaloalkyi, C$_1$-C4 perhaloalkoxy, amino, mono- or di C$_1$-C4 alkylamino, C$_3$-C$_7$ cycloalkyl or C$_3$-C$_7$ cycloalkoxy, and—n is 0, 1 , 2, 3 or 4.

According to some embodiments, the S1PR2 antagonist can be a compound characterized by the general formula a general formula II wherein:

X is NR$^a$R$^b$, SR$^b$, F, CI, Br or I, and

R$^1$ is H or R$^b$

R$^2$ is H, F, CI, Br, I, or R$^b$

R$^a$ is H or R$^b$, and R$^b$ is branched or linear alkyl having 1 to 12 carbon atoms, wherein one or more, preferably 1 to 7 hydrogen atoms may be replaced by F, CI, Br, I, OR$^a$, COOR$^3$, CN, N(R$^a$)$_2$ and wherein one or more, preferably 1 to 7 non-adjacent CH$_2$-group may be replaced by O, NR$^a$, S or SO$_2$, and/or by —CH═CH— groups, or is cycloalkyl or cycloalkylalkylene having 3 to 7 ring carbon atoms, and W is C═O, C═S, SO$_2$ or SO, and Q is NR3, —O— or —S—, and R is hydrogen, R$^b$, Ar or Het, and Ar is a monocyclic or bicyclic, saturated, unsaturated or aromatic carbocyclic ring having 6 to 14 carbon atoms which may be unsubstituted, mono-, di-, or tri-substituted by F, CI, Br, I, R$^b$, OR3, —[C(R$^3$)$_2$]n-OR$^3$, N(R$^3$)$_2$, —[C(R$^3$)2]n-N(R$^3$)$_2$, NO$_2$, CN, COOR$^3$, CF$_3$, OCF$_3$, CON(R$^3$), NR$^3$COA, NR$^3$CON(R$^3$)$_2$, —[C(R$^3$)$_2$]n-Het, —[C(R$^3$)$_2$]n-Nr, —[C(R$^3$)$_2$]n-cycloalkyl, —[C(R$^3$)$_2$]n-CON(R$^3$)$_2$, —[(R$^3$)$_2$]n-COOR$^3$, —[C(R$^3$)$_2$]n-NR$^3$—[C(R$^3$)$_2$]n-CO$_2$R$^3$; —[C(R$^3$)$_2$]n-NR$^3$—[C(R$^3$)$_2$]n-OR$^3$, —SO$_2$-[C(R$^3$)2]n-CO$_2$R$^3$, —SO$_2$—N(R$^3$)$_2$]n-[CO$_2$R$^3$, —[C(R$^3$)$_2$]N—SO$_2$-[C(R$^3$)]n-CO$_2$R3, -S02[C (R$^3$)$_2$]n-OR$^3$, —SO$_2$N(R$^3$)$_2$—[C(R$^3$)$_2$]n-OR$^3$, —[C(R$^3$)$_2$]N—SO$_2$-[C(R$^3$)$_2$]n-OR$^3$, NR$^3$CON(R$^3$)$_2$, NR$^3$SO$_2$R$^b$, COR$^3$, SO$_2$N(R$^3$)$_2$, S02N(R3)Rb, SORb, SONR$^3$R$^b$, SO$_2$R$^b$, and/or -0[C(R$^3$)$_2$]n-COOR$^3$ and Het is a monocyclic or bicyclic, saturated, unsaturated or aromatic heterocyclic ring having 1 to 4 N, O and/or S which may be unsubstituted, mono-, di-, or trisubstituted by F, CI, Br, I, R$^b$, OR3, —[C(R$^3$)$_2$]n-OR$^3$, N(R$^3$)$_2$, —[C(R$^3$)2]n-N(R$^3$)$_2$, NO$_2$, CN, COOR$^3$, CF$_3$, OCF$_3$, CON(R$^3$), NR$^3$COA, NR$^3$CON(R$^3$)$_2$, —[C(R$^3$)$_2$]n-Het, —[C(R$^3$)$_2$]n-Ar, —[C(R$^3$)$_2$]n-cycloalkyl, —[C(R$^3$)$_2$]n-CON(R$^3$)$_2$, —[(R$^3$)$_2$]n-COOR$^3$, —[C(R$^3$)$_2$]n-NR$^3$—[C(R$^3$)$_2$]n-CO$_2$R$^3$; —[C(R$^3$)$_2$]n-NR$^3$—[C(R$^3$)$_2$]n-OR$^3$, —SO$_2$-[C(R$^3$)2]n-C O$_2$R$^3$, —SO$_2$—N (R$^3$)$_2$]n-[CO$_2$R$^3$, —[C(R$^3$)$_2$]N—SO$_2$—[C(R$^3$)]n-CO$_2$R3, -S02[C (R$^3$)$_2$]n-OR$^3$, —SO$_2$N(R$^3$)$_2$—[C(R$^3$)$_2$]n-OR$^3$, —[C(R$^3$)$_2$]N—SO$_2$-[C(R$^3$)$_2$]n-OR$^3$, NR$^3$CON(R$^3$)$_2$, NR$^3$SO$_2$R$^b$, COR$^3$, SO$_2$N(R$^3$)$_2$, S02N(R3)Rb, SORb, SONR$^3$R$^b$, SO$_2$R$^b$, and/or -0[C(R$^3$)$_2$]n-COOR$^3$, and R$^1$ is H or R$^b$, and R$^2$ is H, F, CI, Br, I, or R$^b$, and R$^3$ is is H or R$^b$, and n is 0, 1, 2, 3, 4, 5, 6, 7 or 8;

In certain embodiments, the compound may be a compound selected from:

2-[1-[2-(5-chloro-2,4-dimethoxy-anilino)-2-oxo-ethyl]-2,4-dioxo-quinazolin-3-yl]acetic acid; —N-(5-chloro-2,4-dimethoxy-phenyl)-2-[2,4-dioxo-3-[2-oxo-2-[2-(3-p ridyl) ethylamino]ethyl]quinazolin-1-yl]; 2-[4-[1-[2-(5-chloro-2, 4-dimethoxy-anilino)-2-oxo-ethyl]-2,4-dioxo-quinazolin-3-yl]phenyl]-N-phenethyl-acetamide; 4-[6-chloro-1-[2-(3-chloro-4-ethoxy-phenyl)-2-oxo-ethyl]-2,4-dioxo-quinazolin-3-yl]-N-cyclopentyl-butanamide; N-(5-chloro-2, 4-dimethoxy-phenyl)-2-[2,4-dioxo-3-[2-(phenethylamino) ethyl]quinazolin-1-yl ]acetamide; -tert-butyl 2-[1-[2-(5-chloro-2,4-dimethoxy-anilino)-2-oxo-ethyl]-2,4-dioxo-quinazolin-3-yl]acetate; -tert-butyl N-[2-[1-[2-(5-chloro-2,4-dimethoxy-anilino)-2-oxo-ethyl]-2,4-dioxo-quinazolin-3-yl]ethyl]carbamate; -2-[1-[2-(5-chloro-2,4-dimethoxy-anilino)-2-oxo-ethyl]-2,4-dioxo-pyrido[3,2-d]pyrimidin-3-yl]acetic acid; -2-[1-[2-(5-chloro-2,4-dimethoxy-anilino)-2-oxo-ethyl]-2-oxo-4H-quinazolin-3-yl acetic acid; N-(5-chloro-2,4-dimethoxy-phenyl)-2-[3-(3-methoxybenzoyl)-7-methyl-4-4a,8a-dihydro-1,8-naphthyridin-1-yl]acetamide; 2-[1-[2-[(2,6-dichloro-4-pyridyl)amino]-2-oxo-ethyl]-5-methyl-2,4-dioxo-quinazolin-3-l]acetic acid; 4-methyl-8-(2, 4,6-trimethylanilino)-2H-phthalazin-1-one; 4-methyl-8-(2, 4,6-trimethylanilino)-2H-isoquinolin-1-one; 8-(2,6-dimethylanilino)-2H-isoquinolin-1-one; 8-(4-fluoro-2,6-dimethyl-anilino)-4-methyl-2H-phthalazin-1-one; -4-ethyl-8-(2,4,6-trimethylanilino)-2H-phthalazin-1-one; 4-isopropyl-8-(2,4,6-trimethylanilino)-2H-phthalazin-1-one; -4-(2-hydroxyethyl)-8-(2,4,6-trimethylanilino)-2H-phthalazin-1-one; -8-(2,6-diethyl-4-fluro-anilino)-4-methyl-2H-phthalazin-1-one; 8-(4-chloro-2,6-dimethyl-anilino)-4-methyl-2H-phthalazin-1-one; -4-ethyl-8-(4-fluoro-2,6-dimethyl-anilino)-2H-phthalazin-1-one; -5-(2-propylpyrazol-3yl) 2-2(2,4,6-trimethylanilino)benzamide; -5-methoxy-2-(2,4,6-trimethylanilino) benzamide; 5-chloro-2-(2,4,6-trimethylanilino)benzamide.

In certain embodiments, the compound may be a compound selected from:

2-amino-2-[2-(4-octylphenyl)ethyl]propane-1,3-diol;

5-[[3-chloro-4-(2,3 dihydroxypropoxy)phenyl]methyl]-3-(o-tolyl)-2-(propylamino) thiazolidin-4-one;

2-amino-2-[2-[4-(3-benzyloxyphenyl)sulfanyl-2-chlorophenyl]ethyl]propane-1,3-diol;

1-[5-[(3R)-3-amino-4-hydroxy-3-methyl-butyl]-1-methyl-pyrrol-2-yl]-4-(p-tolyl)butan-1-one;

3-amino-4-(3-octylanilino)-4-oxo-butyl]phosphonic acid; and

5-[4-phenyl-5-(trifluoromethyl)-2-thienyl]-3-[3-(trifluoromethyl)oxadiazole.

In another embodiment, the S1PR2 antagonist can be a compound with the general formula (III):

$$Ar^2—X\ Y\ Z—W—Ar^1 \quad \text{(formula III)}$$

Wherein:
$Ar^1$ is optionally substituted heterocycle or aromatic heterocycle;
$Ar^2$ is optionally substituted heterocycle or aromatic heterocycle;
W is $NR^a$—, O, or —$CH_2$—, wherein $R^a$ is hydrogen or $C_1$-$C_3$ alkyl;
Z is —C(=O)—, —C(=S)—, O, —$CH_2$—, =N—, or =CH—;
Y is —$NR^a$—, —C(=O)—, —N=, —CH=, =N—, or =CH—; and
X is —$NR^a$—, —N=, —CH=, or —$CH_2$—.

In another embodiment, the S1PR2 antagonist can be a compound with the general formula IV:

(Formula IV)

wherein
$Ar^1$ is aromatic heterocycle;
W is $NR^a$—, O, or —$CH_2$—, wherein $R^a$ is hydrogen or $C_1$-$C_3$ alkyl;
Z is —C(=O)—, —C(=S)—, O, —$CH_2$—, =N—, or =CH—;
Y is —$NR^a$—, —C(=O)—, —N=, —CH=, =N—, or =CH—; and
X is —$NR^a$—, —N=, —CH=, or —$CH_2$—;
$R^1$ is $C_1$-$C_{12}$ alkyl;
$R^2$, $R^3$, and $R^4$ are each independently hydrogen, halogen, $C_1$-$C_6$ alkyl, $C_1$-$C_4$ alkoxy, $C_1$-$C_6$ perhaloalkyl, $C_1$-$C_4$ perhaloalkoxy, amino, mono- or di-$C_1$-$C_4$ alkylamino, $C_3$-$C_7$ cycloalkyl, or $C_3$-$C_7$ cycloalkyloxy;
$R^3$ and $R^4$ can be positioned at h, i, or j, but not simultaneously at the same position; and
$X^2$ is N or —$CR^b$—wherein $R^b$ is hydrogen, halogen, $C_1$-$C_6$ alkyl, $C_1$-$C_4$ alkoxy, $C_1$-$C_6$ perhaloalkyl, $C_1$-$C_4$ perhaloalkoxy, amino, mono- or di-$C_1$-$C_4$ alkylamino, $C_3$-$C_7$ cycloalkyl, or $C_3$-$C_7$ cycloalkyloxy.

In another embodiment, the S1PR2 antagonist can be a compound with the general formula V:

(Formula V)

wherein
$R^1$ is $C_1$-$C_{12}$ alkyl;
$R^2$, $R^3$, and $R^4$ are each independently hydrogen, halogen, $C_1$-$C_6$ alkyl, $C_1$-$C_4$ alkoxy, $C_1$-$C_6$ perhaloalkyl, $C_1$-$C_4$ perhaloalkoxy, amino, mono- or di-$C_1$-$C_4$ alkylamino, $C_3$-$C_7$ cycloalkyl, or $C_3$-$C_7$ cycloalkyloxy;
$R^3$ and $R^4$ can be positioned at h, i, or j, but not simultaneously at the same position;
each instance of $R^5$ is halogen, $C_1$-$C_6$ alkyl, $C_1$-$C_4$ alkoxy, $C_1$-$C_6$ perhaloalkyl, $C_1$-$C_4$ perhaloalkoxy, amino, mono- or di-$C_1$-$C_4$ alkylamino, $C_3$-$C_7$ cycloalkyl, or $C_3$-$C_7$ cycloalkyloxy; and
n is 0, 1, 2, 3, or 4.

In certain embodiments, in compounds of general formula (III):
$R^1$ is $C_1$-$C_3$ alkyl;
$R^2$ is $C_1$-$C_3$ alkyl;
$R^3$ is at position h, and is $C_1$-$C_6$ alkyl;
$R^4$ is hydrogen;
$R^5$ is halogen, and
n is 2.

Additional JTE-013 analogues of general formula (VI), (VII) or (VIII), shown below, having S1PR2 antagonist activity are described in U.S. Pat. No. 8,703,797, the contents of which are incorporated herein by reference.

In another embodiment, the S1PR2 antagonist can be a compound with the general formula VI:

(Formula VI)

wherein:
A is a direct bond or (CR) and B, C and D are independently selected from the group consisting of (CR) and N, wherein R is H or alkyl, provided however, not all, of B, C and D are N and, when A is a direct bond, D is (CR);
$R^3$ is selected from the group consisting of alkyl;
X is selected from the group consisting of O, $NR^4$ and $CR^4R^5$, wherein $R^4$ and $R^5$ are independently selected from the group consisting of H and alkyl;
Y is selected from the group consisting of O or S; and
Z is a substituted aryl ring.

In another embodiment, the S1PR2 antagonist can be a compound with the general formula VII:

(Formula VII)

wherein:
$R^1$ and $R^2$ are independently selected from the group consisting of H and alkyl, methoxy, hydroxyl, halogen, nitrile, and trifluoromethyl;
$R^3$ is independently selected from the group consisting of alkyl, methoxy, hydroxyl, halogen, nitrile, and trifluoromethyl;

D is CR or N;

R is H or alkyl;

X is O, NR$^4$, CR$^4$R$^5$, where R$^4$ and R$^5$ are independently selected from the group consisting of H and alkyl, e.g. lower alkyl and may have from 1 to 10 carbons, and may be cyclic or branched chain alkyl having 3 to 10 carbons, methoxy, hydroxyl, F, Br, I, nitrile, and trifluoromethyl;

Y is O or S,

Z is a substituted aryl ring, having the following structure:

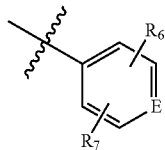

wherein R$^6$ and R$^7$ are independently selected from the group consisting of alkyl and may include from 1 to 10 carbons, and may be cyclic or branched chain alkyl having 3 to 10 carbons, methoxy, hydroxyl, halogen, nitrile, and trifluoromethyl; and E is N or CR;

or, wherein:

R$^1$, R$^2$ and R$^3$ are independently H, halogen, methyl, or isopropyl;

X is NR$^4$;

R$^4$ is H;

Y is O;

R$^6$ and R$^7$ are independently H or chloro;

E is N or CR; and

R is H.

In another embodiment, the S1PR2 antagonist can be a small molecule selected from the group consisting of: N-(3,5-dichlorophenyl)-2-(4-methyl-1,8-naphthyridin-2-yl) hydrazinecarboxamide; N-(3,5-dichlorophenyl)-2-(4-isopropyl-1,8-naphthyridin-2-yl) hydrazinecarboxamide; N-(3,5-dichlorophenyl)-2-(4-isopropyl-5,8-dimethylquinolin-2-yl) hydrazinecarboxamide; N-(3,5-dichlorophenyl)-2-(4-isopropylquinolin-2-yl) hydrazinecarboxamide; N-(2,6-dichloropyridin-4-yl)-2-(4,8-dimethylquinolin-2-yl) hydrazinecarboxamide; N-(3,5-dichlorophenyl)-2-(4,8-dimethylquinolin-2-yl) hydrazinecarboxamide; N-(2,6-dichloropyridin-4-yl)-2-(4-methylquinolin-2-yl) hydrazinecarboxamide; and N-(3,5-dichlorophenyl)-2-(4,5,8-trimethylquinolin-2-yl) hydrazinecarboxamide.

In another embodiment, the S1PR2 antagonist can be a compound with the general formula VIII:

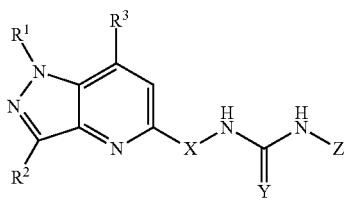

(Formula VIII)

wherein:

R$^1$ R$^2$ are independently selected from the group consisting of H and alkyl, methoxy, hydroxyl, halogen, nitrile, and trifluoromethyl;

R$^3$ is independently selected from the group consisting of alkyl, methoxy, hydroxyl, halogen, nitrile, and trifluoromethyl;

X is O, NR$^4$, CR$^4$R$^5$, where R$^4$ and R$^5$ are independently selected from the group consisting of H and alkyl, e.g. lower alkyl and may have from 1 to 10 carbons, and may be cyclic or branched chain alkyl having 3 to 10 carbons, methoxy, hydroxyl, F, Br, I, nitrile, and trifluoromethyl;

Y is O or S;

R is H, methoxy or alkyl;

Z is a substituted aryl ring, having the following structure:

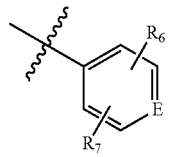

wherein R$^6$ and R$^7$ are independently selected from the group consisting of alkyl and may include from 1 to 10 carbons, and may be cyclic or branched chain alkyl having 3 to 10 carbons, methoxy, ethoxy, propoxy, butoxy, hydroxyl, halogen, nitrile, and trifluoromethyl; and E is N or CR;

or wherein:

R$^1$, R$^2$ and R$^3$ are independently methyl or isopropyl;

X is NR$^4$ or CR$^4$R$^5$;

R$^4$ is H;

R$^5$ is H;

Y is O;

R$^6$ and R$^7$ are independently selected from the group consisting of alkyl and may include from 1 to 5 carbons, methoxy, ethoxy, propoxy, butoxy, chloro and trifluoromethyl;

E is N or CR; and

R is H or methoxy.

In another embodiment, the S1PR2 antagonist can be a small molecule selected from the group consisting of: N-(3,5-dichlorophenyl)-2-(7-isopropyl-1,3-dimethyl-1H-pyrazolo[4,3-b]pyridin-5-yl)hydrazinecarboxamide; 1-(2,6-dichloropyridin-4-yl)-3-((7-isopropyl-1,3-dimethyl-1H-pyrazolo[4,3-b]pyridin-5-yl)methyl)urea; N-(2-butyl-6-chloropyridin-4-yl)-2-(7-isopropyl-1,3-dimethyl-1H-pyrazolo[4,3-b]pyridin-5-yl)hydrazinecarboxamide; N-(2-chloro-6-ethoxypyridin-4-yl)-2-(7-isopropyl-1,3-dimethyl-1H-pyrazolo[4,3-b]pyridin-5-yl) hydrazinecarboxamide; 1-(3,5-dichlorophenyl)-3-((1,3,7-trimethyl-1H-pyrazolo[4,3-b]pyridin-5-yl)methyl)urea; N-(2,6-dichloropyridin-4-yl)-2-(7-isopropyl-1,3-dimethyl-1H-pyrazolo[4,3-b]pyridin-5-yl)hydrazinecarboxamide; N-(3,5-bis(trifluoromethyl)phenyl)-2-(7-isopropyl-1,3-dimethyl-1H-pyrazolo[4,3-b]pyridin-5-yl)hydrazinecarboxamide; N-(3-chloro-5-methoxypyridin-4-yl)-2-(7-isopropyl-1,3-dimethyl-1H-pyrazolo[4,3-b]pyridin-5-yl) hydrazinecarboxamide; 1-(2,6-dichlorophenyl)-3-((7-isopropyl-1,3-dimethyl-1H-pyrazolo[4,3-b]pyridin-5-yl)methyl)urea; 1-(2-chloro-6-methoxypyridin-4-yl)-3-((7-isopropyl-1,3-dimethyl-1H-pyrazolo[4,3-b]pyridin-5-yl)methyl)urea; N-(2-chloro-6-propylpyridin-4-yl)-2-(7-isopropyl-1,3-dimethyl-1H-pyrazolo[4,3-b]pyridin-5-yl)hydrazinecarboxamide; 1-(2-chloro-6-propylpyridin-4-yl)-3-((7-isopropyl-1,3-dimethyl-1H-pyrazolo[4,3-b]pyridin-5-yl)methyl)urea; 1-(2-chloro-6 ethoxypyridin-4-yl)-3-((7-isopropyl-1,3-dimethyl-1H-pyrazolo[4,3-b]pyridin-5-yl) methyl)urea; 1-(2-chloro-6-propoxypyridin-4-yl)-3-((7-isopropyl-1,3-dimethyl-1H-pyrazolo[4,3-b]pyridin-5-yl)methyl)urea; N-(2-chloro-6-propoxypyridin-4-yl)-2-(7-isopropyl-1,3-dimethyl-1H- pyrazolo[4,3-b]pyridin-5-yl)hydrazinecarboxamide; N-(2-butoxy-6-chloropyridin-4-yl)-2-(7-isopropyl-1,3-dimethyl-1H-pyrazolo[4,3-b]pyridin-5-yl) hydrazinecarboxamide; 1-(2-butoxy-6-chloropyridin-4-yl)-3-((7-isopropyl-1,3-dimethyl-1H-pyrazolo[4,3-b]pyridin-5-yl)methyl)urea; N-(2-ethoxypyridin-4-yl)-2-(7-isopropyl-1,3-dimethyl-1H-pyrazolo [4,3-b]pyridin-5-yl)hydrazinecarboxamide; and N-(5-chloro-2,4-dimethoxyphenyl)-2-(7-isopropyl-1,3-dimethyl-1H-pyrazolo[4,3-b]pyridin-5-yl)hydrazinecarboxamide.

2. (Z)-3-((2,6-dichloropyridin-4-yl)amino)-3-(((4-isopropyl-1,3-dimethyl-1H-pyrazolo[3,4-b]pyridin-6-yl)methyl)amino)acrylonitrile and Analogs Thereof The S1PR2 antagonist may be (Z)-3-((2,6-dichloropyridin-4-yl)amino)-3-(((4-isopropyl-1,3-dimethyl-1H-pyrazolo[3,4-b]pyridin-6-yl)methyl)amino)acrylonitrile (referred to herein as "Compound Z") or an analog thereof, or a pharmaceutically acceptable salt of the foregoing. Compound Z has the following structure:

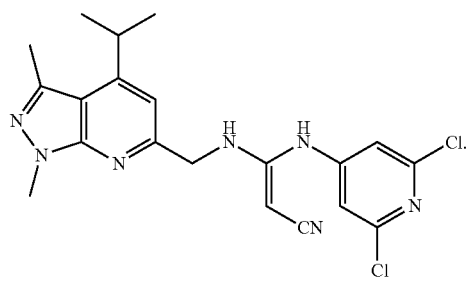 [SMILES: Cc1nn(C)c2nc(CN/C(=C/C#N)Nc3cc(Cl)nc(Cl)c3)cc(C(C)C)c12]

The analog of Compound Z may be a compound of formula (XI):

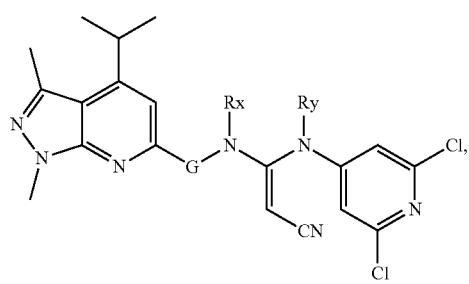

(XI)

wherein:
G is $CR_{10}$ or $NR_{11}$, wherein $R_{10}$ and $R_{11}$ are each independently selected from the group consisting of H, $C_1$-$C_4$ alkyl, and benzyl;
$R_x$ and $R_y$ are independently selected from the group consisting of H, $C_1$-$C_4$ alkyl, and benzyl; or $R_x$ and $R_y$ are joined to form a 5- or 6-membered heterocycloalkyl ring; and,
the cyano group is in the (Z) or (E) configuration.

In one embodiment, the analog of Compound Z is a compound of formula (XI), wherein:
G is $CR_{10}$ and $R_{10}$ is H; and,
$R_y$ is H.

In particular for this embodiment, the compound may be selected from the following:

(E)-3-((2,6-dichloropyridin-4-yl)amino)-3-(((4-isopropyl-1,3-dimethyl-1H-pyrazolo[3,4-b]pyridin-6-yl)methyl)(methyl)amino)acrylonitrile:

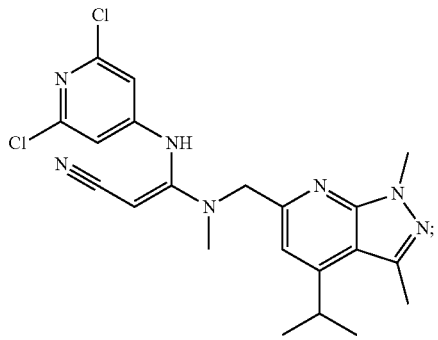 [SMILES: Cc1nn(C)c2nc(CN(C)/C(=C/C#N)Nc3cc(Cl)nc(Cl)c3)cc(C(C)C)c12]

(E)-3-((2,6-dichloropyridin-4-yl)amino)-3-(ethyl((4-isopropyl-1,3-dimethyl-1H-pyrazolo[3,4-b]pyridin-6-yl)methyl)amino)acrylonitrile:

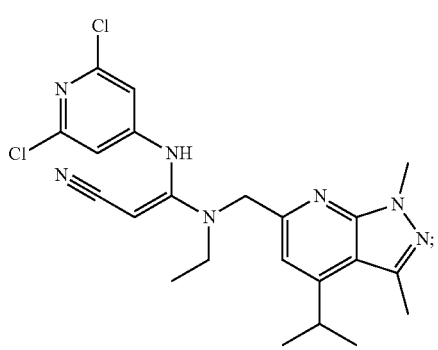 [SMILES: CCN(Cc1cc(C(C)C)c2c(C)nn(C)c2n1)/C(=C/C#N)Nc1cc(Cl)nc(Cl)c1]

(E)-3-((2,6-dichloropyridin-4-yl)amino)-3-(((4-isopropyl-1,3-dimethyl-1H-pyrazolo[3,4-b]pyridin-6-yl)methyl)(propyl)amino)acrylonitrile:

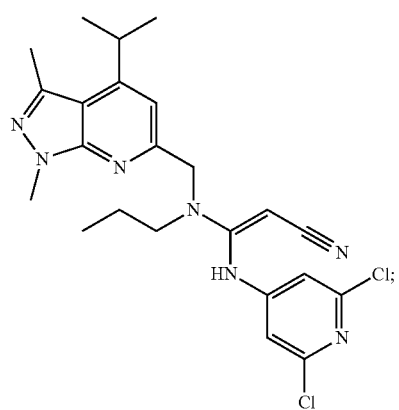 [SMILES: CCCN(Cc1cc(C(C)C)c2c(C)nn(C)c2n1)/C(=C/C#N)Nc1cc(Cl)nc(Cl)c1]

(E)-3-(butyl((4-isopropyl-1,3-dimethyl-1H-pyrazolo[3,4-b]pyridin-6-yl)methyl)amino)-3-((2,6-dichloropyridin-4-yl)amino)acrylonitrile:

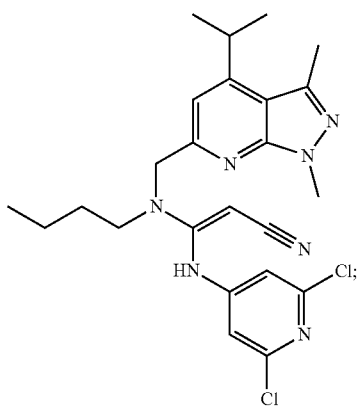 [SMILES: CCCCN(Cc1cc(C(C)C)c2c(C)nn(C)c2n1)/C(=C/C#N)Nc1cc(Cl)nc(Cl)c1]

(E)-3-((2,6-dichloropyridin-4-yl)amino)-3-(isopropyl((4-isopropyl-1,3-dimethyl-1H-pyrazolo[3,4-b]pyridin-6-yl)methyl)amino)acrylonitrile:

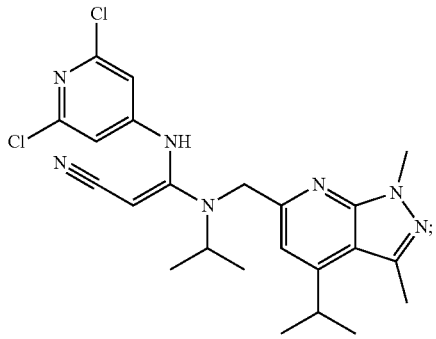 [SMILES: Cc1nn(C)c2nc(CN(/C(=C/C#N)Nc3cc(Cl)nc(Cl)c3)C(C)C)cc(C(C)C)c12]

(E)-3-(benzyl((4-isopropyl-1,3-dimethyl-1H-pyrazolo[3,4-b]pyridin-6-yl)methyl)amino)-3-((2,6-dichloropyridin-4-yl)amino)acrylonitrile:

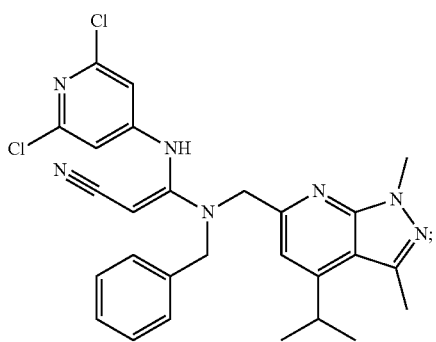 [SMILES: Cc1nn(C)c2nc(CN(Cc3ccccc3)/C(=C/C#N)Nc3cc(Cl)nc(Cl)c3)cc(C(C)C)c12]

and, a structural enantiomer of the foregoing, wherein the cyano group is in the (Z) form.

In another embodiment, the analog of Compound Z is a compound of formula (XI), wherein:

G is $CR_{10}$ and $R_{10}$ is H; and, $R_x$ is H.

In particular for this embodiment, the compound may be selected from the following:

(Z)-3-((2,6-dichloropyridin-4-yl)(methyl)amino)-3-(((4-isopropyl-1,3-dimethyl-1H-pyrazolo[3,4-b]pyridin-6-yl)methyl)amino)acrylonitrile:

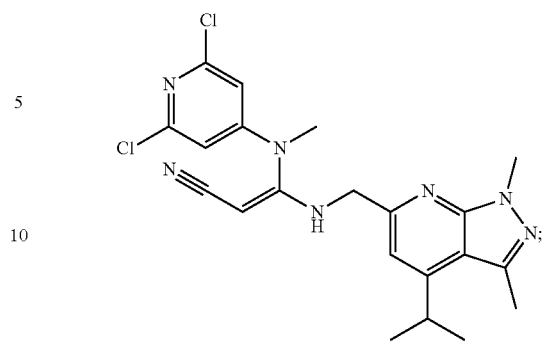

(Z)-3-((2,6-dichloropyridin-4-yl)(ethyl)amino)-3-(((4-isopropyl-1,3-dimethyl-1H-pyrazolo[3,4-b]pyridin-6-yl)methyl)amino)acrylonitrile:

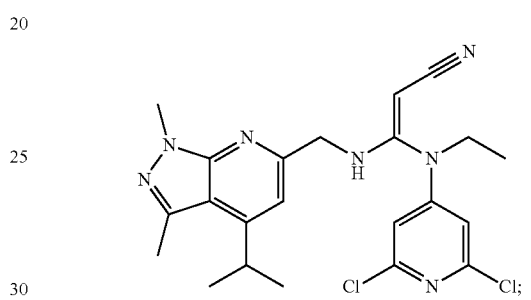

(Z)-3-((2,6-dichloropyridin-4-yl)(propyl)amino)-3-(((4-isopropyl-1,3-dimethyl-1H-pyrazolo[3,4-b]pyridin-6-yl)methyl)amino)acrylonitrile:

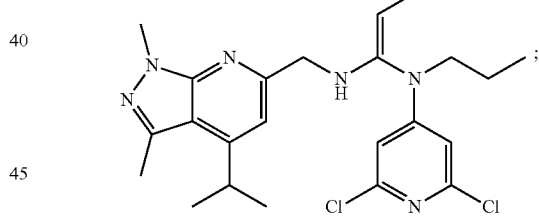

(Z)-3-(butyl(2,6-dichloropyridin-4-yl)amino)-3-(((4-isopropyl-1,3-dimethyl-1H-pyrazolo[3,4-b]pyridin-6-yl)methyl)amino)acrylonitrile:

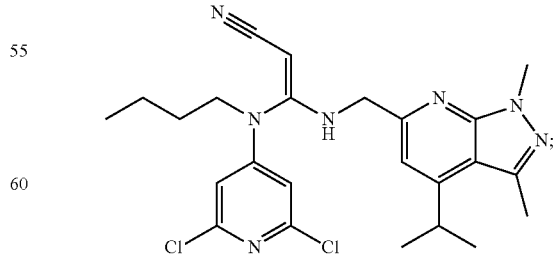

(Z)-3-((2,6-dichloropyridin-4-yl)(isopropyl)amino)-3-(((4-isopropyl-1,3-dimethyl-1H-pyrazolo[3,4-b]pyridin-6-yl)methyl)amino)acrylonitrile:

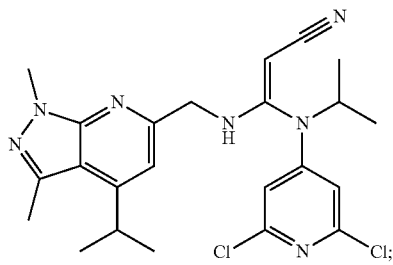 [SMILES: Cc1nn(C)c2nc(CN/C(=C/C#N)N(c3cc(Cl)nc(Cl)c3)C(C)C)cc(C(C)C)c12]

(Z)-3-(benzyl(2,6-dichloropyridin-4-yl)amino)-3-(((4-isopropyl-1,3-dimethyl-1H-pyrazolo[3,4-b]pyridin-6-yl)methyl)amino)acrylonitrile:

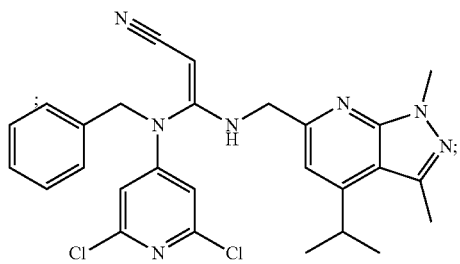 [SMILES: Cc1nn(C)c2nc(CN/C(=C/C#N)N(Cc3ccccc3)c3cc(Cl)nc(Cl)c3)cc(C(C)C)c12]

and, a structural enantiomer of the foregoing, wherein the cyano group is in the (E) form.

In another embodiment, the analog of Compound Z is a compound of formula (XI), wherein:

G is $CR_{10}$; and, $R_x$ and $R_y$ are each H.

In particular for this embodiment, the compound may be selected from the following:

(Z)-3-((2,6-dichloropyridin-4-yl)amino)-3-((1-(4-isopropyl-1,3-dimethyl-1H-pyrazolo[3,4-b]pyridin-6-yl)ethyl)amino)acrylonitrile:

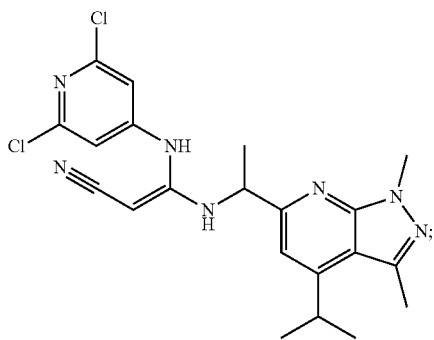 [SMILES: Cc1nn(C)c2nc(C(C)N/C(=C/C#N)Nc3cc(Cl)nc(Cl)c3)cc(C(C)C)c12]

(Z)-3-((2,6-dichloropyridin-4-yl)amino)-3-((1-(4-isopropyl-1,3-dimethyl-1H-pyrazolo[3,4-b]pyridin-6-yl)propyl)amino)acrylonitrile:

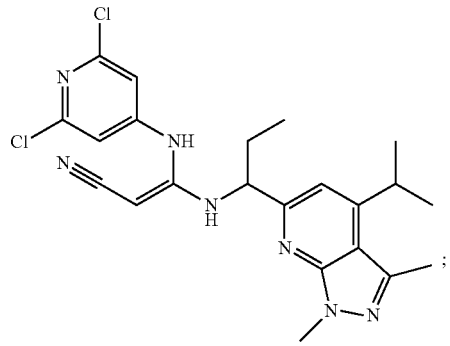 [SMILES: CCC(N/C(=C/C#N)Nc1cc(Cl)nc(Cl)c1)c1cc(C(C)C)c2c(C)nn(C)c2n1]

(Z)-3-((2,6-dichloropyridin-4-yl)amino)-3-((1-(4-isopropyl-1,3-dimethyl-1H-pyrazolo[3,4-b]pyridin-6-yl)-2-methylpropyl)amino)acrylonitrile:

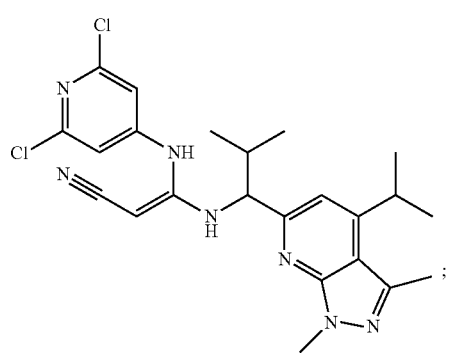 [SMILES: Cc1nn(C)c2nc(C(N/C(=C/C#N)Nc3cc(Cl)nc(Cl)c3)C(C)C)cc(C(C)C)c12]

(Z)-3-((2,6-dichloropyridin-4-yl)amino)-3-((1-(4-isopropyl-1,3-dimethyl-1H-pyrazolo[3,4-b]pyridin-6-yl)-2-phenylethyl)amino)acrylonitrile:

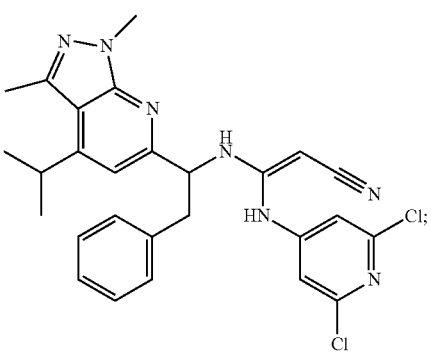 [SMILES: Cc1nn(C)c2nc(C(Cc3ccccc3)N/C(=C/C#N)Nc3cc(Cl)nc(Cl)c3)cc(C(C)C)c12]

and, a structural enantiomer of the foregoing, wherein the cyano group is in the (E) form.

In another embodiment, the analog of Compound Z is a compound of formula (XI), wherein:

G is $NR_{11}$; and, $R_x$ and $R_y$ are each H.

In particular for this embodiment, the compound may be selected from the following:

(E)-3-((2,6-dichloropyridin-4-yl)amino)-3-(2-(4-isopropyl-1,3-dimethyl-1H-pyrazolo[3,4-b]pyridin-6-yl)hydrazinyl)acrylonitrile:

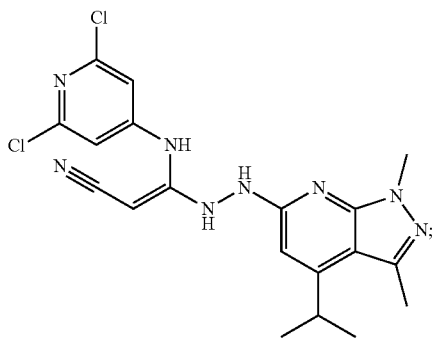

(E)-3-((2,6-dichloropyridin-4-yl)amino)-3-(2-(4-isopropyl-1,3-dimethyl-1H-pyrazolo[3,4-b]pyridin-6-yl)-2-methylhydrazinyl)acrylonitrile:

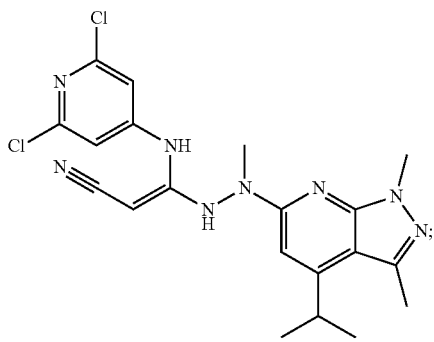

(E)-3-((2,6-dichloropyridin-4-yl)amino)-3-(2-ethyl-2-(4-isopropyl-1,3-dimethyl-1H-pyrazolo[3,4-b]pyridin-6-yl)hydrazinyl)acrylonitrile:

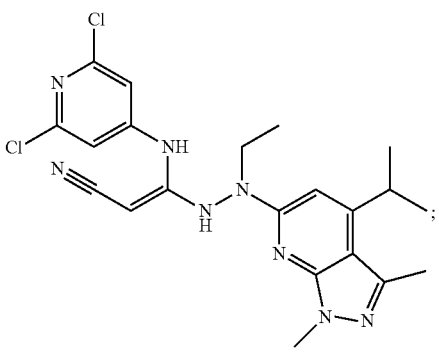 [SMILES: CCN(N/C(=C/C#N)Nc1cc(Cl)nc(Cl)c1)c1cc(C(C)C)c2c(C)nn(C)c2n1]

(E)-3-((2,6-dichloropyridin-4-yl)amino)-3-(2-(4-isopropyl-1,3-dimethyl-1H-pyrazolo[3,4-b]pyridin-6-yl)-2-propylhydrazinyl)acrylonitrile:

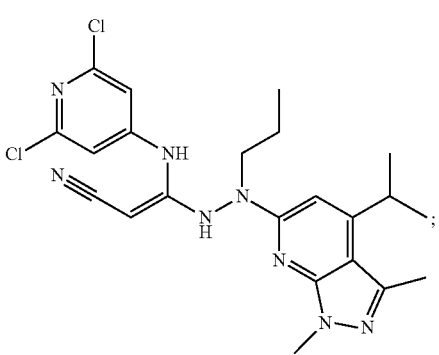 [SMILES: CCCN(N/C(=C/C#N)Nc1cc(Cl)nc(Cl)c1)c1cc(C(C)C)c2c(C)nn(C)c2n1]

(E)-3-(2-butyl-2-(4-isopropyl-1,3-dimethyl-1H-pyrazolo[3,4-b]pyridin-6-yl)hydrazinyl)-3-((2,6-dichloropyridin-4-yl)amino)acrylonitrile:

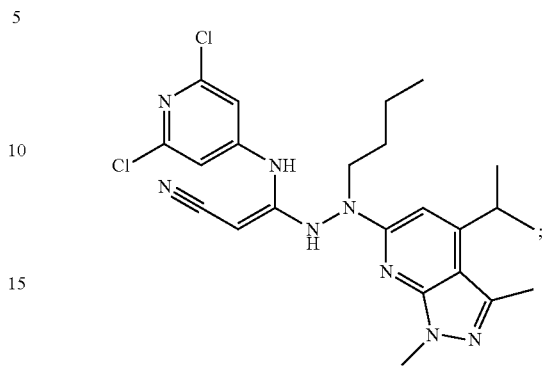

(E)-3-((2,6-dichloropyridin-4-yl)amino)-3-(2-isopropyl-2-(4-isopropyl-1,3-dimethyl-1H-pyrazolo[3,4-b]pyridin-6-yl)hydrazinyl)acrylonitrile:

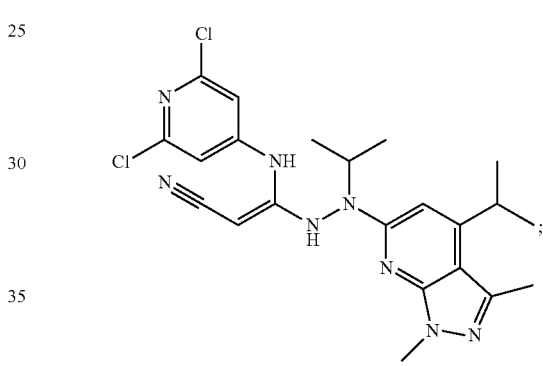

(E)-3-(2-benzyl-2-(4-isopropyl-1,3-dimethyl-1H-pyrazolo[3,4-b]pyridin-6-yl) hydrazinyl)-3-((2,6-dichloropyridin-4-yl)amino)acrylonitrile:

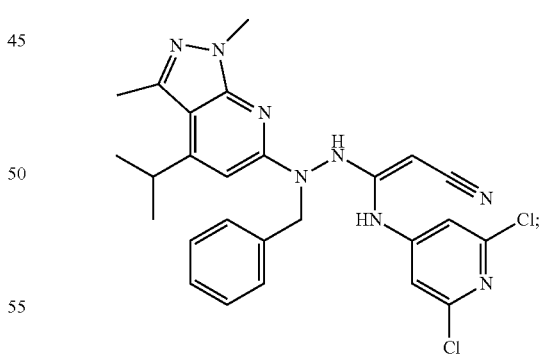

and, a structural enantiomer of the foregoing, wherein the cyano group is in the (Z) form.

In another embodiment, the analog of Compound Z is a compound of formula (XI), wherein:

G is $CR_{10}$ and $R_{10}$ is H.

In particular for this embodiment, the compound may be selected from the following:

(Z)-3-(((2,6-dichloropyridin-4-yl)(methyl)amino)-3-(((4-isopropyl-1,3-dimethyl-1H-pyrazolo[3,4-b]pyridin-6-yl)methyl)(methyl)amino)acrylonitrile:

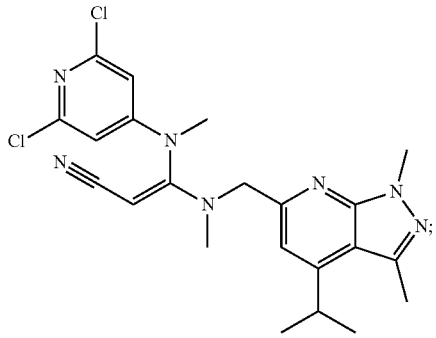 [SMILES: Cc1nn(C)c2nc(CN(C)/C(=C/C#N)N(C)c3cc(Cl)nc(Cl)c3)cc(C(C)C)c12]

(Z)-3-((2,6-dichloropyridin-4-yl)(methyl)amino)-3-(isopropyl((4-isopropyl-1,3-dimethyl-1H-pyrazolo[3,4-b]pyridin-6-yl)methyl)amino)acrylonitrile:

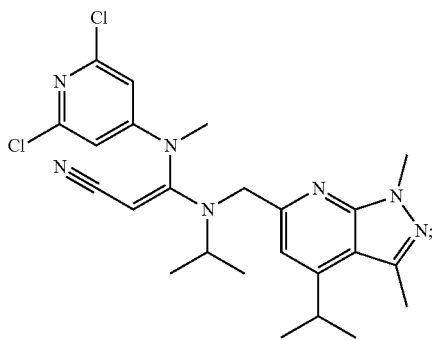 [SMILES: Cc1nn(C)c2nc(CN(/C(=C/C#N)N(C)c3cc(Cl)nc(Cl)c3)C(C)C)cc(C(C)C)c12]

(Z)-3-((2,6-dichloropyridin-4-yl)(isopropyl)amino)-3-(((4-isopropyl-1,3-dimethyl-1H-pyrazolo[3,4-b]pyridin-6-yl)methyl)(methyl)amino)acrylonitrile:

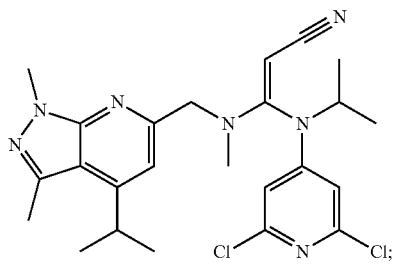 [SMILES: Cc1nn(C)c2nc(CN(C)/C(=C/C#N)N(c3cc(Cl)nc(Cl)c3)C(C)C)cc(C(C)C)c12]

(Z)-3-(benzyl((4-isopropyl-1,3-dimethyl-1H-pyrazolo[3,4-b]pyridin-6-yl)methyl)amino)-3-((2,6-dichloropyridin-4-yl)(methyl)amino)acrylonitrile:

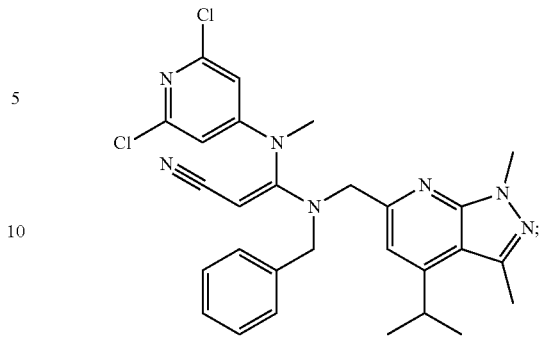

(Z)-3-(benzyl(2,6-dichloropyridin-4-yl)amino)-3-(((4-isopropyl-1,3-dimethyl-1H-pyrazolo[3,4-b]pyridin-6-yl)methyl)(methyl)amino)acrylonitrile:

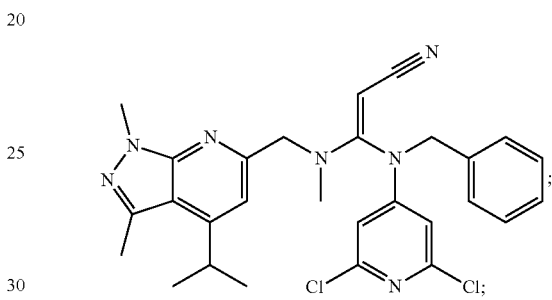

and, a structural enantiomer of the foregoing, wherein the cyano group is in the (E) form.

In another embodiment, the analog of Compound Z is a compound of formula (XI), wherein:

G is $CR_{10}$ and $CR_{10}$ is H; and, $R_x$ and $R_y$ are joined to form a 5- or 6-membered heterocycloalkyl ring.

In particular for this embodiment, the compound may be selected from the following:

(Z)-2-(1-(2,6-dichloropyridin-4-yl)-3-((4-isopropyl-1,3-dimethyl-1H-pyrazolo[3,4-b]pyridin-6-yl)methyl)tetrahydropyrimidin-2(1H)-ylidene)acetonitrile:

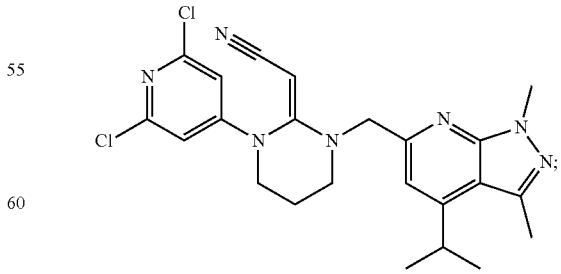

(Z)-2-(1-(2,6-dichloropyridin-4-yl)-3-((4-isopropyl-1,3-dimethyl-1H-pyrazolo[3,4-b]pyridin-6-yl)methyl)imidazolidin-2-ylidene)acetonitrile:

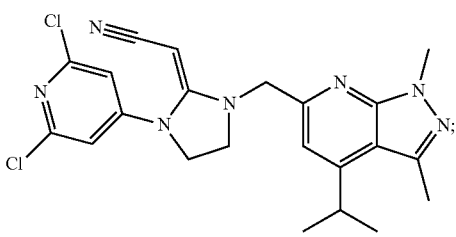 [SMILES: Cc1nn(C)c2nc(CN3CCN(c4cc(Cl)nc(Cl)c4)/C3=C\C#N)cc(C(C)C)c12]

and, a structural enantiomer of the foregoing, wherein the cyano group is in the (E) form.

In another embodiment, the analog of Compound Z is a compound selected from the following:

(Z)-3-((2,6-dichloropyridin-4-yl)amino)-3-(((4-isopropyl-1,3-dimethyl-1H-pyrazolo[3,4-b]pyridin-6-yl)methyl)(methyl)amino)acrylonitrile;

(Z)-3-((2,6-dichloropyridin-4-yl)amino)-3-(ethyl((4-isopropyl-1,3-dimethyl-1H-pyrazolo[3,4-b]pyridin-6-yl)methyl)amino)acrylonitrile;

(Z)-3-((2,6-dichloropyridin-4-yl)amino)-3-(((4-isopropyl-1,3-dimethyl-1H-pyrazolo[3,4-b]pyridin-6-yl)methyl)(propyl)amino)acrylonitrile;

(Z)-3-(butyl((4-isopropyl-1,3-dimethyl-1H-pyrazolo[3,4-b]pyridin-6-yl)methyl)amino)-3-((2,6-dichloropyridin-4-yl)amino)acrylonitrile;

(Z)-3-((2,6-dichloropyridin-4-yl)amino)-3-(isopropyl((4-isopropyl-1,3-dimethyl-1H-pyrazolo[3,4-b]pyridin-6-yl)methyl)amino)acrylonitrile;

(Z)-3-(benzyl((4-isopropyl-1,3-dimethyl-1H-pyrazolo[3,4-b]pyridin-6-yl)methyl)amino)-3((2,6-dichloropyridin-4-yl)amino)acrylonitrile;

(E)-3-((2,6-dichloropyridin-4-yl)(methyl)amino)-3-(((4-isopropyl-1,3-dimethyl-1H-pyrazolo[3,4-b]pyridin-6-yl)methyl)amino)acrylonitrile;

(E)-3-((2,6-dichloropyridin-4-yl)(ethyl)amino)-3-(((4-isopropyl-1,3-dimethyl-1H-pyrazolo[3,4-b]pyridin-6-yl)methyl)amino)acrylonitrile;

(E)-3-((2,6-dichloropyridin-4-yl)(propyl)amino)-3-(((4-isopropyl-1,3-dimethyl-1H-pyrazolo[3,4-b]pyridin-6-yl)methyl)amino)acrylonitrile;

(E)-3-(butyl(2,6-dichloropyridin-4-yl)amino)-3-(((4-isopropyl-1,3-dimethyl-1H-pyrazolo[3,4-b]pyridin-6-yl)methyl)amino)acrylonitrile;

(E)-3-((2,6-dichloropyridin-4-yl)(isopropyl)amino)-3-(((4-isopropyl-1,3-dimethyl-1H-pyrazolo[3,4-b]pyridin-6-yl)methyl)amino)acrylonitrile;

(E)-3-(benzyl(2,6-dichloropyridin-4-yl)amino)-3-(((4-isopropyl-1,3-dimethyl-1H-pyrazolo[3,4-b]pyridin-6-yl)methyl)amino)acrylonitrile;

(E)-3-((2,6-dichloropyridin-4-yl)amino)-3-((1-(4-isopropyl-1,3-dimethyl-1H-pyrazolo[3,4-b]pyridin-6-yl)ethyl)amino)acrylonitrile;

(E)-3-((2,6-dichloropyridin-4-yl)amino)-3-((1-(4-isopropyl-1,3-dimethyl-1H-pyrazolo[3,4-b]pyridin-6-yl)propyl)amino)acrylonitrile;

(E)-3-((2,6-dichloropyridin-4-yl)amino)-3-((1-(4-isopropyl-1,3-dimethyl-1H-pyrazolo[3,4-b]pyridin-6-yl)-2-methylpropyl)amino)acrylonitrile;

(E)-3-((2,6-dichloropyridin-4-yl)amino)-3-((1-(4-isopropyl-1,3-dimethyl-1H-pyrazolo[3,4-b]pyridin-6-yl)-2-phenylethyl)amino)acrylonitrile;

(Z)-3-((2,6-dichloropyridin-4-yl)amino)-3-(2-(4-isopropyl-1,3-dimethyl-1H-pyrazolo[3,4-b]pyridin-6-yl)hydrazinyl)acrylonitrile;

(Z)-3-((2,6-dichloropyridin-4-yl)amino)-3-(2-(4-isopropyl-1,3-dimethyl-1H-pyrazolo[3,4-b]pyridin-6-yl)-2-methylhydrazinyl)acrylonitrile;

(Z)-3-((2,6-dichloropyridin-4-yl)amino)-3-(2-ethyl-2-(4-isopropyl-1,3-dimethyl-1H-pyrazolo[3,4-b]pyridin-6-yl)hydrazinyl)acrylonitrile;

(Z)-3-((2,6-dichloropyridin-4-yl)amino)-3-(2-(4-isopropyl-1,3-dimethyl-1H-pyrazolo[3,4-b]pyridin-6-yl)-2-propylhydrazinyl)acrylonitrile;

(Z)-3-(2-butyl-2-(4-isopropyl-1,3-dimethyl-1H-pyrazolo[3,4-b]pyridin-6-yl)hydrazinyl)-3-((2,6-dichloropyridin-4-yl)amino)acrylonitrile;

(Z)-3-((2,6-dichloropyridin-4-yl)amino)-3-(2-isopropyl-2-(4-isopropyl-1,3-dimethyl-1H-pyrazolo[3,4-b]pyridin-6-yl)hydrazinyl)acrylonitrile;

(Z)-3-(2-benzyl-2-(4-isopropyl-1,3-dimethyl-1H-pyrazolo[3,4-b]pyridin-6-yl) hydrazinyl)-3-((2,6-dichloropyridin-4-yl)amino)acrylonitrile;

(E)-3-((2,6-dichloropyridin-4-yl)(methyl)amino)-3-(((4-isopropyl-1,3-dimethyl-1H-pyrazolo[3,4-b]pyridin-6-yl)methyl)(methyl)amino)acrylonitrile;

(E)-3-((2,6-dichloropyridin-4-yl)(methyl)amino)-3-(isopropyl((4-isopropyl-1,3-dimethyl-1H-pyrazolo[3,4-b]pyridin-6-yl)methyl)amino)acrylonitrile;

(E)-3-((2,6-dichloropyridin-4-yl)(isopropyl)amino)-3-(((4-isopropyl-1,3-dimethyl-1H-pyrazolo[3,4-b]pyridin-6-yl)methyl)(methyl)amino)acrylonitrile;

(E)-3-(benzyl((4-isopropyl-1,3-dimethyl-1H-pyrazolo[3,4-b]pyridin-6-yl)methyl)amino)-3-((2,6-dichloropyridin-4-yl)(methyl)amino)acrylonitrile;

(E)-3-(benzyl(2,6-dichloropyridin-4-yl)amino)-3-(((4-isopropyl-1,3-dimethyl-1H-pyrazolo[3,4-b]pyridin-6-yl)methyl)(methyl)amino)acrylonitrile;

(E)-2-(1-(2,6-dichloropyridin-4-yl)-3-((4-isopropyl-1,3-dimethyl-1H-pyrazolo[3,4-b]pyridin-6-yl)methyl)tetrahydropyrimidin-2(1H)-ylidene)acetonitrile; and, (E)-2-(1-(2,6-dichloropyridin-4-yl)-3-((4-isopropyl-1,3-dimethyl-1H-pyrazolo[3,4-b]pyridin-6-yl)methyl)imidazolidin-2-ylidene)acetonitrile.

3. (Z)-2-cyano-1-(2,6-dichloropyridin-4-yl)-3-((4-isopropyl-1,3-dimethyl-1H-pyrazolo[3,4-b]pyridin-6-yl)methyl)guanidine and Analogs Thereof The S1PR2 antagonist may be (Z)-2-cyano-1-(2,6-dichloropyridin-4-yl)-3-((4-isopropyl-1,3-dimethyl-1H-pyrazolo[3,4-b]pyridin-6-yl)methyl)guanidine (referred to herein as "Compound Y") or an analog thereof, or a pharmaceutically acceptable salt of the foregoing. Compound Y has the following structure:

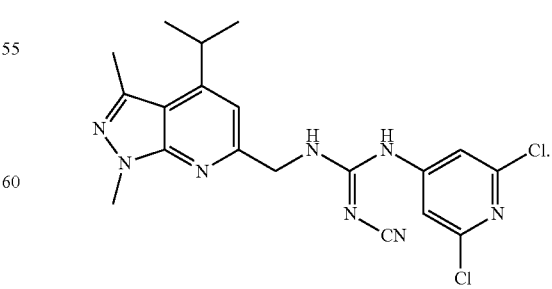

The analog of Compound Y may be a compound of formula (XII):

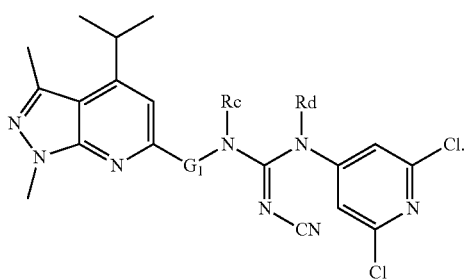

(XII),
wherein:
$G_1$ is $CR_{12}$ or $NR_{13}$, wherein $R_{12}$ and $R_{13}$ are each independently selected from the group consisting of H, $C_1$-$C_4$ alkyl, and benzyl;
$R_c$ and $R_d$ are independently selected from the group consisting of H, $C_1$-$C_4$ alkyl, and benzyl; or $R_c$ and $R_d$ are joined to form a 5- or 6-membered heterocycloalkyl ring; and,
the cyano group is in the (Z) or (E) configuration.

In one embodiment, the analog of Compound Y is a compound of formula (XII), wherein:
$G_1$ is $CR_{12}$ and $R_{12}$ is H; and,
$R_d$ is H.

In particular for this embodiment, the compound may be selected from the following:

(E)-2-cyano-3-(2,6-dichloropyridin-4-yl)-1-((4-isopropyl-1,3-dimethyl-1H-pyrazolo[3,4-b]pyridin-6-yl)methyl)-1-methylguanidine:

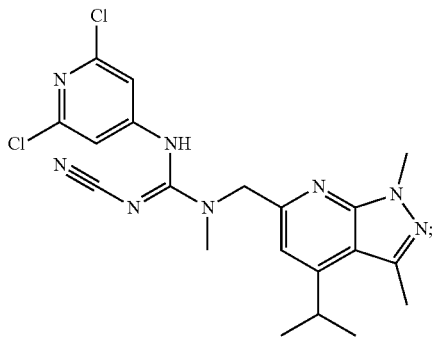 [SMILES: Cc1nn(C)c2nc(CN(C)/C(=N/C#N)Nc3cc(Cl)nc(Cl)c3)cc(C(C)C)c12]

(E)-2-cyano-3-(2,6-dichloropyridin-4-yl)-1-ethyl-1-((4-isopropyl-1,3-dimethyl-1H-pyrazolo[3,4-b]pyridin-6-yl)methyl)guanidine:

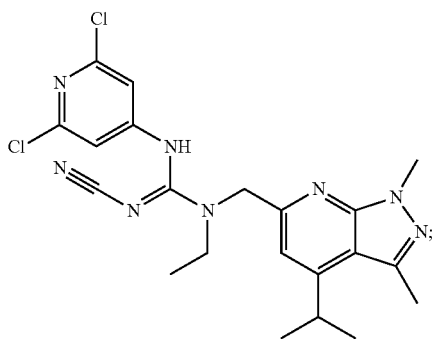 [SMILES: CCN(Cc1cc(C(C)C)c2c(C)nn(C)c2n1)/C(=N/C#N)Nc1cc(Cl)nc(Cl)c1]

(E)-2-cyano-3-(2,6-dichloropyridin-4-yl)-1-((4-isopropyl-1,3-dimethyl-1H-pyrazolo[3,4-b]pyridin-6-yl)methyl)-1-propylguanidine:

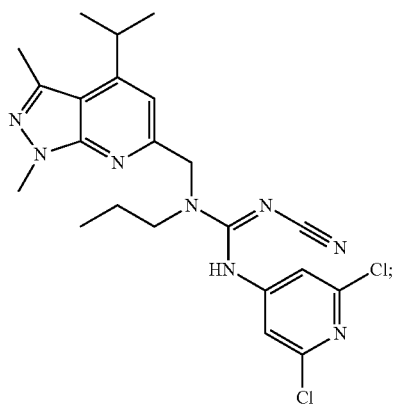 [SMILES: CCCN(Cc1cc(C(C)C)c2c(C)nn(C)c2n1)/C(=N/C#N)Nc1cc(Cl)nc(Cl)c1]

(E)-1-butyl-2-cyano-3-(2,6-dichloropyridin-4-yl)-1-((4-isopropyl-1,3-dimethyl-1H-pyrazolo[3,4-b]pyridin-6-yl)methyl)guanidine:

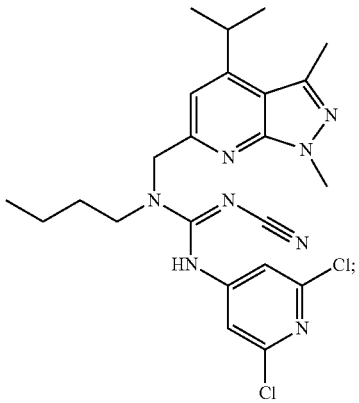 [SMILES: CCCCN(Cc1cc(C(C)C)c2c(C)nn(C)c2n1)/C(=N/C#N)Nc1cc(Cl)nc(Cl)c1]

(E)-2-cyano-3-(2,6-dichloropyridin-4-yl)-1-isopropyl-1-((4-isopropyl-1,3-dimethyl-1H-pyrazolo[3,4-b]pyridin-6-yl)methyl)guanidine:

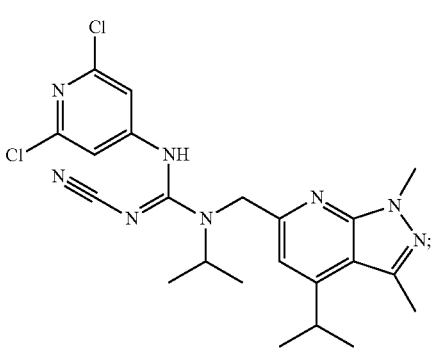 [SMILES: Cc1nn(C)c2nc(CN(/C(=N/C#N)Nc3cc(Cl)nc(Cl)c3)C(C)C)cc(C(C)C)c12]

(E)-1-benzyl-2-cyano-3-(2,6-dichloropyridin-4-yl)-1-((4-isopropyl-1,3-dimethyl-1H-pyrazolo[3,4-b]pyridin-6-yl)methyl)guanidine:

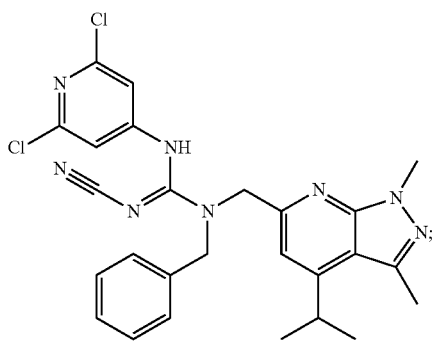 [SMILES: Cc1nn(C)c2nc(CN(Cc3ccccc3)/C(=N/C#N)Nc3cc(Cl)nc(Cl)c3)cc(C(C)C)c12]

and, a diastereomer of the foregoing, wherein the cyano group is in the (Z) form.

In another embodiment, the analog of Compound Y is a compound of formula (XII), wherein:

$G_1$ is $CR_{12}$ and $R_{12}$ is H; and, $R_c$ is H.

In particular for this embodiment, the compound may be selected from the following:

(Z)-2-cyano-1-(2,6-dichloropyridin-4-yl)-3-((4-isopropyl-1,3-dimethyl-1H-pyrazolo[3,4-b]pyridin-6-yl)methyl)-1-methylguanidine:

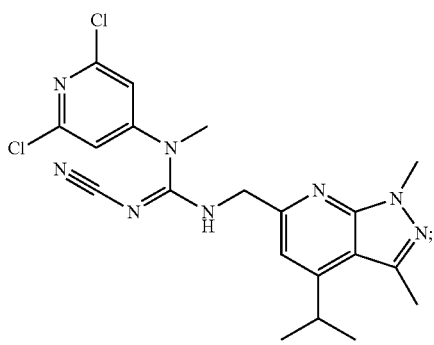 [SMILES: Cc1nn(C)c2nc(CN/C(=N/C#N)N(C)c3cc(Cl)nc(Cl)c3)cc(C(C)C)c12]

(Z)-2-cyano-1-(2,6-dichloropyridin-4-yl)-1-ethyl-3-((4-isopropyl-1,3-dimethyl-1H-pyrazolo[3,4-b]pyridin-6-yl)methyl)guanidine:

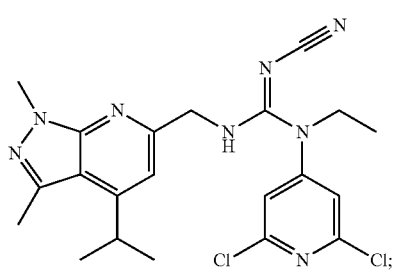 [SMILES: CCN(/C(=N\C#N)NCc1cc(C(C)C)c2c(C)nn(C)c2n1)c1cc(Cl)nc(Cl)c1]

(Z)-2-cyano-1-(2,6-dichloropyridin-4-yl)-3-((4-isopropyl-1,3-dimethyl-1H-pyrazolo[3,4-b]pyridin-6-yl)methyl)-1-propylguanidine:

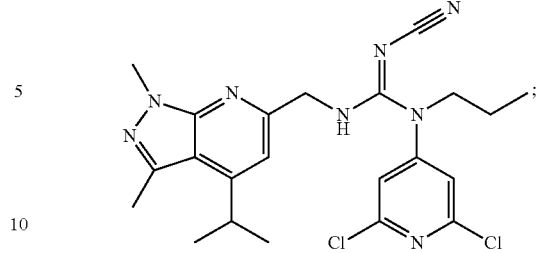

(Z)-1-butyl-2-cyano-1-(2,6-dichloropyridin-4-yl)-3-((4-isopropyl-1,3-dimethyl-1H-pyrazolo[3,4-b]pyridin-6-yl)methyl)guanidine:

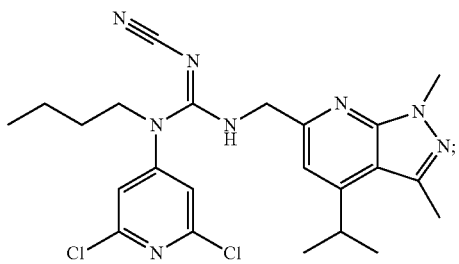 [SMILES: CCCCN(/C(=N\C#N)NCc1cc(C(C)C)c2c(C)nn(C)c2n1)c1cc(Cl)nc(Cl)c1]

(Z)-2-cyano-1-(2,6-dichloropyridin-4-yl)-1-isopropyl-3-((4-isopropyl-1,3-dimethyl-1H-pyrazolo[3,4-b]pyridin-6-yl)methyl)guanidine:

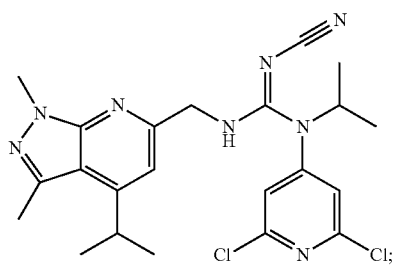 [SMILES: Cc1nn(C)c2nc(CN/C(=N/C#N)N(c3cc(Cl)nc(Cl)c3)C(C)C)cc(C(C)C)c12]

(Z)-1-benzyl-2-cyano-1-(2,6-dichloropyridin-4-yl)-3-((4-isopropyl-1,3-dimethyl-1H-pyrazolo[3,4-b]pyridin-6-yl)methyl)guanidine:

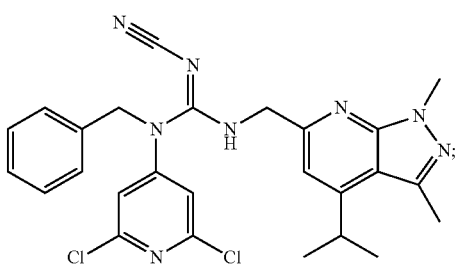 [SMILES: Cc1nn(C)c2nc(CN/C(=N/C#N)N(Cc3ccccc3)c3cc(Cl)nc(Cl)c3)cc(C(C)C)c12]

and, a diastereomer of the foregoing, wherein the cyano group is in the (E) form.

In another embodiment, the analog of Compound Y is a compound of formula (XII), wherein:

$G_1$ is $CR_{12}$; and, $R_c$ and $R_d$ are each H.

In particular for this embodiment, the compound may be selected from the following:

(Z)-2-cyano-1-(2,6-dichloropyridin-4-yl)-3-(1-(4-isopropyl-1,3-dimethyl-1H-pyrazolo[3,4-b]pyridin-6-yl)ethyl)guanidine:

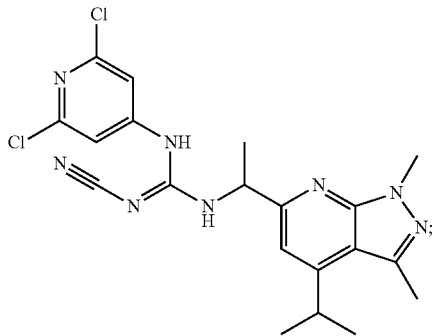 [SMILES: Cc1nn(C)c2nc(C(C)N/C(=N/C#N)Nc3cc(Cl)nc(Cl)c3)cc(C(C)C)c12]

(Z)-2-cyano-1-(2,6-dichloropyridin-4-yl)-3-(1-(4-isopropyl-1,3-dimethyl-1H-pyrazolo[3,4-b]pyridin-6-yl)propyl)guanidine:

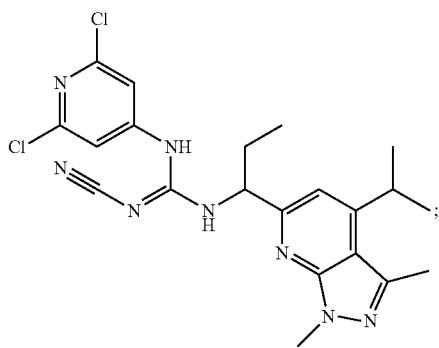

(Z)-2-cyano-1-(2,6-dichloropyridin-4-yl)-3-(1-(4-isopropyl-1,3-dimethyl-1H-pyrazolo[3,4-b]pyridin-6-yl)-2-methylpropyl)guanidine:

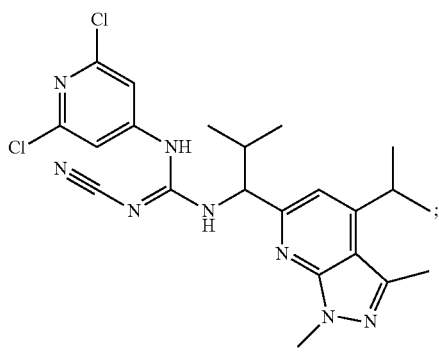

(Z)-2-cyano-1-(2,6-dichloropyridin-4-yl)-3-(1-(4-isopropyl-1,3-dimethyl-1pyrazolo[3,4-b]pyridin-6-yl)-2-phenylethyl)guanidine:

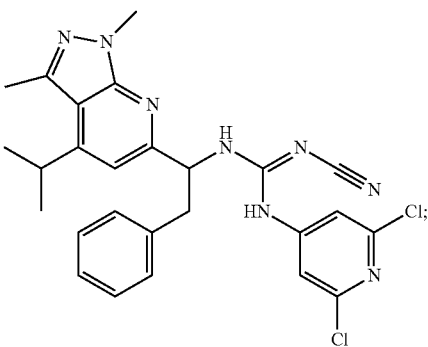

and, a diastereomer of the foregoing, wherein the cyano group is in the (E) form.

In another embodiment, the analog of Compound Y is a compound of formula (XII), wherein:

$G_1$ is $NR_{13}$; and, $R_c$ and $R_d$ are each H.

In particular for this embodiment, the compound may be selected from the following:

(E)-N'-cyano-N-(2,6-dichloropyridin-4-yl)-2-(4-isopropyl-1,3-dimethyl-1H-pyrazolo[3,4-b]pyridin-6-yl)hydrazinecarboximidamide:

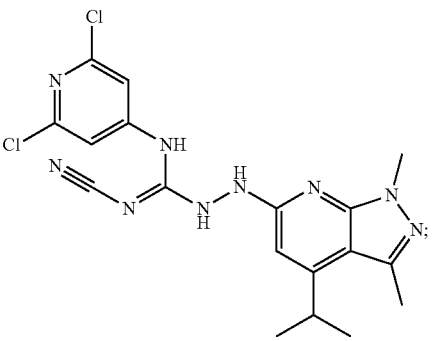 [SMILES: Cc1nn(C)c2nc(NN/C(=N/C#N)Nc3cc(Cl)nc(Cl)c3)cc(C(C)C)c12]

(E)-N'-cyano-N-(2,6-dichloropyridin-4-yl)-2-(4-isopropyl-1,3-dimethyl-1H-pyrazolo[3,4-b]pyridin-6-yl)-2-methylhydrazinecarboximidamide:

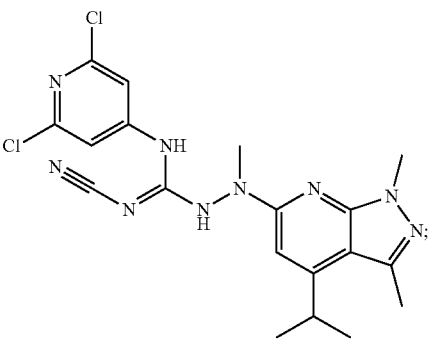 [SMILES: Cc1nn(C)c2nc(N(C)N/C(=N/C#N)Nc3cc(Cl)nc(Cl)c3)cc(C(C)C)c12]

(E)-N'-cyano-N-(2,6-dichloropyridin-4-yl)-2-ethyl-2-(4-isopropyl-1,3-dimethyl-1H-pyrazolo[3,4-b]pyridin-6-yl)hydrazinecarboximidamide:

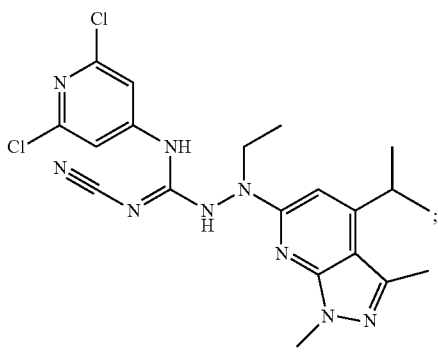

(E)-N'-cyano-N-(2,6-dichloropyridin-4-yl)-2-(4-isopropyl-1,3-dimethyl-1H-pyrazolo[3,4-b]pyridin-6-yl)-2-propylhydrazinecarboximidamide:

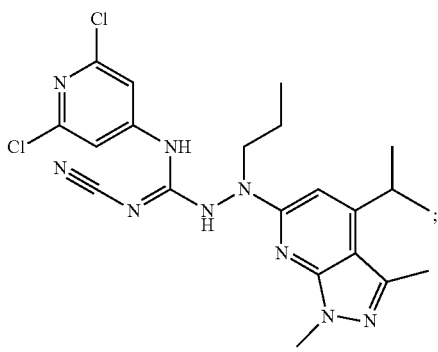

(E)-2-butyl-N'-cyano-N-(2,6-dichloropyridin-4-yl)-2-(4-isopropyl-1,3-dimethyl-1H-pyrazolo[3,4-b]pyridin-6-yl)hydrazinecarboximidamide:

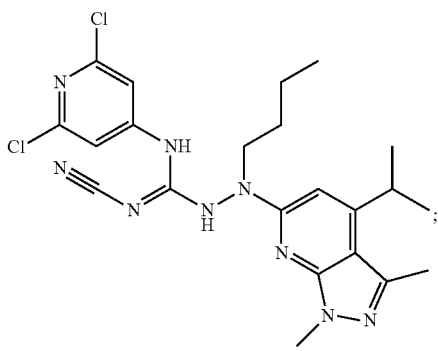 [SMILES: CCCCN(N/C(=N/C#N)Nc1cc(Cl)nc(Cl)c1)c1cc(C(C)C)c2c(C)nn(C)c2n1]

(E)-N'-cyano-N-(2,6-dichloropyridin-4-yl)-2-isopropyl-2-(4-isopropyl-1,3-dimethyl-1H-pyrazolo[3,4-b]pyridin-6-yl)hydrazinecarboximidamide:

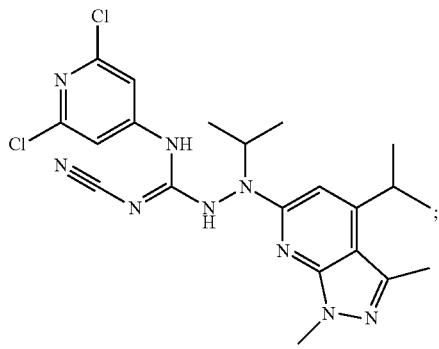 [SMILES: Cc1nn(C)c2nc(N(N/C(=N/C#N)Nc3cc(Cl)nc(Cl)c3)C(C)C)cc(C(C)C)c12]

(E)-2-benzyl-N'-cyano-N-(2,6-dichloropyridin-4-yl)-2-(4-isopropyl-1,3-dimethyl-1H-pyrazolo[3,4-b]pyridin-6-yl)hydrazinecarboximidamide:

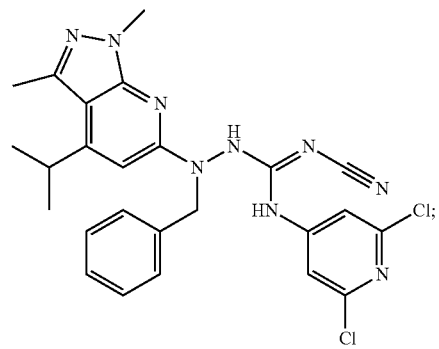

and, a diastereomer of the foregoing, wherein the cyano group is in the (Z) form.

In another embodiment, the analog of Compound Y is a compound of formula (XII), wherein:

$G_1$ is $CR_{12}$ and $R_{12}$ is H.

In particular for this embodiment, the compound may be selected from the following:

(Z)-2-cyano-1-(2,6-dichloropyridin-4-yl)-3-((4-isopropyl-1,3-dimethyl-1H-pyrazolo[3,4-b]pyridin-6-yl)methyl)-1,3-dimethylguanidine:

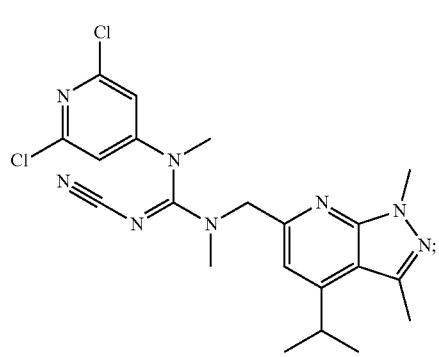 [SMILES: Cc1nn(C)c2nc(CN(C)/C(=N/C#N)N(C)c3cc(Cl)nc(Cl)c3)cc(C(C)C)c12]

(Z)-2-cyano-1-(2,6-dichloropyridin-4-yl)-3-isopropyl-3-((4-isopropyl-1,3-dimethyl-1H-pyrazolo[3,4-b]pyridin-6-yl)methyl)-1-methylguanidine:

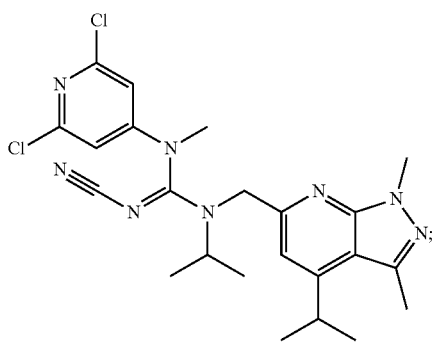 [SMILES: Cc1nn(C)c2nc(CN(/C(=N/C#N)N(C)c3cc(Cl)nc(Cl)c3)C(C)C)cc(C(C)C)c12]

(Z)-2-cyano-1-(2,6-dichloropyridin-4-yl)-1-isopropyl-3-((4-isopropyl-1,3-dimethyl-1H-pyrazolo[3,4-b]pyridin-6-yl)methyl)-3-methylguanidine:

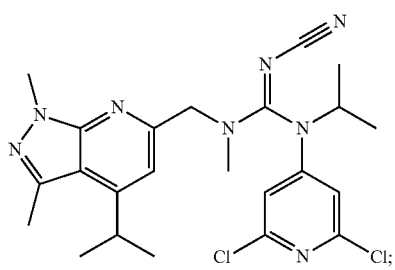

(Z)-1-benzyl-2-cyano-3-(2,6-dichloropyridin-4-yl)-1-((4-isopropyl-1,3-dimethyl-1H-pyrazolo[3,4-b]pyridin-6-yl)methyl)-3-methylguanidine:

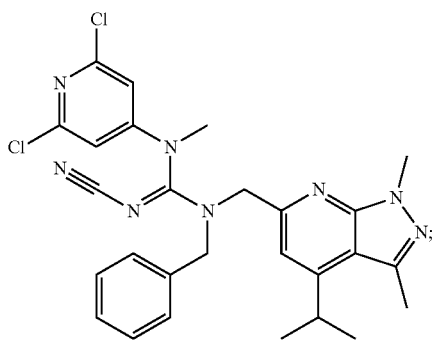 [SMILES: Cc1nn(C)c2nc(CN(Cc3ccccc3)/C(=N/C#N)N(C)c3cc(Cl)nc(Cl)c3)cc(C(C)C)c12]

(Z)-1-benzyl-2-cyano-1-(2,6-dichloropyridin-4-yl)-3-((4-isopropyl-1,3-dimethyl-1H-pyrazolo[3,4-b]pyridin-6-yl)methyl)-3-methylguanidine:

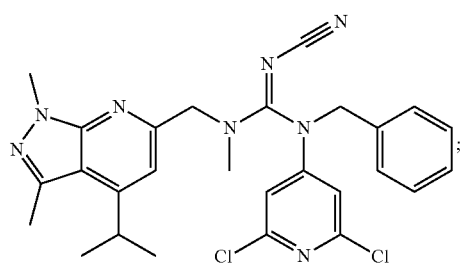 [SMILES: Cc1nn(C)c2nc(CN(C)/C(=N/C#N)N(Cc3ccccc3)c3cc(Cl)nc(Cl)c3)cc(C(C)C)c12]

and,
a diastereomer of the foregoing, wherein the cyano group is in the (E) form.

In another embodiment, the analog of Compound Y is a compound of formula (XII), wherein:
G is $CR_{12}$ and $CR_{12}$ is H; and,
$R_c$ and $R_d$ are joined to form a 5- or 6-membered heterocycloalkyl ring.

In particular for this embodiment, the compound may be selected from the following:
(Z)—N-(1-(2,6-dichloropyridin-4-yl)-3-((4-isopropyl-1,3-dimethyl-1H-pyrazolo[3,4-b]pyridin-6-yl)methyl)tetrahydropyrimidin-2(1H)-ylidene)cyanamide:

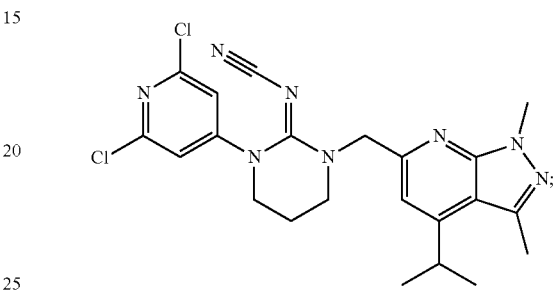

(Z)—N-(1-(2,6-dichloropyridin-4-yl)-3-((4-isopropyl-1,3-dimethyl-1H-pyrazolo[3,4-b]pyridin-6-yl)methyl)imidazolidin-2-ylidene)cyanamide:

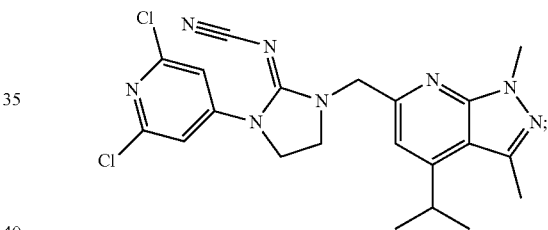

and,
a diastereomer of the foregoing, wherein the cyano group is in the (E) form.

In another embodiment, the analog of Compound Y is a compound selected from the following:
(Z)-2-cyano-3-(2,6-dichloropyridin-4-yl)-1-((4-isopropyl-1,3-dimethyl-1H-pyrazolo[3,4-b]pyridin-6-yl)methyl)-1-methylguanidine;
(Z)-2-cyano-3-(2,6-dichloropyridin-4-yl)-1-ethyl-1-((4-isopropyl-1,3-dimethyl-1H-pyrazolo[3,4-b]pyridin-6-yl)methyl)guanidine;
(Z)-2-cyano-3-(2,6-dichloropyridin-4-yl)-1-((4-isopropyl-1,3-dimethyl-1H-pyrazolo [3,4-b]pyridin-6-yl)methyl)-1-propylguanidine;
(Z)-1-butyl-2-cyano-3-(2,6-dichloropyridin-4-yl)-1-((4-isopropyl-1,3-dimethyl-1H-pyrazolo[3,4-b]pyridin-6-yl)methyl)guanidine;
(Z)-2-cyano-3-(2,6-dichloropyridin-4-yl)-1-isopropyl-1-((4-isopropyl-1,3-dimethyl-1H-pyrazolo[3,4-b]pyridin-6-yl)methyl)guanidine;
(Z)-1-benzyl-2-cyano-3-(2,6-dichloropyridin-4-yl)-1-((4-isopropyl-1,3-dimethyl-1H-pyrazolo[3,4-b]pyridin-6-yl)methyl)guanidine;
(E)-2-cyano-1-(2,6-dichloropyridin-4-yl)-3-((4-isopropyl-1,3-dimethyl-1H-pyrazolo[3,4-b]pyridin-6-yl)methyl)-1-methylguanidine;

(E)-2-cyano-1-(2,6-dichloropyridin-4-yl)-1-ethyl-3-((4-isopropyl-1,3-dimethyl-1H-pyrazolo[3,4-b]pyridin-6-yl)methyl)guanidine;

(E)-2-cyano-1-(2,6-dichloropyridin-4-yl)-3-((4-isopropyl-1,3-dimethyl-1H-pyrazolo[3,4-b]pyridin-6-yl)methyl)-1-propylguanidine;

(E)-1-butyl-2-cyano-1-(2,6-dichloropyridin-4-yl)-3-((4-isopropyl-1,3-dimethyl-1H-pyrazolo[3,4-b]pyridin-6-yl)methyl)guanidine;

(E)-2-cyano-1-(2,6-dichloropyridin-4-yl)-1-isopropyl-3-((4-isopropyl-1,3-dimethyl-1H-pyrazolo[3,4-b]pyridin-6-yl)methyl)guanidine;

(E)-1-benzyl-2-cyano-1-(2,6-dichloropyridin-4-yl)-3-((4-isopropyl-1,3-dimethyl-1H-pyrazolo[3,4-b]pyridin-6-yl)methyl)guanidine;

(E)-2-cyano-1-(2,6-dichloropyridin-4-yl)-3-(1-(4-isopropyl-1,3-dimethyl-1H-pyrazolo[3,4-b]pyridin-6-yl)ethyl)guanidine;

(E)-2-cyano-1-(2,6-dichloropyridin-4-yl)-3-(1-(4-isopropyl-1,3-dimethyl-1H-pyrazolo[3,4-b]pyridin-6-yl)propyl)guanidine;

(E)-2-cyano-1-(2,6-dichloropyridin-4-yl)-3-(1-(4-isopropyl-1,3-dimethyl-1H-pyrazolo[3,4-b]pyridin-6-yl)-2-methylpropyl)guanidine;

(E)-2-cyano-1-(2,6-dichloropyridin-4-yl)-3-(1-(4-isopropyl-1,3-dimethyl-1H-pyrazolo[3,4-b]pyridin-6-yl)-2-phenylethyl)guanidine;

(Z)-N'-cyano-N-(2,6-dichloropyridin-4-yl)-2-(4-isopropyl-1,3-dimethyl-1H-pyrazolo[3,4-b]pyridin-6-yl)hydrazinecarboximidamide;

(Z)-N'-cyano-N-(2,6-dichloropyridin-4-yl)-2-(4-isopropyl-1,3-dimethyl-1H-pyrazolo[3,4-b]pyridin-6-yl)-2-methylhydrazinecarboximidamide;

(Z)-N'-cyano-N-(2,6-dichloropyridin-4-yl)-2-ethyl-2-(4-isopropyl-1,3-dimethyl-1H-pyrazolo[3,4-b]pyridin-6-yl)hydrazinecarboximidamide;

(Z)-N'-cyano-N-(2,6-dichloropyridin-4-yl)-2-(4-isopropyl-1,3-dimethyl-1H-pyrazolo[3,4-b]pyridin-6-yl)-2-propylhydrazinecarboximidamide;

(Z)-2-butyl-N'-cyano-N-(2,6-dichloropyridin-4-yl)-2-(4-isopropyl-1,3-dimethyl-1H-pyrazolo[3,4-b]pyridin-6-yl)hydrazinecarboximidamide;

(Z)-N'-cyano-N-(2,6-dichloropyridin-4-yl)-2-isopropyl-2-(4-isopropyl-1,3-dimethyl-1H-pyrazolo[3,4-b]pyridin-6-yl)hydrazinecarboximidamide;

(Z)-2-benzyl-N'-cyano-N-(2,6-dichloropyridin-4-yl)-2-(4-isopropyl-1,3-dimethyl-1H-pyrazolo[3,4-b]pyridin-6-yl)hydrazinecarboximidamide;

(E)-2-cyano-1-(2,6-dichloropyridin-4-yl)-3-((4-isopropyl-1,3-dimethyl-1H-pyrazolo[3,4-b]pyridin-6-yl)methyl)-1,3-dimethylguanidine;

(E)-2-cyano-1-(2,6-dichloropyridin-4-yl)-3-isopropyl-3-((4-isopropyl-1,3-dimethyl-1H-pyrazolo[3,4-b]pyridin-6-yl)methyl)-1-methylguanidine;

(E)-2-cyano-1-(2,6-dichloropyridin-4-yl)-1-isopropyl-3-((4-isopropyl-1,3-dimethyl-1H-pyrazolo[3,4-b]pyridin-6-yl)methyl)-3-methylguanidine;

(E)-1-benzyl-2-cyano-3-(2,6-dichloropyridin-4-yl)-1-((4-isopropyl-1,3-dimethyl-1H-pyrazolo[3,4-b]pyridin-6-yl)methyl)-3-methylguanidine;

(E)-1-benzyl-2-cyano-1-(2,6-dichloropyridin-4-yl)-3-((4-isopropyl-1,3-dimethyl-1H-pyrazolo[3,4-b]pyridin-6-yl)methyl)-3-methylguanidine;

(E)-N-(1-(2,6-dichloropyridin-4-yl)-3-((4-isopropyl-1,3-dimethyl-1H-pyrazolo[3,4-b]pyridin-6-yl)methyl)tetrahydropyrimidin-2(1H)-ylidene)cyanamide; and, (E)-N-(1-(2,6-dichloropyridin-4-yl)-3-((4-isopropyl-1,3-dimethyl-1H-pyrazolo[3,4-b]pyridin-6-yl)methyl)imidazolidin-2-ylidene)cyanamide.

4. Administration

The S1PR2 antagonist compounds are typically formulated for therapeutic use. In certain embodiments, the invention relates to pharmaceutical compositions comprising a S1PR2 antagonist compound and a pharmaceutically acceptable carrier, diluent, or excipient. The pharmaceutical compositions may be prepared by known procedures using well-known and readily available ingredients (see, for example, Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999)).

The pharmaceutical compositions may be administered to a subject by any suitable route, e.g., systemically by intravenous injection, directly through intraocular injection, by eye drops, orally, or the like. The compositions may be administered directly to a target site by, for example, surgical delivery to an internal or external target site, or by catheter to a site accessible by a blood vessel.

For example, in a method of treating a S1PR2-related eye condition, such as FEVR, a composition as described herein may be delivered through intraocular injection, by drops, orally, or intravenously. The compositions may be administered in a single bolus, multiple injections, or by continuous infusion (e.g., intravenously, or intrathecally by peritoneal dialysis, pump infusion). For parenteral administration, the compositions are preferably formulated in a sterilized pyrogen-free form. As indicated above, the compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like. The compositions described herein may be administered to mammals (e.g., rodents, humans, nonhuman primates, canines, felines, ovines, bovines) in any suitable formulation according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999), a standard text in this field, and in USP/NF). A description of exemplary pharmaceutically acceptable carriers and diluents, as well as pharmaceutical formulations, can be found in Remington: supra. Other substances may be added to the compositions to stabilize and/or preserve the compositions.

The therapeutic methods described herein in general include administration of a therapeutically effective amount of the compositions described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The methods and compositions herein may be used in the treatment of any other disorders or diseases relating to anemia.

5. Effective Doses

The compositions described herein are preferably administered to a mammal (e.g., human) in an effective amount, that is, an amount capable of producing a desirable result in a treated mammal (e.g., treating FEVR through administration of S1PR2 antagonists). Such a therapeutically effective amount can be determined according to standard methods.

Toxicity and therapeutic efficacy of the compositions utilized in methods of the technology can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently. A delivery dose of a composition as described herein may be determined based on preclinical efficacy and safety.

EXAMPLES

The present technology is further illustrated by the following specific examples. The examples are provided for illustration only and should not be construed as limiting the scope of the technology in any way.

Example 1

Figure 5:
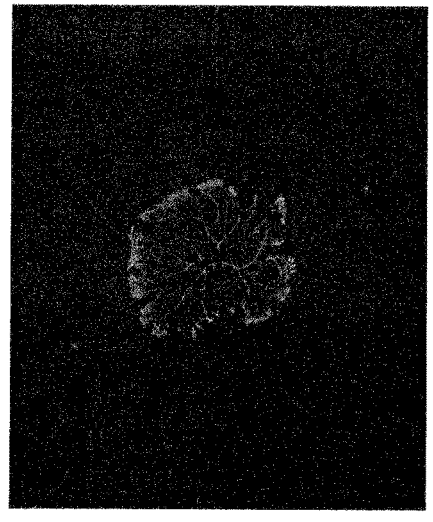
FIG. 5 illustrates the amelioration of vasculature patterning in the Tspan12$^{-/-}$ mouse model of FEVR upon inactivation of the S1pr2 gene. Retinas were flat mounted at P17 and the vasculature visualized by confocal microscopy subsequent to staining with iso-lectin B4 AlexaFluor 594.
Figure 5:
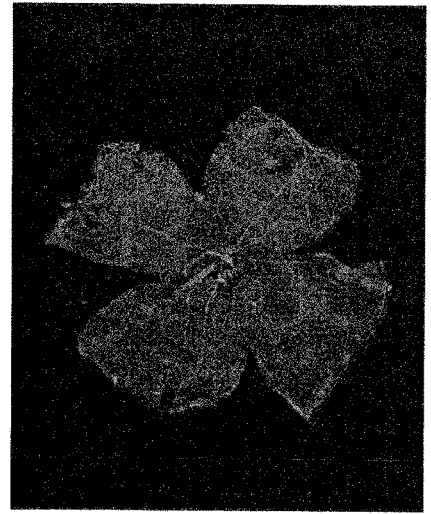
Figure 5:
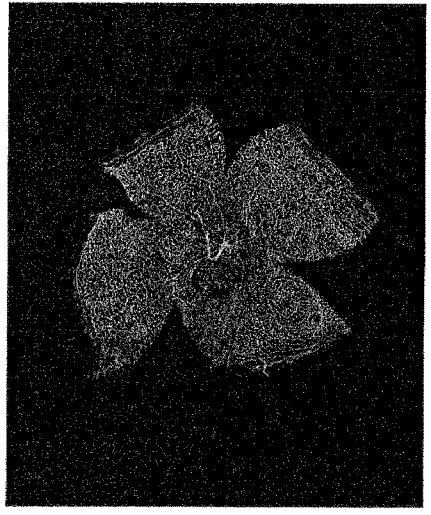

Normalization of Retinal Vasculature in FEVR Model by Genetic Inhibition of S1PR2 Activity S1pr2$^{-/-}$ Tspan12$^{-/-}$ double knockout mice were generated and observed a remarkable amelioration of retinal vasculature patterning mice (FIG. 5). (TSPAN12 regulates retinal vascular development by promoting Norrin- but not Wnt-induced FZD4/beta-catenin signaling. Junge H J, Yang S, Burton J B, Paes K, Shu X, French D M, Costa M, Rice D S, Ye W. Cell 139, 299-311 (2009).)

Figure 6:
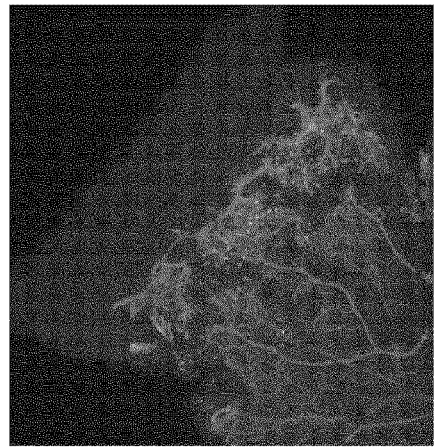
FIG. 6 illustrates amelioration of vasculature patterning in the Fzd4$^{-/-}$ mouse model of FEVR upon inactivation of the S1pr2 gene. Retinas were flat mounted at P17 and the vasculature visualized by confocal microscopy subsequent to staining with iso-lectin B4 AlexaFluor 594.
Figure 6:
Figure 6:
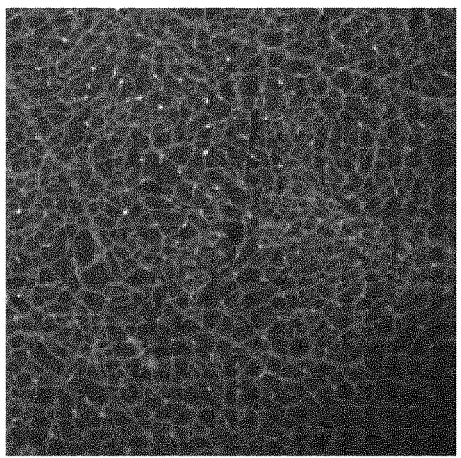

Fzd4$^{-/-}$ S1pr2$^{-/-}$ mice were also generated and these mice also show amelioration of retinal vasculature patterning (FIG. 6). (Vascular development in the retina and inner ear: control by Norrin and Frizzled-4, a high-affinity ligand-receptor pair. Xu Q, Wang Y, Dabdoub A, Smallwood P M, Williams J, Woods C, Kelley M W, Jiang L, Tasman W, Zhang K, Nathans J. Cell 116, 883-95 (2004).) Thus, inhibition of S1PR2 is a significant therapeutic approach for FEVR.

Example 2

Figure 7:
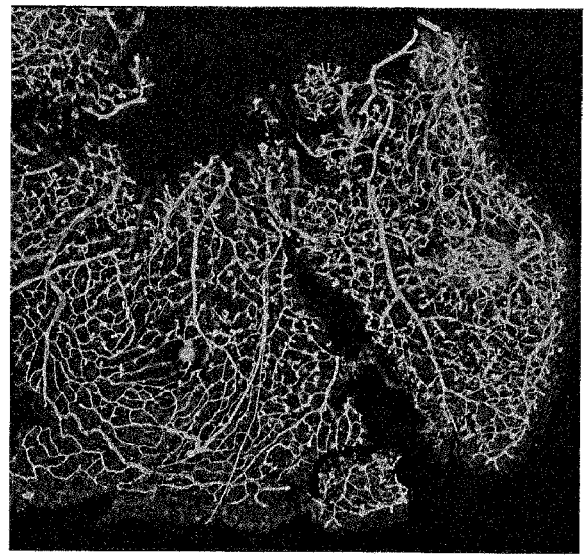
FIG. 7 illustrates that treatment of Fzd4$^{-/-}$ mice with the S1PR2 antagonist JTE-013 ameliorates the FEVR phenotype. Fzd4$^{-/-}$ mice were injected with 0.5 mg/kg JTE-013 intraperitoneally every second day from P7 to P25. Retinas were flat mounted at P25 and the vasculature visualized by confocal microscopy subsequent to staining with iso-lectin B4 AlexaFluor 594. There was substantial restoration of normal retinal vascular patterning in the mice treated with JTE-013.
Figure 7:
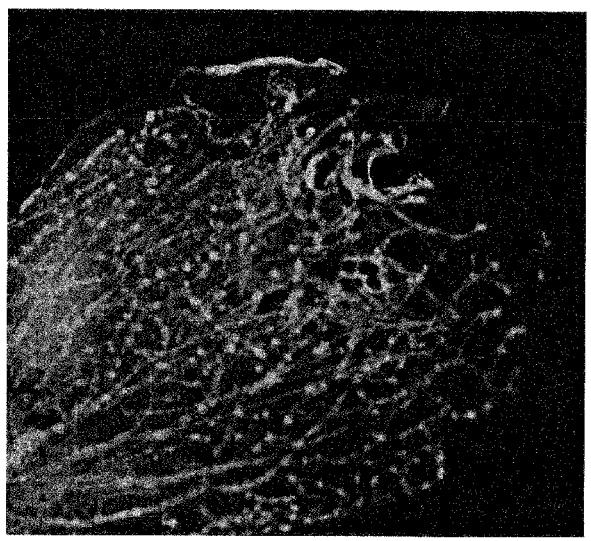

Normalization of Retinal Vasculature in FEVR Model by Administration of S1PR2 Antagonist Post-natal treatment of Fzd4$^{-/-}$ mice with the S1PR2 antagonist JTE-013 was able to ameliorate FEVR retinal vascularization defects (FIG. 7). Fzd4$^{-/-}$ mice were injected with 0.5 mg/kg JTE-013 intraperitoneally every second day from P7 to P25. Using standard protocols, retinas were flat mounted at P25 and the vasculature visualized by confocal microscopy subsequent to staining with iso-lectin B4 Alex-aFluor 594. (Vascular development in the retina and inner ear: control by Norrin and Frizzled-4, a high-affinity ligand-receptor pair. Xu Q, Wang Y, Dabdoub A, Smallwood P M, Williams J, Woods C, Kelley M W, Jiang L, Tasman W, Zhang K, Nathans J. Cell 116, 883-95 (2004).)

Example 3

Computer Aided Drug Design of S1PR2 Antagonists

In general, G protein coupled receptors are considered highly druggable, and a broad specificity S1PR agonist (Fingolimod, trade name Gilenya) that simultaneously targets S1PR1-3 and -5 is on the market for the treatment of multiple sclerosis. Computer aided drug design has been used in the past to successfully design and synthesize small molecule inhibitors of lipid enzymes that are now in late stage preclinical evaluation for a subsequent Phase 1/2a clinical trial.

Figure 8:
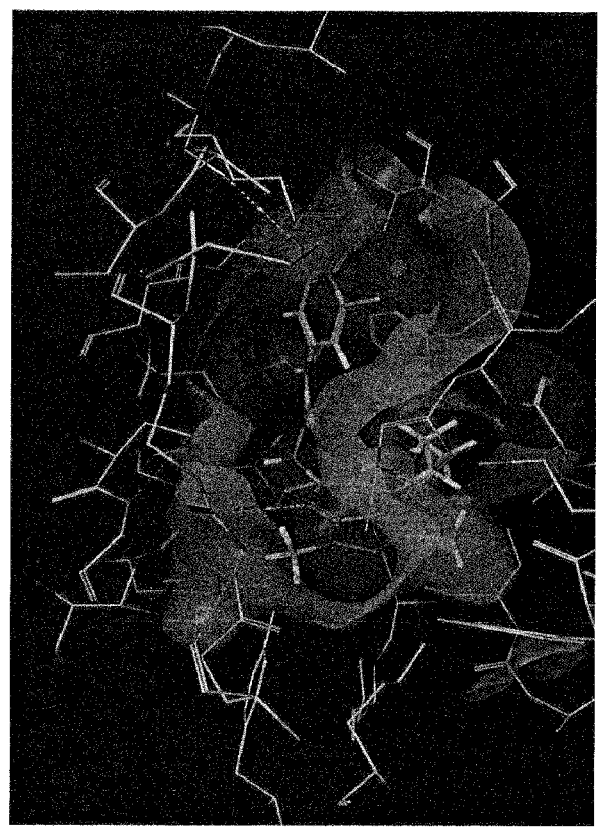
FIG. 8 illustrates the sphingosine-1-phosphate receptor 2 (S1PR2) binding pocket. A pocket composed of 34 amino acids located on the extracellular face of the protein was identified, and correlates to that of its counterpart sphingosine-1-phosphate receptors. The amino acids are as follows: Tyr18, Lys22, Glu23, Leu25, Glu26, Gln28, Glu29, Thr30, Arg33, Ala36, Ser37, Ile40, Phe86, Asn89, Thr90, Leu92, Ser93, Gly94, Ser95, Thr97, Leu98, Trp105, Arg108, Glu109, Val182, Leu183, Pro184, Tyr268, Lys269, Ala270, His271, Tyr272, Phe274, and Ala275. These amino acids are located on transmembrane domains I, II, III and VII of the protein. The human S1PR2 ligand binding pocket is shown with JTE-013 bound. JTE-013 is a compound with 18 nM affinity for S1PR2 and 100-fold greater specificity for S1PR2 versus other S1PRs. Molecular modeling of the S1PR2 binding pocket was used to identify S1PR2 antagonists.

To identify antagonists of S1PR2 by computational means, the Molecular Operating Environment (MOE) program was used to perform modeling on the S1PR1 structure. Throughout the process, the CHARMM27 force field was implemented and a gas phase environment was specified. The amino acid sequence of S1PR2 was obtained from the UniProt archive. The amino acid sequences of S1PR2 and S1PR1 were aligned, and a homology model was generated from the alignment. The generated model was protonated for a temperature of 310K, a pH of 7.0, and a salt concentration of 0.1 mol/L. The site finder tool in MOE was used to identify the binding pocket of the receptor. A pocket composed of 34 amino acids located on the extracellular face of the protein was identified (FIG. 8).

Figure 9:
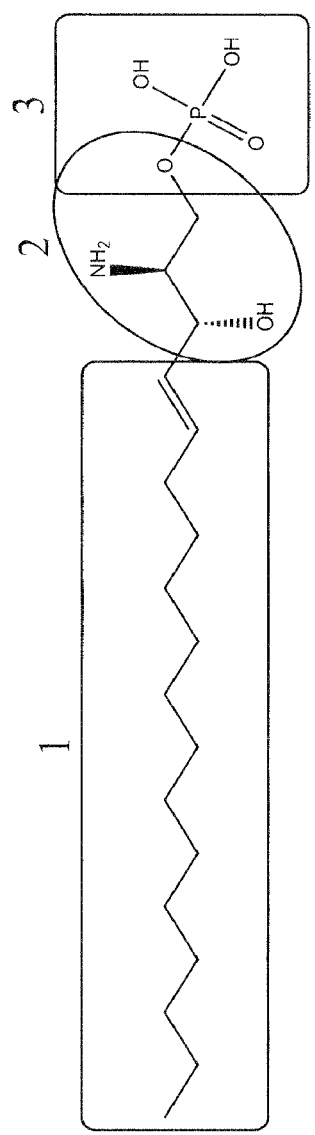
FIG. 9 illustrates the sphingosine-1-phosphate and its identified target regions. These identified compounds interact with the binding pocket more strongly than its known receptor, and thus prevent S1P from binding. The identified compounds are available for purchase.

As shown in FIG. 9, the main ligand of the S1PR2 receptor, S1P, has three distinct chemical regions. These regions were used to search the PubChem and hit-to-lead databases for similar molecules containing either region 1, 2 or 3. As well, sulfate groups were also included in the search as they are bioisosteres of phosphate. Compounds were identified based on the following criteria: they must have a molecular weight less than 390, an XLogP value between −1 and 7 for regions 2 and 3, or an XLogP value less than 5 and a total polar surface area from 35-120 for region 1. The compounds identified from each region were imported into MOE as a database. A total of 62,125 results were obtained for region1; 2,971 for region 2, and; 13,442 for region 3. These molecules were first washed to remove any salt ions that may have been included in the structure, and were energy optimized using the CHARMM27 force field in a gas phase environment. The compounds were then submitted to a virtual screen through the identified binding pocket on S1PR2.

From the results of the virtual screen, the best 100 compounds for each region were selected and subjected to a more rigorous method of docking: induced fit versus S1PR2 and S1PR1. This docking allows for the amino acid side chains lining the pocket to move, as well as the ligand being docked. The resulting databases were examined for compounds with an S score that was better than the score of S1P, and have predicted specificity for S1PR2 versus S1PR1. The identified compounds were then screened for availability to purchase and 36 compounds were found to be commercially available and were selected as viable targets for testing. As shown in FIG. 11 A-D, those from PubChem using their PubChem identification numbers are the following: 3382778; 44317142 (also as 520 and 644260); 54736865; 3866342; 46891770 (also as 3247041); 51624406; 9578291;

9864156; 365015; 28094480; 40592676; 10883396; 342302; 56923845; 54734912; 18390590; 56923928; 51508548; 28960354; 51624683; 27993.

Their efficacy can readily be compared to JTE-013, a S1PR antagonist with specificity for selective S1PR2 inhibition.

Example 4

Figure 10:
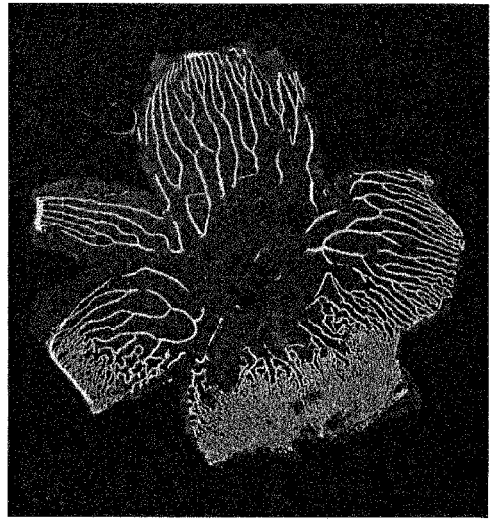
FIG. 10 illustrates that inactivation of the fzd4 gene in adult zebrafish results in the aberrant neovascularization observed in humans and mice. To target the fzd4 gene, a pair of TALEN nucleases was created. The founders carrying a significant proportion of the mutation were mated to flil: EGFP transgenic fish (GFP marker for vasculature) and the resulting F1 fish were grown to adulthood. An insertion of 10 nucleotides was confirmed in the open reading frame of the fzd4 gene. Pairs of fzd4 heterozygous fish were mated to produce progeny containing homozygous mutants. Homozygous mutant fish did not have any apparent embryonic phenotype and were grown to adulthood. To check if the retinal vasculature is affected by the fzd4 mutation, retinas were dissected and flat mounted from wild-type and mutant fish and were visualized by confocal microscopy. The homozygous fzd4$^{-/-}$ mutants have a large area of avascularity and an abnormal vascular pattern in the vascularized areas.
Figure 10:
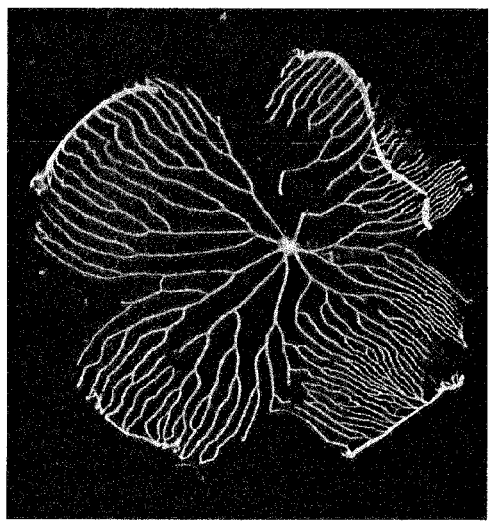
Figure 11A:
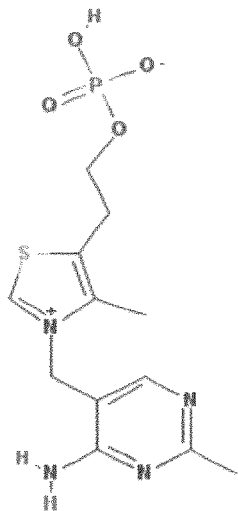
FIG. 11 A-D, illustrates 21 compounds that were identified as viable new S1PR2 antagonists.
Figure 11A:
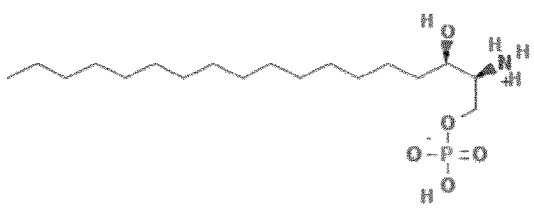
Figure 11A:
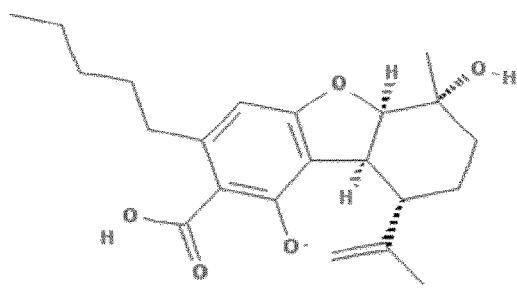
Figure 11A:
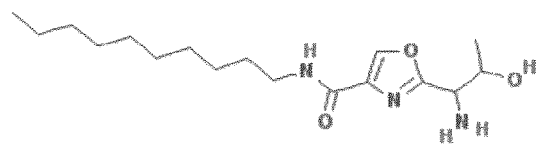
Figure 11A:
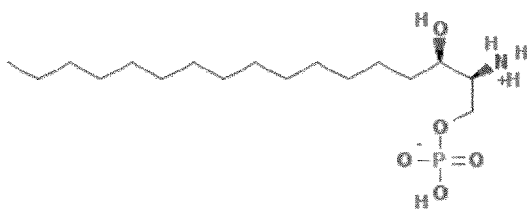
Figure 11A:
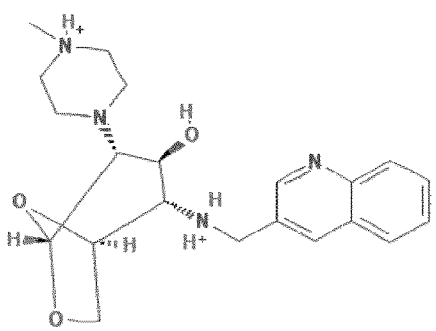
Figure 11B:
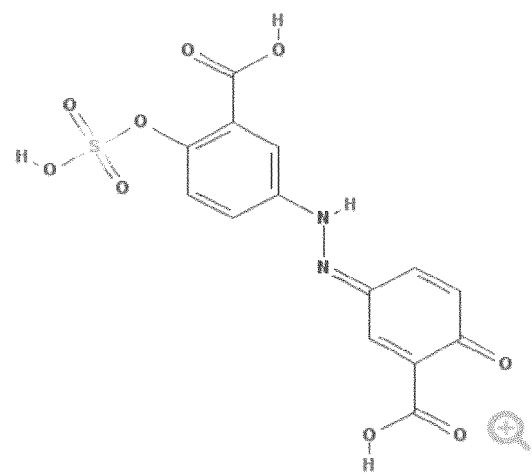
Figure 11B:
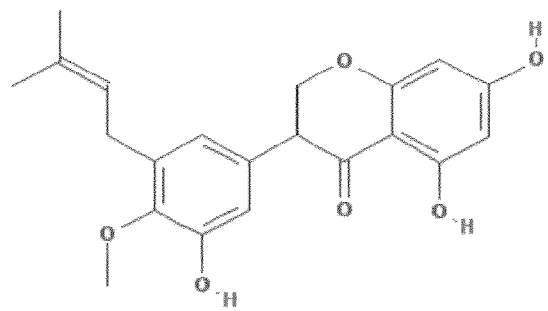
Figure 11B:
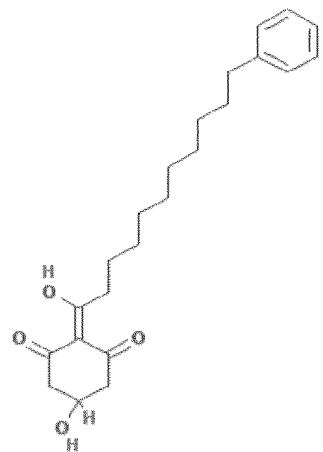
Figure 11B:
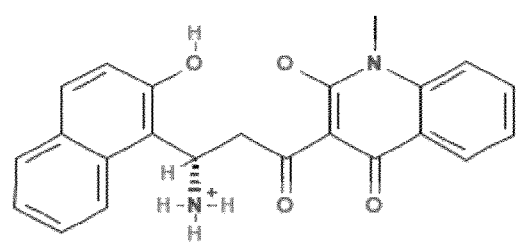
Figure 11C:
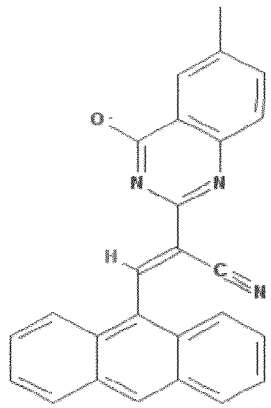
Figure 11C:
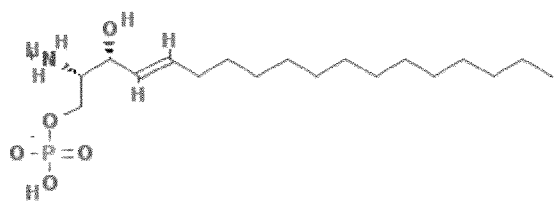
Figure 11C:
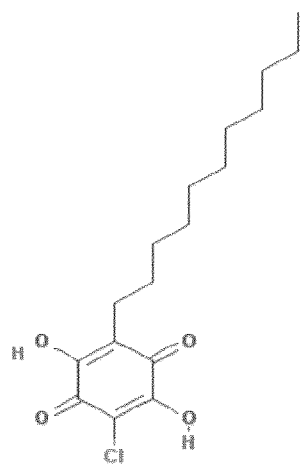
Figure 11C:
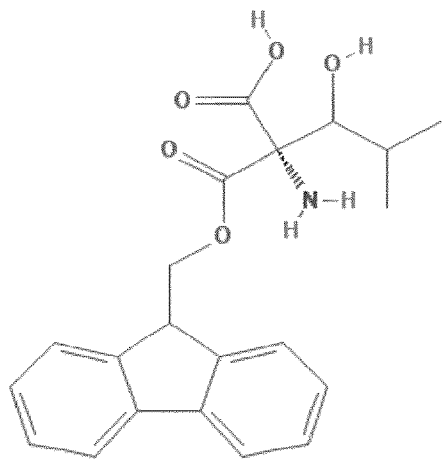
Figure 11C:
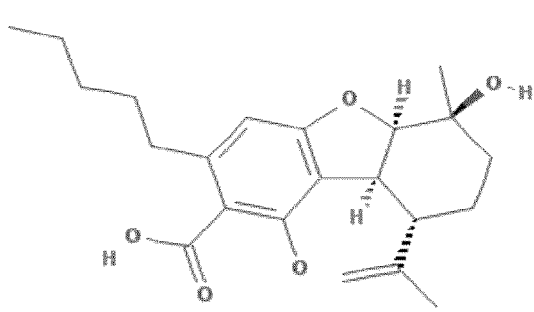
Figure 11C:
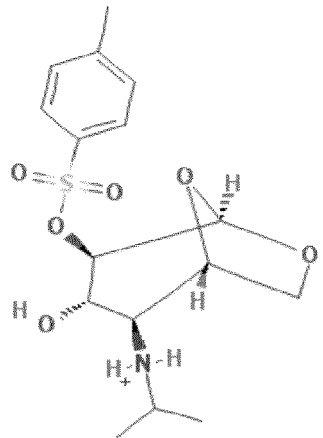
Figure 11D:
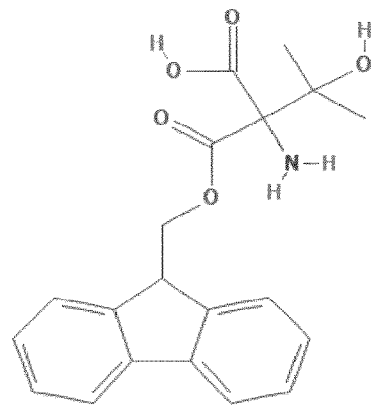
Figure 11D:
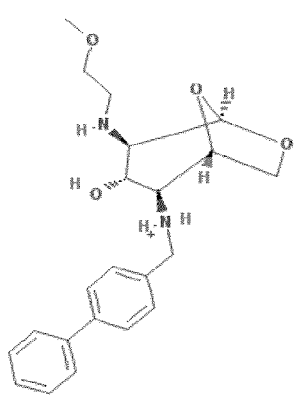
Figure 11D:
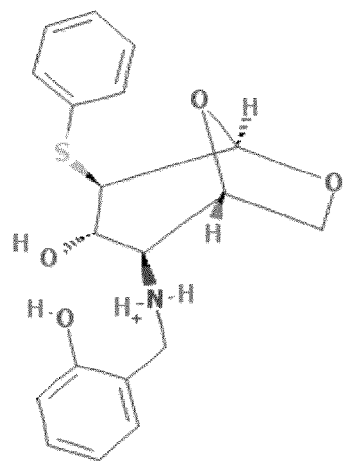
Figure 11D:
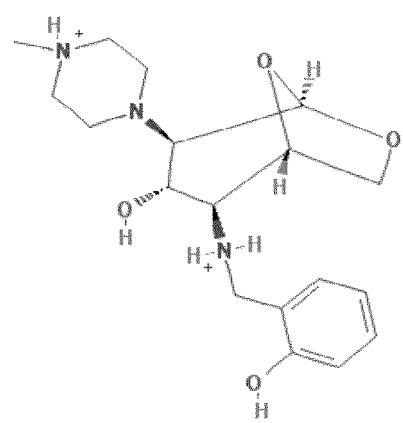
Figure 11D:
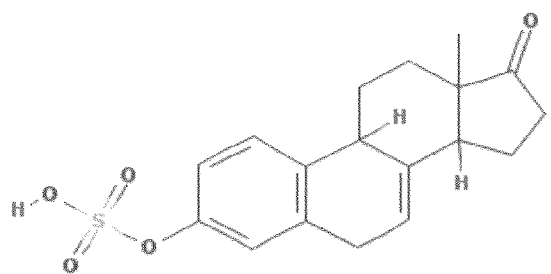

Demonstration and Ranking of S1PR2 Antagonist Activity in Zebrafish Models of FEVR Knockout approaches permit the generation of zebrafish models that recapitulate human diseases, allowing for a rapid intermediate in vivo step for drug screening prior to more time consuming and expensive mammalian studies. The S1PR2 drug target and the FZD4 pathway are highly conserved between zebrafish, mice, and humans. The TALEN system was used to generate germ line fzd4$^{-/-}$ zebrafish (FIG. 10).

To assay the identified S1PR2 antagonists as well as the known tool compound JTE-013, three fzd4$^{-/-}$ zebrafish embryos are arrayed in 96-well plates. At 24 hours post-fertilization (hpf) compounds are then transferred to the embryo plate at final concentrations of 0.01-30 μM. Embryos are then incubated with compounds at 28.5° C. for 12 h and screened for gross global developmental effects. At various time frames (2-12 days) embryos are then overdosed with Tricaine (MS-222) and fixed in 4% paraformaldehyde and their retinal vasculature can be determined using microscopy. Those compounds that best restore normal vasculature to zebrafish are subsequently tested in the Tspan12$^{-/-}$ and Fzd4$^{-/-}$ mice to isolate the most effective therapeutic compounds.

For work in mice, compounds are delivered by intraocular injection to the eye (0.01-30 μM) of mice between P17 and P28 that can be effectively treated by a S1PR2 antagonist. This time frame is similar to that at what stage FEVR occurs in humans. Retinal phenotypes and ocular function are then determined as described above for the study of the the Tspan12$^{-/-}$ and Fzd4$^{-/-}$ FEVR mouse models and other genetic models of FEVR.

Example 5

Synthesis of (Z)-2-cyano-1-(2,6-dichloropyridin-4-yl)-3-((4-isopropyl-1,3-dimethyl-1H-pyrazolo[3,4-b]pyridin-6-yl)methyl)guanidine and Analogs Thereof (Z)-2-cyano-1-(2,6-dichloropyridin-4-yl)-3-((4-isopropyl-1,3-dimethyl-1H-pyrazolo[3,4-b]pyridin-6-yl)methyl) guanidine and its analogs are synthesized as described below. In particular, these compounds are synthesized using combinations of Intermediate A, and Intermediate B or C.

Intermediate A is synthesized according to Scheme A.

Scheme A

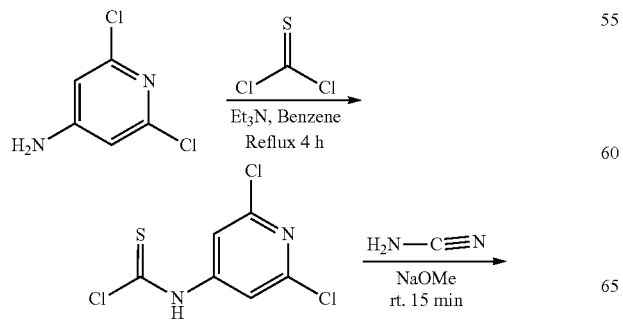

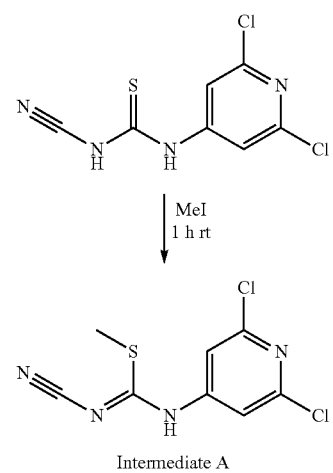

Intermediate A

Intermediate B is synthesized according to Scheme B.

Scheme B

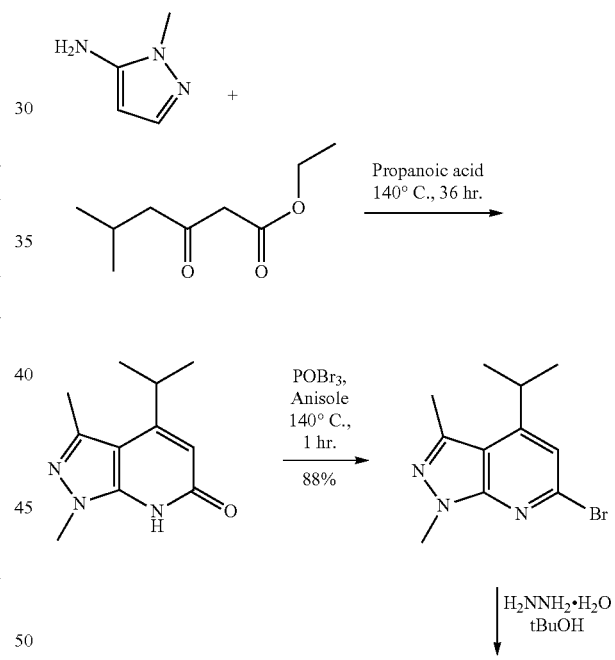

Intermediate B

Intermediate C is synthesized according to Scheme C.

Scheme C

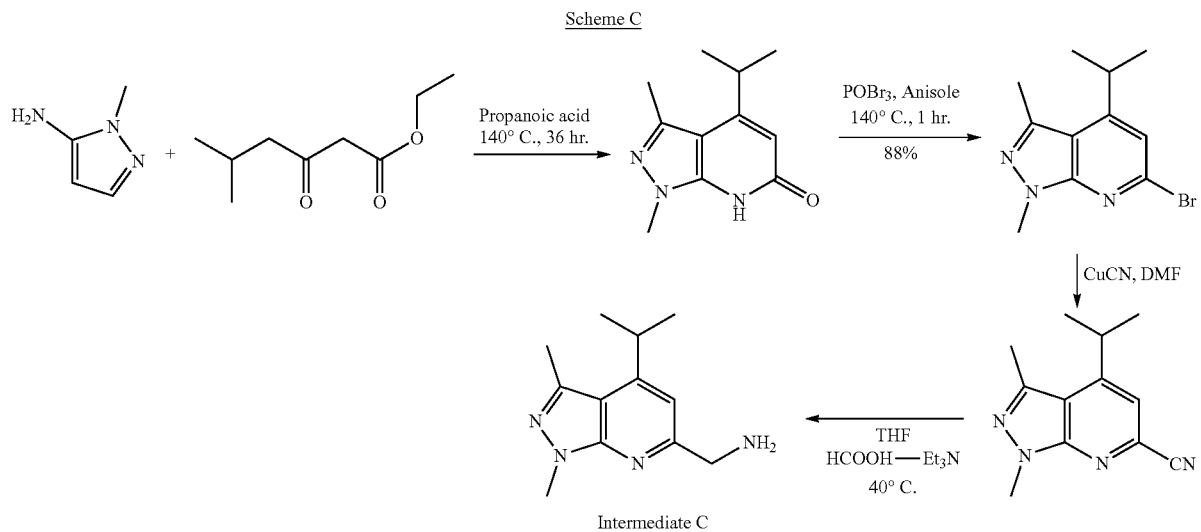

Intermediate C

Synthesis of (E)-N'-cyano-N-(2,6-dichloropyridin-4-yl)-2-(4-isopropyl-1,3-dimethyl-1H-pyrazolo[3,4-b]pyridin-6-yl)hydrazinecarboximidamide and (Z)—N'-cyano-N-(2,6-dichloropyridin-4 -yl)-2-(4-isopropyl-1,3-dimethyl-1H-pyrazolo[3,4-b]pyridin-6-yl) hydrazinecarboximidamide (E)-N'-cyano-N-(2,6-dichloropyridin-4-yl)-2-(4-isopropyl-1,3-dimethyl-1H-pyrazolo[3,4-b]pyridin-6-yl)hydrazinecarboximidamide and (Z)—N'-cyano-N-(2,6-dichloropyridin-4-yl)-2-(4-isopropyl-1,3-dimethyl-1H-pyrazolo[3,4-b]pyridin-6-yl)hydrazinecarboximidamide are synthesized according to Scheme 1.

Scheme 1

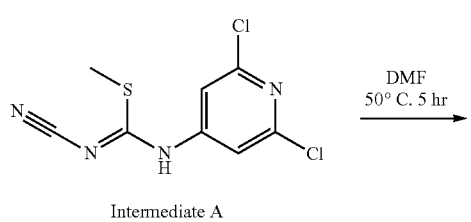

Intermediate B

-continued

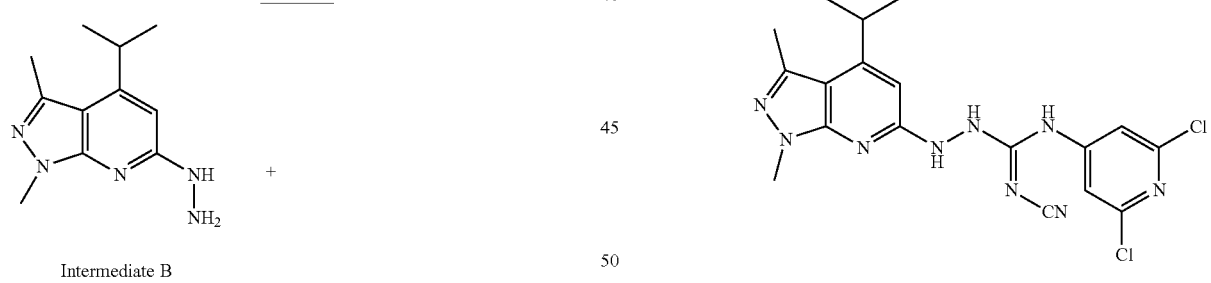

Structural Isomers Separated By RP-HPLC

Synthesis of (E)-2-cyano-1-(2,6-dichloropyridin-4-yl)-3-((4-isopropyl-1,3-dimethyl-1H-pyrazolo[3,4-b]pyridin-6-yl)methyl)guanidine and (Z)-2-cyano-1-(2,6-dichloropyridin-4-yl)-3-((4-isopropyl-1,3-dimethyl-1H-pyrazolo[3,4-b]pyridin-6-yl)nethyl)guanidine (E)-2-cyano-1-(2,6-dichloropyridin-4-yl)-3-((4-isopropyl-1,3-dimethyl-1H-pyrazolo[3,4-b]pyridin-6-yl)methyl)guanidine and (Z)-2-cyano-1-(2,6-dichloropyridin-4-yl)-3-((4-isopropyl-1,3-dimethyl-1H-pyrazolo[3,4-b]pyridin-6-yl)methyl)guanidine are synthesized according to Scheme 2.

Scheme 2

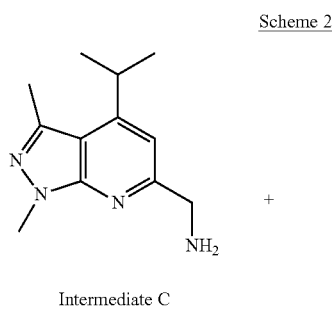

Intermediate C

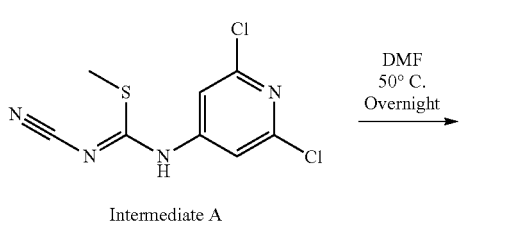

Intermediate A

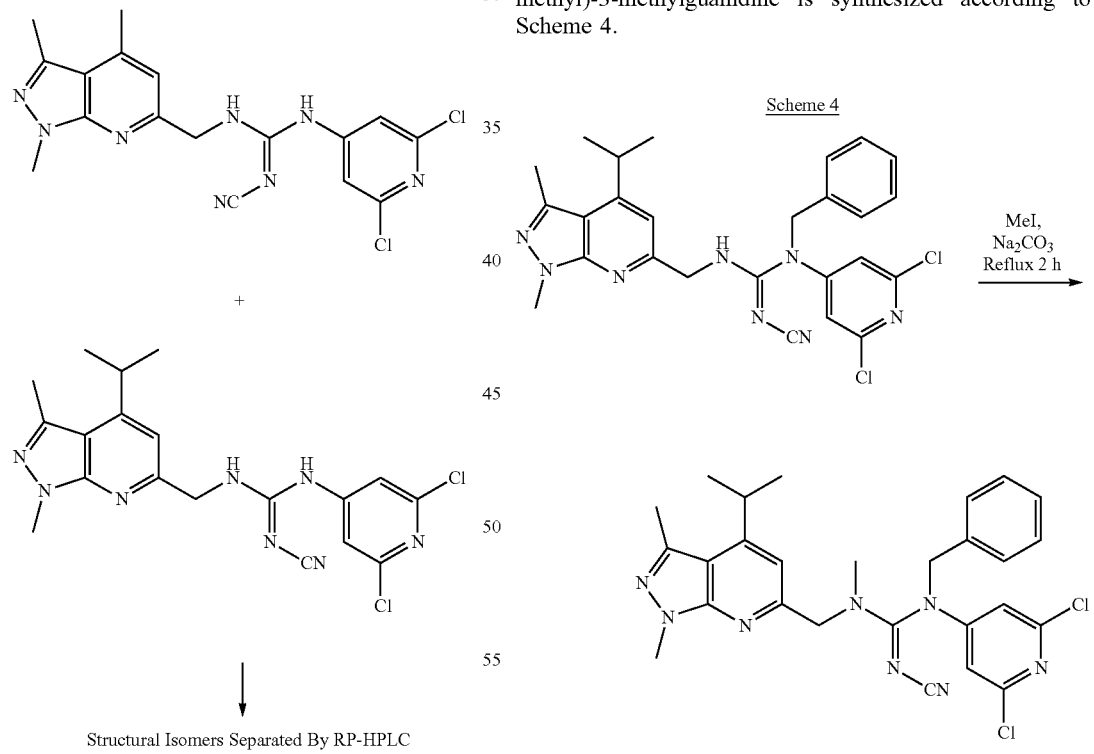

Structural Isomers Separated By RP-HPLC

Synthesis of (Z)-1-benzyl-2-cyano-1-(2,6-dichloropyridin-4-yl)-3-((4-isopropyl-1,3-dimethyl-1H-pyrazolo[3,4-b]pyridin-6-yl)methyl)guanidine (Z)-1-benzyl-2-cyano-1-(2,6-dichloropyridin-4-yl)-3-((4-isopropyl-1,3-dimethyl-1H-pyrazolo[3,4-b]pyridin-6-yl)methyl)guanidine is synthesized according to Scheme 3.

Scheme 3

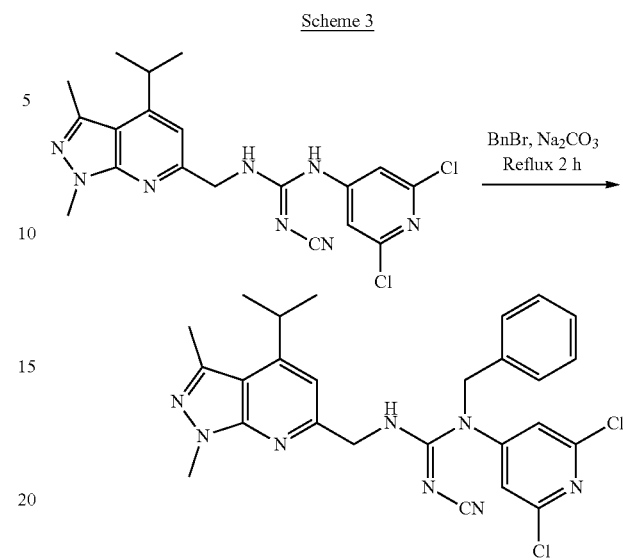

Synthesis of (Z)-1-benzyl-2-cyano-1-(2,6-dichloropyridin-4-yl)-3-((4-isopropyl-1,3-dimethyl-1 H-pyrazolo[3,4-b]pyridin-6-yl)methyl)-3-methylguanidine (Z)-1-benzyl-2-cyano-1-(2,6-dichloropyridin-4-yl)-3-((4-isopropyl-1,3-dimethyl-1H-pyrazolo[3,4-b]pyridin-6-yl)methyl)-3-methylguanidine is synthesized according to Scheme 4.

Scheme 4

Synthesis of (Z)—N-(1-(2,6-dichloropyridin-4-yl)-3-((4-isopropyl-1,3-dimethyl-1H-pyrazolo[3,4-b]pyridin-6-yl)methyl)tetrahydropyrimidin-2(1H)-ylidene)cyanamide (Z)—N-(1-(2,6-dichloropyridin-4-yl)-3-((4-isopropyl-1,3-dimethyl-1H-pyrazolo[3,4-b]pyridin-6-yl)methyl)tetrahydropyrimidin-2(1H)-ylidene)cyanamide is synthesized according to Scheme 5.

Scheme 5

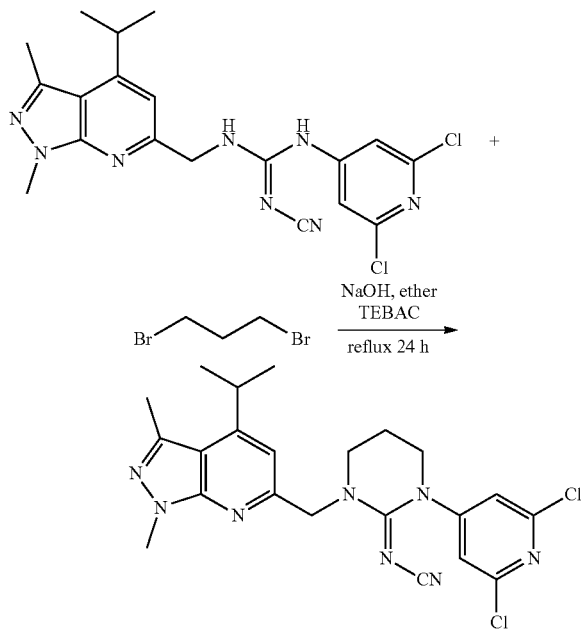

A person of ordinary skill in the art would recognize that alternatives to the above-described methods of synthesis in this example could be used to generate (Z)-2-cyano-1-(2,6-dichloropyridin-4-yl)-3-((4-isopropyl-1,3-dimethyl-1H-pyrazolo[3,4-b]pyridin-6-yl) methyl)guanidine and its analogs described herein.

The invention claimed is:

1. A compound of formula (XII):

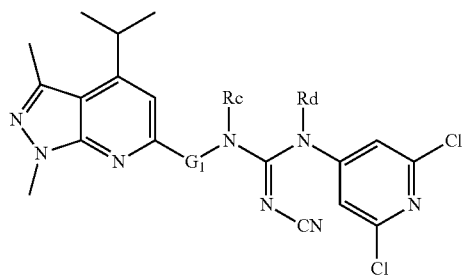

or a pharmaceutically acceptable salt thereof,
wherein:
$G_1$ is $CR_{12}$ or $NR_{13}$, wherein $R_{12}$ and $R_{13}$ are each independently selected from the group consisting of H, $C_1$-$C_4$ alkyl, and benzyl;
$R_c$ and $R_d$ are independently selected from the group consisting of H, $C_1$-$C_4$ alkyl, and benzyl; or $R_c$ and $R_d$ are joined to form a 5- or 6-membered heterocycloalkyl ring; and,
the cyano group is in the (Z) or (E) configuration.

2. The compound or pharmaceutically acceptable salt thereof of claim 1, wherein:
$G_1$ is $CR_{12}$ and $R_{12}$ is H; and,
$R_d$ is H.

3. The compound of claim 2, selected from the group consisting of:

(E)-2-cyano-3-(2,6-dichloropyridin-4-yl)-1-((4-isopropyl-1,3-dimethyl-1H-pyrazolo[3,4-b]pyridin-6-yl) methyl)-1-methylguanidine;
(E)-2-cyano-3-(2,6-dichloropyridin-4-yl)-1-ethyl-1-((4-isopropyl-1,3-dimethyl-1H-pyrazolo[3,4-b]pyridin-6-yl)methyl)guanidine;
(E)-2-cyano-3-(2,6-dichloropyridin-4-yl)-1-((4-isopropyl-1,3-dimethyl-1H-pyrazolo[3,4-b]pyridin-6-yl) methyl)-1-propylguanidine;
(E)-1-butyl-2-cyano-3-(2,6-dichloropyridin-4-yl)-1-((4-isopropyl-1,3-dimethyl-1H-pyrazolo[3,4-b]pyridin-6-yl)methyl)guanidine;
(E)-2-cyano-3-(2,6-dichloropyridin-4-yl)-1-isopropyl-1-((4-isopropyl-1,3-dimethyl-1H-pyrazolo[3,4-b]pyridin-6-yl)methyl)guanidine;
(E)-1-benzyl-2-cyano-3-(2,6-dichloropyridin-4-yl)-1-((4-isopropyl-1,3-dimethyl-1H-pyrazolo[3,4-b]pyridin-6-yl)methyl)guanidine; and,
a diastereomer of the foregoing, wherein the cyano group is in the (Z) form; or the pharmaceutically acceptable salt of any of the foregoing.

4. The compound or pharmaceutically acceptable salt thereof of claim 1, wherein:
$G_1$ is $CR_{12}$ and $R_{12}$ is H; and,
$R_c$ is H.

5. The compound of claim 4, selected from the group consisting of:

(Z)-2-cyano-1-(2,6-dichloropyridin-4-yl)-3-((4-isopropyl-1,3-dimethyl-1H-pyrazolo[3,4-b]pyridin-6-yl) methyl)-1-methylguanidine;
(Z)-2-cyano-1-(2,6-dichloropyridin-4-yl)-1-ethyl-3-((4-isopropyl-1,3-dimethyl-1H-pyrazolo[3,4-b]pyridin-6-yl)methyl)guanidine;
(Z)-2-cyano-1-(2,6-dichloropyridin-4-yl)-3-((4-isopropyl-1,3-dimethyl-1H-pyrazolo[3,4-b]pyridin-6-yl) methyl)-1-propylguanidine;
(Z)-1-butyl-2-cyano-1-(2,6-dichloropyridin-4-yl)-3-((4-isopropyl-1,3-dimethyl-1H-pyrazolo[3,4-b]pyridin-6-yl)methyl)guanidine;
(Z)-2-cyano-1-(2,6-dichloropyridin-4-yl)-1-isopropyl-3-((4-isopropyl-1,3-dimethyl-1H-pyrazolo[3,4-b]pyridin-6-yl)methyl)guanidine;
(Z)-1-benzyl-2-cyano-1-(2,6-dichloropyridin-4-yl)-3-((4-isopropyl-1,3-dimethyl-1H-pyrazolo[3,4-b]pyridin-6-yl)methyl)guanidine; and,
a diastereomer of the foregoing, wherein the cyano group is in the (E) form; or the pharmaceutically acceptable salt of any of the foregoing.

6. The compound or pharmaceutically acceptable salt thereof of claim 1, wherein:
$G_1$ is $CR_{12}$; and,
$R_c$ and $R_d$ are each H.

7. The compound of claim 6, selected from the group consisting of:

(Z)-2-cyano-1-(2,6-dichloropyridin-4-yl)-3-(1-(4-isopropyl-1,3-dimethyl-1H-pyrazolo[3,4-b]pyridin-6-yl) ethyl)guanidine;
(Z)-2-cyano-1-(2,6-dichloropyridin-4-yl)-3-(1-(4-isopropyl-1,3-dimethyl-1H-pyrazolo[3,4-b]pyridin-6-yl)propyl)guanidine;
(Z)-2-cyano-1-(2,6-dichloropyridin-4-yl)-3-(1-(4-isopropyl-1,3-dimethyl-1H-pyrazolo[3,4-b]pyridin-6-yl)-2-methylpropyl)guanidine;
(Z)-2-cyano-1-(2,6-dichloropyridin-4-yl)-3-(1-(4-isopropyl-1,3-dimethyl-1H-pyrazolo[3,4-b]pyridin-6-yl)-2-phenylethyl)guanidine; and, a diastereomer of the foregoing, wherein the cyano group is in the (E) form; or the pharmaceutically acceptable salt of any of the foregoing.

8. The compound or pharmaceutically acceptable salt thereof of claim 1, wherein:
   $G_1$ is $NR_{13}$; and,
   $R_c$ and $R_d$ are each H.

9. The compound of claim 8, selected from the group consisting of:
   (E)-N'-cyano-N-(2,6-dichloropyridin-4-yl)-2-(4-isopropyl-1,3-dimethyl-1H-pyrazolo[3,4-b]pyridin-6-yl)hydrazinecarboximidamide;
   (E)-N'-cyano-N-(2,6-dichloropyridin-4-yl)-2-(4-isopropyl-1,3-dimethyl-1H-pyrazolo[3,4-b]pyridin-6-yl)-2-methylhydrazinecarboximidamide;
   (E)-N'-cyano-N-(2,6-dichloropyridin-4-yl)-2-ethyl-2-(4-isopropyl-1,3-dimethyl-1H-pyrazolo[3,4-b]pyridin-6-yl)hydrazinecarboximidamide;
   (E)-N'-cyano-N-(2,6-dichloropyridin-4-yl)-2-(4-isopropyl-1,3-dimethyl-1H-pyrazolo[3,4-b]pyridin-6-yl)-2-propylhydrazinecarboximidamide;
   (E)-2-butyl-N'-cyano-N-(2,6-dichloropyridin-4-yl)-2-(4-isopropyl-1,3-dimethyl-1H-pyrazolo[3,4-b]pyridin-6-yl)hydrazinecarboximidamide;
   (E)-N'-cyano-N-(2,6-dichloropyridin-4-yl)-2-isopropyl-2-(4-isopropyl-1,3-dimethyl-1H-pyrazolo[3,4-b]pyridin-6-yl)hydrazinecarboximidamide;
   (E)-2-b enzyl-N'-cyano-N-(2,6-dichloropyridin-4-yl)-2-(4-isopropyl-1,3-dimethyl-1H-pyrazolo[3,4-b]pyridin-6-yl)hydrazinecarboximidamide; and,
   a diastereomer of the foregoing, wherein the cyano group is in the (Z) form; or the pharmaceutically acceptable salt of any of the foregoing.

10. The compound or pharmaceutically acceptable salt thereof of claim 1, wherein:
    $G_1$ is $CR_{12}$ and $R_{12}$ is H.

11. The compound of claim 10, selected from the group consisting of:
    (Z)-2-cyano-1-(2,6-dichloropyridin-4-yl)-3-((4-isopropyl-1,3-dimethyl-1H-pyrazolo[3,4-b]pyridin-6-yl)methyl)-1,3-dimethylguanidine;
    (Z)-2-cyano-1-(2,6-dichloropyridin-4-yl)-3-isopropyl-3-((4-isopropyl-1,3-dimethyl-1H-pyrazolo[3,4-b]pyridin-6-yl)methyl)-1-methylguanidine;
    (Z)-2-cyano-1-(2,6-dichloropyridin-4-yl)-1-isopropyl-3-((4-isopropyl-1,3-dimethyl-1H-pyrazolo[3,4-b]pyridin-6-yl)methyl)-3-methylguanidine;
    (Z)-1-benzyl-2-cyano-3-(2,6-dichloropyridin-4-yl)-1-((4-isopropyl-1,3-dimethyl-1H-pyrazolo[3,4-b]pyridin-6-yl)methyl)-3-methylguanidine;
    (Z)-1-benzyl-2-cyano-1-(2,6-dichloropyridin-4-yl)-3-((4-isopropyl-1,3-dimethyl-1H-pyrazolo[3,4-b]pyridin-6-yl)methyl)-3-methylguanidine; and,
    a diastereomer of the foregoing, wherein the cyano group is in the (E) form; or the pharmaceutically acceptable salt of any of the foregoing.

12. The compound or pharmaceutically acceptable salt thereof of claim 1, wherein:
    $G_1$ is $CR_{12}$ and $CR_{12}$ is H; and,
    $R_c$ and $R_d$ are joined to form a 5- or 6-membered heterocycloalkyl ring.

13. The compound of claim 12, selected from the group consisting of:
    (Z)—N-(1-(2,6-dichloropyridin-4-yl)-3-((4-isopropyl-1,3-dimethyl-1H-pyrazolo[3,4-b]pyridin-6-yl)methyl)tetrahydropyrimidin-2(1H)-ylidene)cyanamide;
    (Z)—N-(1-(2,6-dichloropyridin-4-yl)-3-((4-isopropyl-1,3-dimethyl-1H-pyrazolo[3,4-b]pyridin-6-yl)methyl)imidazolidin-2-ylidene)cyanamide; and,
    a diastereomer of the foregoing, wherein the cyano group is in the (E) form; or the pharmaceutically acceptable salt of any of the foregoing.

14. A method of treating an eye condition in a subject in need thereof, comprising administering to the subject a pharmaceutically effective amount of the compound of claim 1, or a pharmaceutically-acceptable salt thereof.

15. The method of claim 14, wherein the eye condition is caused by a primary defect in retinal vascularization followed by secondary aberrant neovascularization that can result in retina detachment.

16. The method of claim 14, wherein the eye condition is a retinopathy.

17. The method of claim 16, wherein the retinopathy is selected from the group consisting of diabetic retinopathy, macular degeneration, hypertensive retinopathy, radiation retinopathy, solar retinopathy, retinopathy of prematurity (ROP), Norrie disease (ND), familial exudative vitreoretinopathy (FEVR), Coats' disease, sickle cell retinopathy, and retinitis pigmentosa.

18. The method of claim 17, wherein the retinopathy is FEVR.

19. A method of treating a disease characterized by insufficient angiogenesis in a subject in need thereof, comprising administering to the subject a pharmaceutically effective amount of the compound of claim 1, or a pharmaceutically-acceptable salt thereof.

20. The method of claim 19, wherein the disease is selected from the group consisting of atherosclerosis, hypertension, diabetes, restenosis, pre-eclampsia, menorrhagia, neonatal respiratory distress, pulmonary fibrosis, nephropathy, osteoporosis, amyotrophic lateral sclerosis, stroke, and Alzheimer's disease.

* * * * *